United States Patent
Calabi et al.

(10) Patent No.: US 6,403,055 B1
(45) Date of Patent: Jun. 11, 2002

(54) DIAGNOSTIC IMAGING CONTRAST AGENT WITH IMPROVED IN SERUM RELAXIVITY

(75) Inventors: Luisella Calabi; Alessandro Maiocchi; Marco Lolli; Fabrizio Rebasti, all of Milan (IT)

(73) Assignee: Dibra S.p.A., Milan (IT)

( * ) Notice: Subject to any disclaimer, the term of this patent is extended or adjusted under 35 U.S.C. 154(b) by 0 days.

(21) Appl. No.: 09/612,392

(22) Filed: Jul. 7, 2000

Related U.S. Application Data

(63) Continuation-in-part of application No. 08/904,644, filed on Aug. 1, 1997, now abandoned.

(30) Foreign Application Priority Data

Aug. 2, 1996 (IT) .......................... M196A1684

(51) Int. Cl.[7] .............................. A61B 5/055
(52) U.S. Cl. ................. 424/9.364; 424/9.1; 424/9.3; 424/9.36; 424/1.65
(58) Field of Search ................. 424/1.11, 9.1, 424/9.3, 9.32, 9.323, 9.36, 9.361, 9.364, 1.65; 534/7, 10–16

(56) References Cited

U.S. PATENT DOCUMENTS

| | | |
|---|---|---|
| 4,505,956 A | 3/1985 | Yamamoto et al. |
| 5,057,302 A | 10/1991 | Johnson et al. |
| 5,182,370 A | 1/1993 | Felder et al. |
| 5,453,264 A | 9/1995 | Mori et al. |
| 5,547,817 A | 8/1996 | Okada et al. |
| 5,567,411 A | 10/1996 | Keana et al. |
| 5,582,814 A | 12/1996 | Scott et al. |
| 5,672,335 A | 9/1997 | Krause et al. |
| 5,733,522 A | 3/1998 | Schmitt-Willich et al. |
| 5,746,995 A | 5/1998 | Maier et al. |
| 5,885,548 A * | 3/1999 | Maier et al. ............ 424/1.65 |

FOREIGN PATENT DOCUMENTS

| | | |
|---|---|---|
| WO | WO 8203880 A | 11/1982 |
| WO | 96/16677 | 11/1995 |

OTHER PUBLICATIONS

Cavagna et al., In vestigative Radiology, Dec. 1997, vol. 32, No. 12, pp. 780–796.*

* cited by examiner

Primary Examiner—Dameron L. Jones
(74) Attorney, Agent, or Firm—Nixon & Vanderhye

(57) ABSTRACT

Compounds of formula (I):

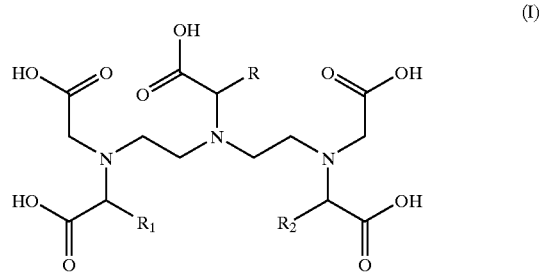

are used as their paramagnetic chelates as contrast agents in magnetic resonance imaging. These compounds have high affinity to plasma proteins and exhibit extremely high values of relaxivity in serum and are thus useful as blood pool contrast agents.

7 Claims, No Drawings

DIAGNOSTIC IMAGING CONTRAST AGENT WITH IMPROVED IN SERUM RELAXIVITY

This application is a continuation-in-part of application Ser. No. 08/904,644, filed Aug. 1, 1997, now abandoned the entire content of which is hereby incorporated by reference in this application.

TECHNICAL FIELD OF THE INVENTION

This invention relates to the Magnetic Resonance Imaging (M.R.I.), a technique used in the medical diagnosis field for a number of years, to rapidly detect a series of anomalies and/or pathological conditions of living human or animal body organs or tissues. (i. e.: Stark D. D., Bradley W. G. Jr., Eds.: "Magnetic Resonance Imaging", the C.V. Mosby Company, St. Louis, Mo. (USA), 1988). In particular, the invention relates to new chelating agents, especially aminopolycarboxylic acid derivative compounds and to metal chelates thereof with bivalent or trivalent paramagnetic ions and/or salts thereof as well as their use as M.R.I. contrast agents.

BACKGROUND OF THE INVENTION

Diagnostic imaging techniques, such as Magnetic Resonance Imaging have been used in medical diagnosis for a long time. The use of contrast media to improve tissue differentiation, to delineate structures or monitor physiological functions constitutes in some cases a fundamental contribution in the best formulation of some medical diagnosis and a valid support for radiologist work.

The medical use of aminopolycarboxylic acid or carboxylic acid derivatives and metal chelates thereof as M.R.I. contrast agents is well known. Said contrast agents, to simplify, can be seen as pertaining to two main groups: the linear and the cyclic ones.

The present invention relates to linear polyaminopolycarboxylic acid derivatives, as well as their complexes with paramagnetic metal ions, in particular the $Gd^{3+}$ ion.

Patent literature is rich in patent and patent applications relating to the use of linear polyaminopolycarboxylic acid derivatives in the preparation of MRI contrast agents. These compounds generally are derived from the simplest one, N,N,N',N",N"-diethylenetriamine-pentaacetic acid, (DTPA), of which the Meglumine salt of the $Gd^{3+}$ complex has been commercialised for a number of years as MAG-NEVIST™. To improve stability, water solubility and selectivity and to reduce toxicity of these contrast agents generally patent literature proposes the preparation of esters or amide derivatives of said acids or the introduction of substituents on the diethylene unit of the diethylenetriamine DTPA skeleton. As an example of said patent literature we can cite: Guerbet EP 661279; Concat Ltd., WO 95/05118; Dibra WO 95/15319; Mallinckrodt WO 94/08630; Green Gross Corp. JP 06016606 and JP 05229998; Mallinckrodt U.S. Pat. Nos. 5,141,740 and 5,077,037; Cockbain-Nycomed WO 91/15467 and WO 92/11232; Salutar U.S. Pat. Nos. 4,889,931 and 4,858,451; Abbot Laboratoires EP 279307; Nycomed EP 299795; Metasyn Inc. WO 95/28179; Schering EP 680 464; and document cited in these patent publications. Some documents further exist in which substituents have been introduced in ($\alpha$) to one or more carboxylic DTPA groups; for example: Bracco EP-B-230893 and U.S. Pat. No. 5,182,370; Schering WO 96/16928, WO 96/16929, WO 96/26180 and DE 4341724 enclosing $\alpha$ derivatives, generally comprising an aromatic group, particularly useful for the imaging of the hepatobiliary system.

In particular, some patent literature further exists, in which the introduction of an aromatic or lipophilic group on the chelant structure is specifically stated to make the contrast agent as particularly useful for a best definition of the liver and the biliary duct: the General Hospital Corporation U.S. Pat. No. 4,899,755 and WO-A-86/06605.

Further relevant documents disclosing DTPA derivatives which carry substituents in $\alpha$ position to the carboxy groups of the DTPA skeleton exist. Among the others, U.S. Pat. No. 5,885,548 describes DTPA analogs carrying a radicals which comprise at least one aryl group. No alicyclic substituents are indicated as possible substituents. The chelate complex of the invention are strongly preferred for the imaging of the liver, the bile ducts and the gallbladder, wichever the diagnostic technique is. U.S. Pat. No. 5,853,699 describes a range of compounds similar to the preceiding ones. In this case the preferred and strongly recommended ones are tetraazamacrocycles and are described and claimed only as contrast agents for the imaging of the liver by using the Computer Tomography, i. e. X-rays. No mention of a possible use with the Magnetic Resonance is done nor even suggested. DTPA derivatives $\alpha$ substituted, whereas the possible $\alpha$ substituents are only lower alkyl groups, and where said derivatives are in any case mono or diamido compounds are also disclosed in U.S. Pat. No. 5,453,264. No mention of possible cyclic moieties in the $\alpha$ substituents is done or suggested. Also U.S. Pat. No. 5,672,335 discloses DTPA derivatives with possible substituents, comprising at least one aromatic ring, in $\alpha$ position to the carboxy groups. Even this patent only suggests the imaging of the liver and bile ducts by using the X-rays (Computer Tomography), not magnetic resonance. The general teaching of the prior-art concerns the possibility of finding compounds that are particularly useful for the imaging of liver, bile ducts, gall bladder provided that lipophilic substituents are attached to the chelating moiety. More lipophilic substituents are highly preferred/needed for obtaining liver specificity. No mention, nor even suggestion is made to the possibility that such DTPA derivatives can show very high relaxivity values in serum, and, on consequence, the capability of strongly bonding to the serum proteins.

SUMMARY OF THE INVENTION

The compounds of the present invention are diethylenetriaminepentaacetic acid derivatives characterised in having substituents at the a position to the carboxy group of two or three of the five acetic groups of DTPA. More precisely, the compounds can have two substituents (the same or different from each other) in $\alpha$ to the carboxyls of the two acetic groups respectively bound to the two side nitrogen atoms of DTPA; or they can have three substituents (the same or different from each other) in $\alpha$ to the carboxyl groups of three acetic groups respectively bound to the three nitrogen atoms of DTPA.

Therefore, the compounds of the present invention are characterized in having some sterical hindrance, due to the presence of two or three substituents at the above mentioned positions. The minimum size of the substituents is that of a chain having at least three carbon atoms.

Said hindering groups are probably responsible for the interactions of the paramagnetic chelates with biological components of the fluids in which the agent diffuses, said interactions substantially consisting in the formation of strong non-covalent bonds with the proteins present in such fluids. In particular said tight bonding is detectable in plasma, showing a great affinity of the compounds of the invention with the plasma proteins. This feature is particularly unexpected in view of the general teaching of the art. Actually it is well known that when a compound is hepatospecific, it is preferentially/selectively taken up by the liver hepatocytes and then it is excreted via the biliary route, in such way being cleared from the palsma. The compounds of the present invention, on the contrary, showed such an affinity with the plasma proteins to give extremely high values of relaxivity in serum (thus confirming the formation of strong bonds with serum proteins). Accordingly one of their preferential and strongly recommended use is as potential blood pool contrast agents, said caracteristic feature giving the possibility of a long period of permanence inside the vessels even administering substantially lower doses.

Relaxivity values of the contrast agent of the present invention have been tested either in saline or in human serum obtained by Seronorm™ Human, freeze-dried human serum produced by Nycomed Pharma AS, Oslo, Norway. Serum obtained from said Seronorm™ is substantially equivalent to the fresh one, so its use in the relaxivity determination grants a good picture of the "in vivo" behaviour and, further, an excellent reproducibility of this test.

The compounds object of the present invention are characterised by very high $r_1$ and $r_2$ relaxivity values. When measured in Seronorm™ Human at 20 MHz, at a temperature of 39° C., and at a concentration comprised from 0 to 1 mM, the compounds of the present invention have $r_1$ relaxivity equal to or, preferably, higher than 15 $s^{-1}mm^{-1}$.

DETAILED DISCLOSURE OF THE INVENTION

The present invention relates to novel chelating agents, more particularly linear aminopolycarboxylic acid derivatives chelants, and metal chelates thereof and the use of such chelating agents and chelates in the preparation of diagnostic imaging contrast agents and in particular of contrast agents exhibiting improved serum relaxivity.

Said compounds are polyaminopolycarboxylic acid derivatives of formula (I), either in their racemic or enantiomeric forms:

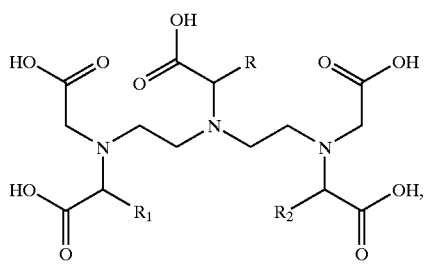

(I)

wherein:
R is H or a linear or branched, saturated or unsaturated $C_1$–$C_{20}$ alkyl chain, which is interrupted or not by one or more O, N, S atoms or by one or more —CO—, —CH(OH)—, —CH(NH$_2$)—, —CONH—, —NHCO—, —SO—, —SO$_2$—, —SO$_2$NH—, which is substituted or not with one or more halogen atoms or —COOH groups or their ester or amide derivatives and which is interrupted or not or substituted or not by one or more cyclic $R_3$ residues which can be the same or different and isolated or fused, with the proviso that, if some of said residues are fused, the maximum number of rings forming the corresponding polycyclic unit is three, in which:

$R_3$ is a 5- or 6-membered carbocyclic or heterocyclic, saturated, unsaturated or aromatic cyclic unit, substituted or not with one or more groups X, which can be the same or different, in which:

X is OH, halogen, NH$_2$, NHL, N(L)$_2$, —O—L, —S—L, —CO—L, where L, the same or different from each other, is $C_1$–$C_5$ linear or branched alkyl, substituted or not with one or more hydroxy, alkoxy or carboxylic groups, or X is a COOH group or its ester or amide derivative, or a —SO$_3$H group or its amide derivative, and $R_1$, $R_2$ have the same meanings as R, independently from each other, except H, with the proviso that: when $R_1$ and $R_2$ are both $C_6H_5$—CH$_2$—O—CH$_2$—, R is different from either H or $C_6H_5$—CH$_2$—O—CH$_2$—.

The invention further relates to complexes of the ligand of formula (I) with metal ions of atomic number from 20 to 31, 39, from 42 to 44, 49 and from 57 to 83; particularly preferred metals being: $Fe^{(2+)}$, $Fe^{(3+)}$, $Cu^{(2+)}$, $Cr^{(3+)}$, $Gd^{(3+)}$, $Eu^{(3+)}$, $Dy^{(3+)}$, $La^{(3+)}$, $Yb^{(3+)}$, $Mn^{(2+)}$; as well as, where the metal chelate carries an overall charge, a salts thereof with a physiologically acceptable counterion, preferably selected from organic bases such as a primary, secondary or tertiary amines, a basic amino acid, or an inorganic base derived from an alkali metal or alkaline-earth metal cation such as: $Na^+$, $K^+$, $Mg^{2+}$, $Ca^{2+}$ or a mixture thereof.

The present invention further relates to the use of the compounds of formula (I) and of the salts of the complexes thereof as well as to the pharmaceutical formulations containing them for a diagnostic or therapeutic scope.

Preferred are the compounds of formula (I) in which R, $R_1$ and $R_2$ are selected from the following groups:

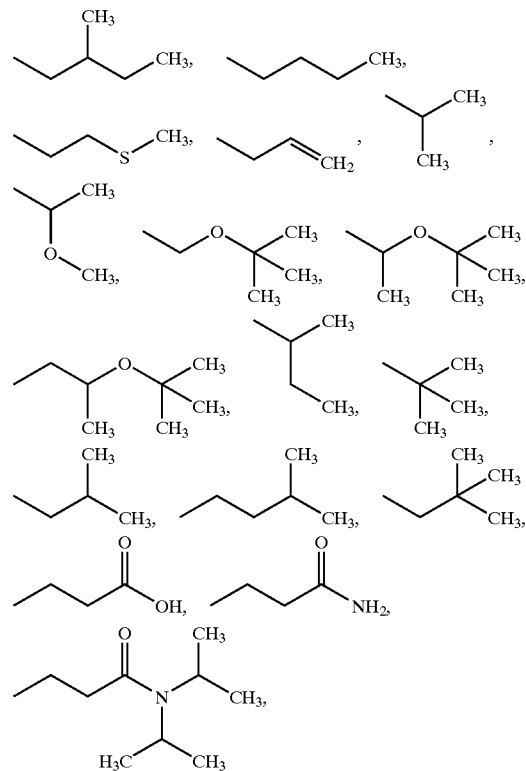

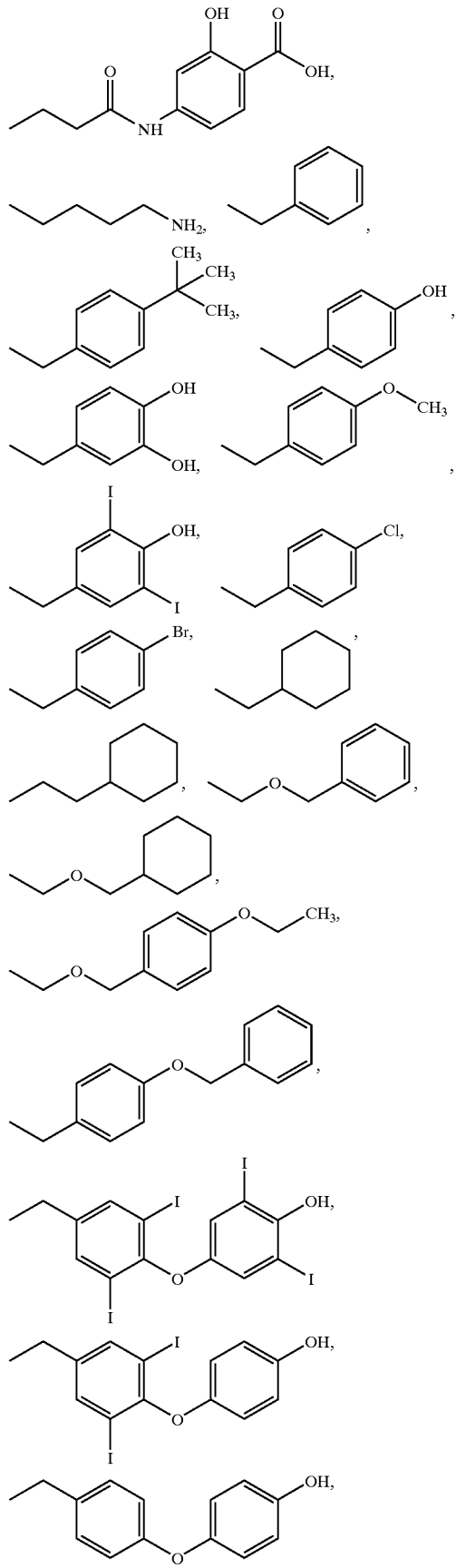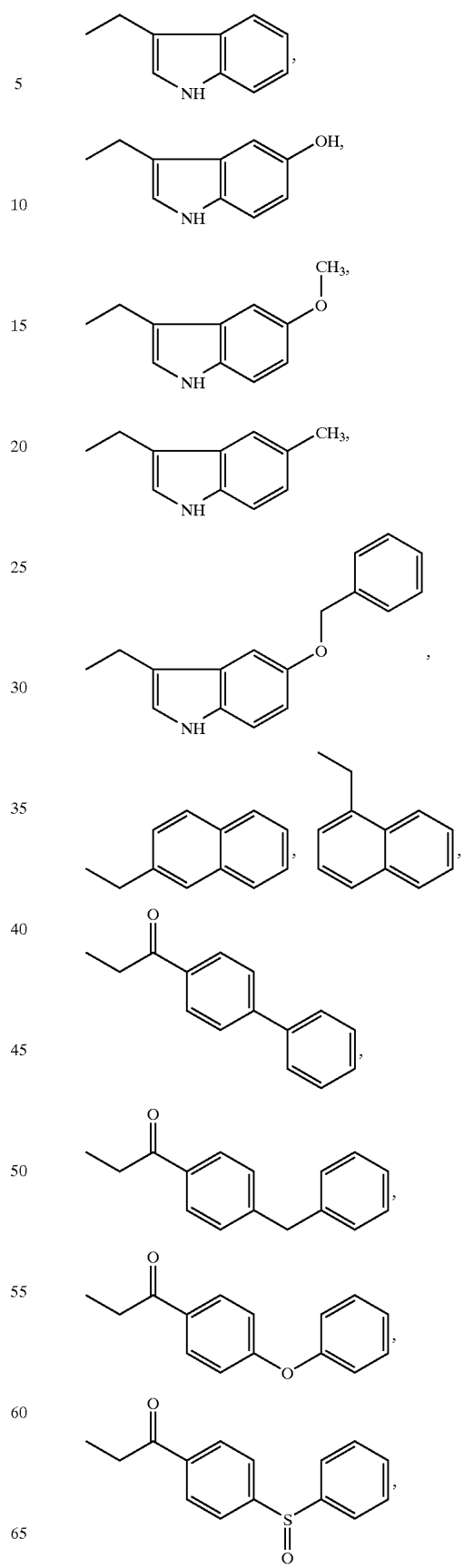

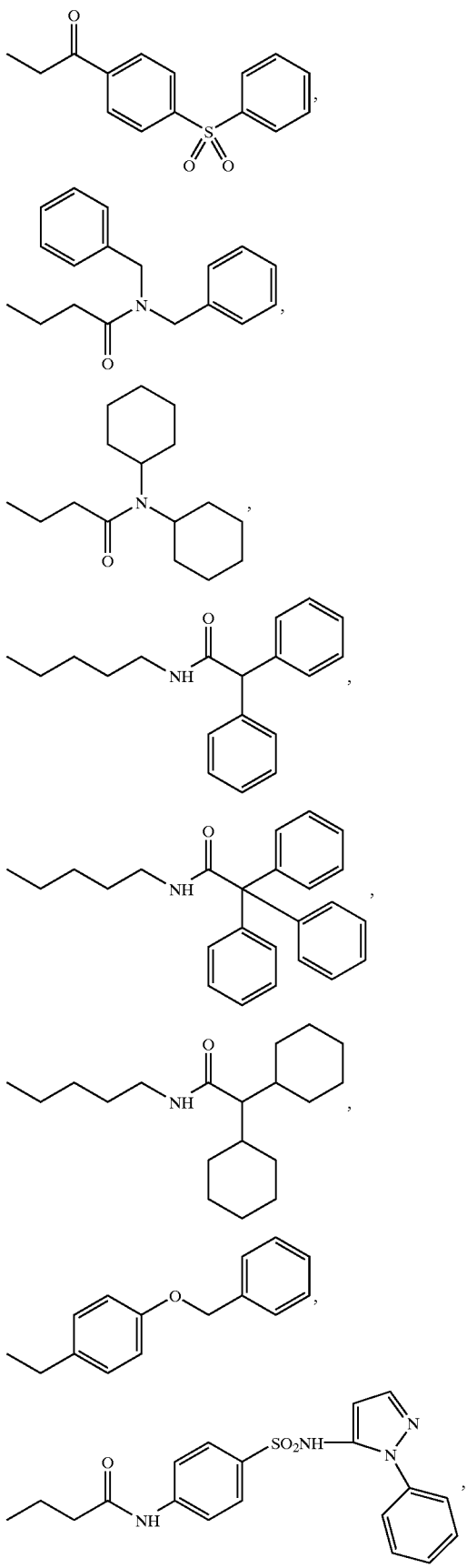
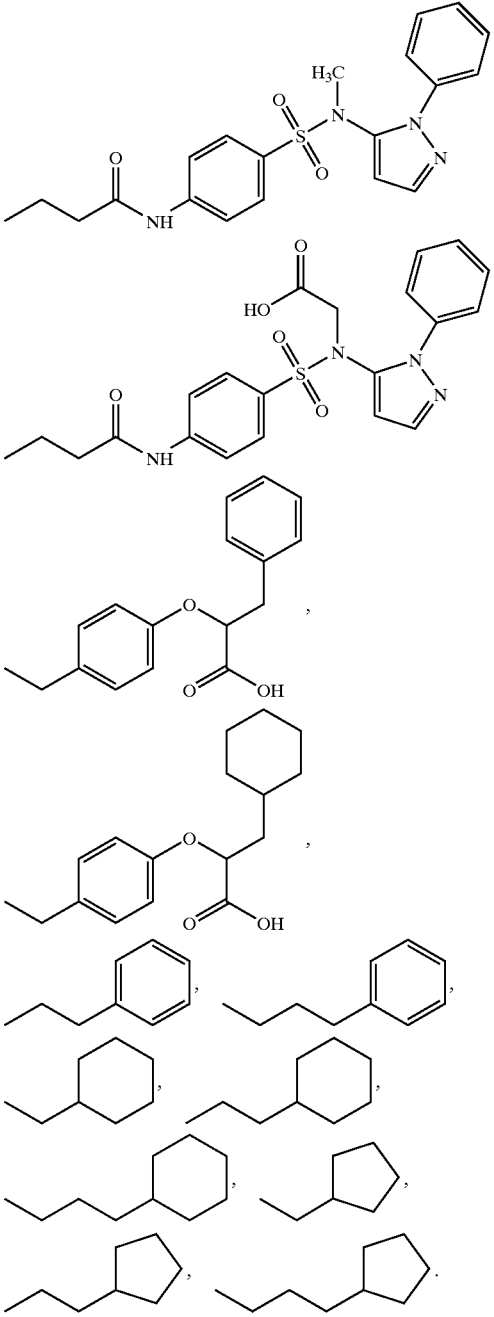
Among the compounds formula (I), particularly preferred are the compounds of formula (II):
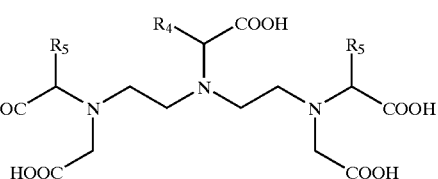
where:
R$_4$=H, or a linear or branched C$_1$–C$_{10}$ alkyl, optionally interrupted by one or more —CONH—, —NHCO—, —CO— groups and/or N, O, S atoms, optionally interrupted or substituted with 1 to 3 saturated rings, that are optionally interrupted by one or more N, O, S and that are optionally substituted with —OH, —SH, halogen, —COOH, —NH$_2$, —N(R")$_2$, —CON(R")$_2$, —SO$_3$H, C$_1$–C$_4$ alkoxy groups;

R$_5$=independently a linear or branched C$_1$–C$_{10}$ alkyl, optionally interrupted by one or more —CONH—, —NHCO—, —CO—groups and/or N, O, S atoms and interrupted or substituted with 1 to 3 saturated rings, that are optionally interrupted by one or more N, O, S and that are optionally substituted with —OH, —SH, halogen, —COOH, —NH$_2$, —N(R")$_2$, —CON(R")$_2$, —SO$_3$H, C$_1$–C$_4$ alkoxy groups;

R"=independently H or C$_1$–C$_5$ linear or branched alkyl, optionally substituted with from 1 to 5 —OH groups.

Equally preferred are the compounds of formula (III):

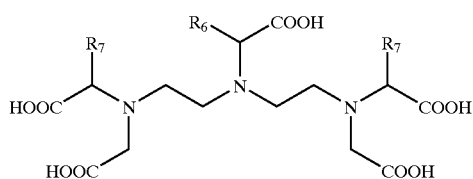

(III)

where:

R$_6$=H, or a linear or branched C$_1$—C$_{10}$ alkyl, optionally interrupted by one or more —CONH—, —NHCO—, —CO— groups and/or N, S atoms and optionally substituted with one or more —OH, —NH$_2$, —COOH groups;

R$_7$=independently a linear or branched C$_2$–C$_{10}$ alkyl, optionally interrupted by one or more —CONH—, —NHCO—, —CO— groups and/or N, S atoms and optionally substituted with one or more —OH, —NH$_2$, —COOH groups.

Equally preferred are the compounds of formula (IV):

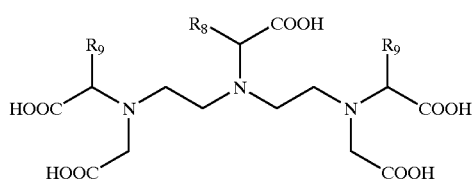

(IV)

where:

R$_8$=H, or a linear or branched C$_1$–C$_{10}$ alkyl, optionally interrupted by one or more —CONH—, —NHCO—, —CO— groups and/or N, S atoms, optionally interrupted or substituted with 1 to 3 isolated or fused saturated, unsaturated or aromatic rings, that are optionally interrupted by one or more N, O, S and that are optionally substituted with one or more —OH, —COOH, —NH$_2$, —N(R")$_2$ C$_1$–C$_6$ alkyl, C$_1$–C$_6$ alkoxy, C$_6$–C$_{20}$ arylalkoxy groups;

R$_9$=independently a linear or branched C$_1$–C$_6$ alkyl, optionally interrupted by one or more —CONH—, —NHCO—, —CO— groups and/or N, S atoms, which is interrupted or substituted with 2 to 3 fused saturated, unsaturated or aromatic rings, that are optionally interrupted by one or more N, O, S and that are optionally substituted with one or more —OH, —COOH, —NH$_2$, —N(R")$_2$, C$_1$–C$_6$ alkyl, C$_1$–C$_6$ alkoxy, C$_6$–C$_{20}$ arylalkoxy groups;

R"=independently H or C$_1$–C$_5$ linear or branched alkyl, optionally substituted with 1 to 5 —OH groups.

Equally preferred are the compounds of formula (V):

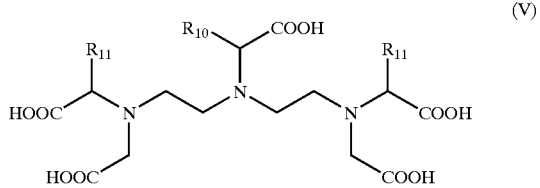

(V)

where:

R$_{10}$=a linear or branched C$_1$–C$_{10}$ alkyl, optionally interrupted by one or more —CONH—, —NHCO—, —CO— groups and/or N, S atoms, interrupted or substituted with 1 to 3 saturated, unsaturated or aromatic rings, that are optionally interrupted by one or more N, O, S and that are optionally substituted with one or more —OH, —COOH, —NH$_2$, —N(R")$_2$, C$_1$–C$_6$ alkyl, C$_1$–C$_6$ alkoxy groups;

R$_{11}$=independently a linear or branched C$_2$–C$_{10}$ alkyl, optionally interrupted by one or more N, S atoms.

Two further groups of preferred compounds, all included in compounds of formula (I), are the compounds of formula (VI)

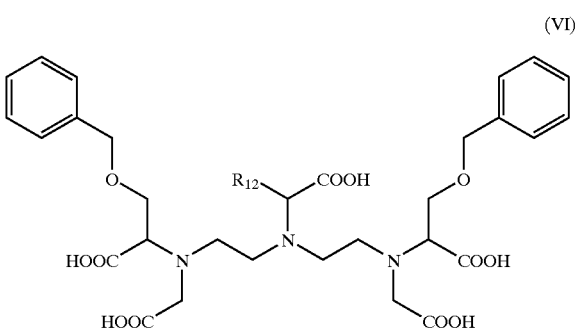

(VI)

where:

R$_{12}$=a linear or branched C$_2$–C$_{10}$ alkyl, optionally interrupted by one or more —CONH—, —NHCO—, —CO— groups and/or N, S atoms, optionally substituted with one or more —COOH, —NH$_2$ groups, optionally interrupted or substituted with 1 to 3 saturated, unsaturated or aromatic, isolated or fused rings, that are optionally interrupted by one or more N, O, S and that are optionally substituted with one or more —OH, —COOH, —NH$_2$, —N(R")$_2$, C$_1$–C$_6$ alkyl, C$_1$–C$_6$ alkoxy groups, and the compounds of formula(VII)

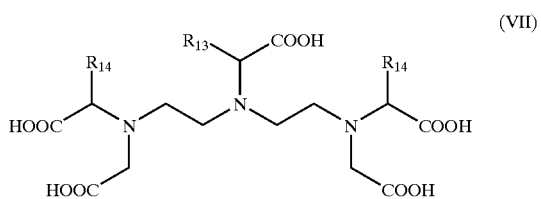

(VII)

where:

R$_{13}$=H, linear or branched C$_1$–C$_6$ alkyl, substituted or interrupted with 1 aromatic ring, that is optionally interrupted by one or more N, O, S;

R$_{14}$=independently linear or branched C$_1$–C$_6$ alkyl, substituted or interrupted with one aromatic ring, that is optionally interrupted by one or more N, O, S.

Also preferred among the compounds of the formula (I), are the compounds of formula (VIII):

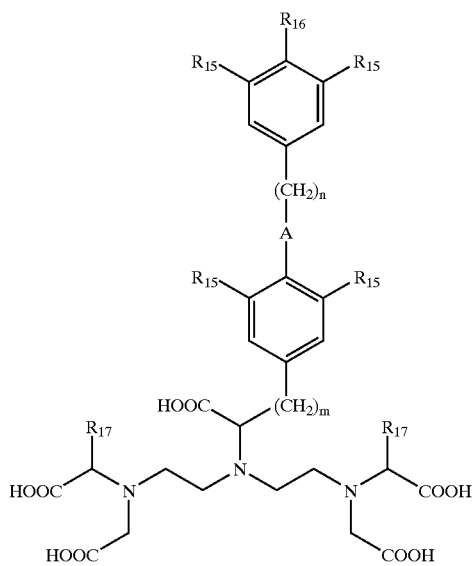

where:

$R_{15}$=independently H, halogen;

$R_{16}$=H, OH, N(R")$_2$, COOR", —CON(R")$_2$, —SO$_3$H, —SO$_2$NHR", C$_1$–C$_6$ alkyl, C$_1$–C$_6$ alkoxy;

$R_{17}$=independently C$_1$–C$_6$ alkyl, substituted with —COOH or —CON(R")$_2$ or from 1 to 3 —OH groups;

A=direct bond (i.e. no intervening atom), —O—, C=O m=integer 1–6;

n=integer 0–2;

R"=independently H or C$_1$–C$_5$ linear or branched alkyl, optionally substituted with 1 to 5 —OH groups with the proviso that, when $R_{16}$=H, at least one of the substituents $R_{15}$ is different from hydrogen.

Particularly preferred, among the various possible synthetic pathways yielding the compounds of the invention, is the following one, which is reported in the following Scheme 1 in order to further clarify the process:

SCHEME 1

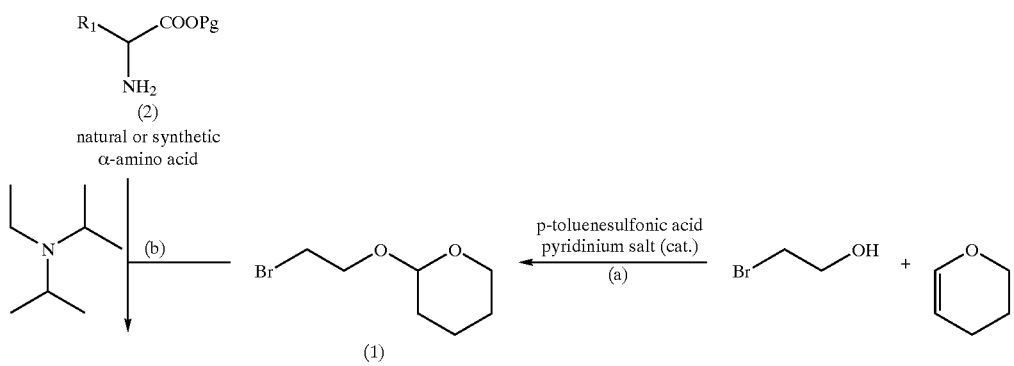

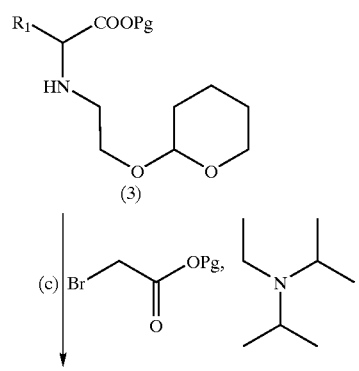

-continued

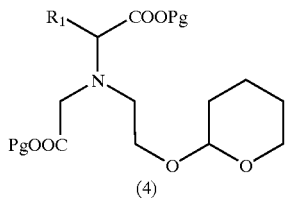 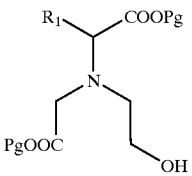

(4) → (5)

p-toluenesulfonic acid pyridinium salt (cat.)
EtOH/H₂O
(d)

(e) | N-bromosuccinimide
triphenylphosphine

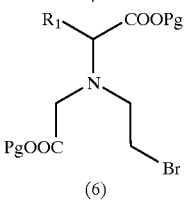

(6)

wherein Pg=protective group (such as t-butyl);

$R_1$ as defined for compounds of general formula (I).

Step (a) involves the protection of the alcohol group of 2-bromoethanol with dihydropyran to give intermediate (1). The reaction is carried out in an organic solvent such as $CH_2Cl_2$, $CHC_{13}$, $CH_2ClCH_2CL$, in the presence of 4-toluenesulfonic acid pyridinium salt or of other acid catalysts. In intermediate (1) the Br atom can be replaced with any other nucleofugal group (such as Cl, I, —OMs, —OTf, —OTs) and the alcohol-protecting group can be replaced, for example, by benzyl and trityl.

In step (b) the ester (for example the t-butyl ester) of a natural or synthetic α-amino acid (2), in the racemic or optically active form, is reacted with intermediate (1) in the presence of diisopropylethylamine in a solvent such as $CH_3CN$, DMF or a chlorinated solvent, to give intermediate (3).

The latter is reacted, in step (c), with a bromoacetic acid ester (such as t-butylbromoacetate) in the presence of diisopropylethylamine, to give intermediate (4), which is reacted, in the subsequent step (d), with 4-toluenesulfonic acid pyridinium salt, or other acid catalysts, in a water/ethanol mixture, at a temperature of 20–60° C., to give intermediate (5).

In step (e), intermediate (5) is brominated with N-bromosuccinimide in the presence of triphenylphosphine, to give compound (6).

With a similar procedure, compound (7) of formula

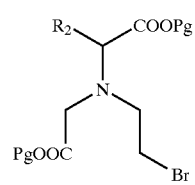

(7)

is prepared, wherein $R_2$ is as already defined for compounds of general formula (I).

The Br atom in intermediates (6) and (7) can be replaced with any other nucleofugal group (such as Cl, I, —OMs, —OTf, —OTs).

Intermediates (6) and (7) are then reacted, according to the following Scheme 2, to give the compounds of general formula (I).

SCHEME 2

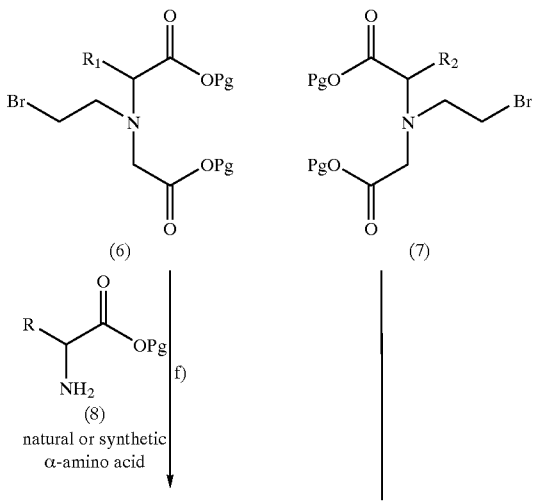

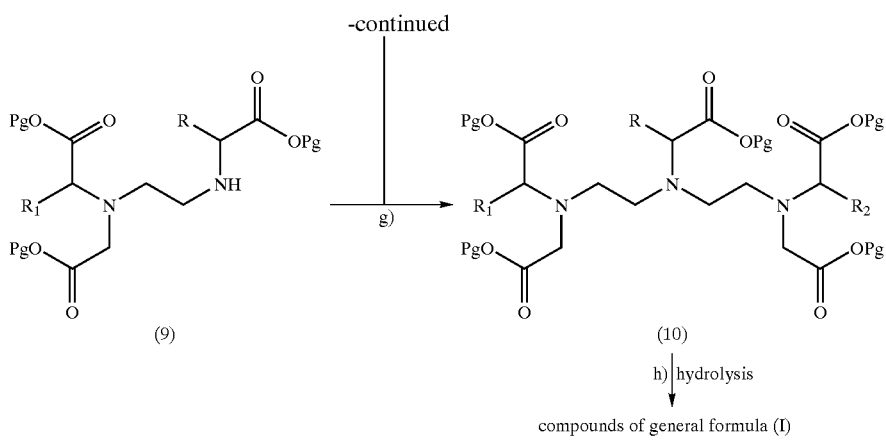

wherein R, $R_1$, $R_2$ are as already defined for compounds of general formula (I).

Step (f) involves the alkylation of the ester of a natural or synthetic α-amino acid (8) with bromoethyl-derivative (6) using double phase conditions in acetonitrile/aqueous phosphate buffer at pH 8 in a 1:1 molar ratio between the two reagents to give compound (9).

Intermediate (9) is further alkylated with the bromoethyl derivative (7), in step (g), in the same conditions, to give the intermediate pentaester (10), which is deprotected, in step (h), in conventional conditions, to give the corresponding pentaacid. When $R_1$ and $R_2$ are the same, the dialkylation product (10) can be obtained directly operating in acetonitrile/aqueous phosphate buffer at pH 8 and in a aminoester (8) to bromoderivative (6) molar ratio ranging from 1:2 to 1:3.

An alternative procedure for the preparation of intermediate (6), and similarly of intermediate (7), is illustrated in the following Scheme 3:

SCHEME 3

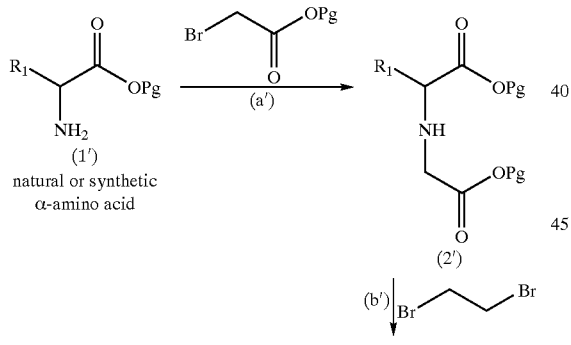

wherein:

Pg=protective group (such as t-butyl);

$R_1$ is above defined for compounds of general formula (I).

Step (a') involves the condensation of the ester of a natural or synthetic α-amino acid (2) with an α-haloacetic acid ester (2) (such as 2-bromoacetic acid t-butyl ester) in double phase conditions in acetonitrile/aqueous phosphate buffer at pH 8, to. give the iminodiacetic acid derivative (2'), which is alkylated, in step (b') in 1,2-dibromoethane as the solvent, under reflux, in the presence of N,N-diisopropylethylamine and at a temperature of about 80° C., to give intermediate (6).

TABLE 1

| | | Relaxivity (mM$^{-1}$s$^{-1}$) | | | |
| | | Saline (*) | | Serum (**) | |
| Compound | Structure | $r_1$ | $r_2$ | $r_1$ | $r_2$ |
|---|---|---|---|---|---|
| Gd-DTPA/Dimeg | [structure: Gd$^{3+}$·2MegH$^+$ complex with COO$^-$ groups] | 3.77 | 4.73 | 4.96 | 5.43 |

TABLE 1-continued

| Compound | Structure | Relaxivity (mM$^{-1}$s$^{-1}$) | | | |
| --- | --- | --- | --- | --- | --- |
| | | Saline (*) | | Serum (**) | |
| | | $r_1$ | $r_2$ | $r_1$ | $r_2$ |
| Gd-BOPTA$^{(\$)}$/Dimeg | [structure: Gd$^{3+}$·2MegH$^+$] | 4.39 | 5.56 | 10.8 | 12.2 |
| Gd-EOB-DTPA$^{(+)}$/Dimeg | [structure: 2MegH$^+$] | 5.43 | 6.15 | 11.00 | 12.6 |
| Compound 12 of Ex. 17 | [structure: Gd$^{3+}$·2MegH$^+$] | 5.84 | 6.71 | 37.33 | 44.7 |
| Compound 6 of Ex. 11 | [structure: Gd$^{3+}$·2MegH$^+$] | 6.61 | 7.5 | 38.0 | 46.2 |

TABLE 1-continued
| Compound | Structure | Relaxivity (mM⁻¹s⁻¹) | | | |
| --- | --- | --- | --- | --- | --- |
| | | Saline (*) | | Serum (**) | |
| | | $r_1$ | $r_2$ | $r_1$ | $r_2$ |
| Compound 7 of Ex. 12 | 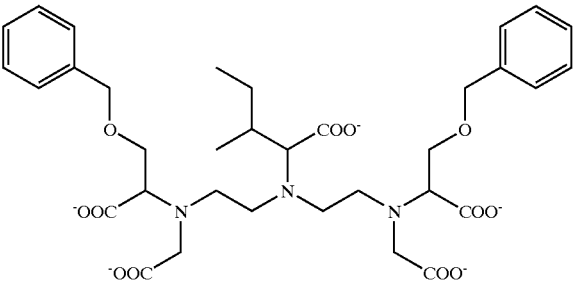 Gd³⁺·2MegH⁺ | 5.88 | 6.72 | 38.2 | 45.4 |
| Compound 4 of Ex. 9 | 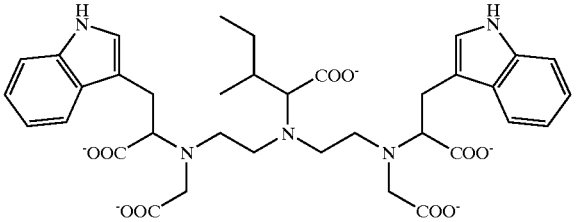 Gd³⁺ 2Na⁺ | 7.3 (*) | 8.4 (*) | 45.9 | 55.5 |
| Compound 3 of Ex. 8 | 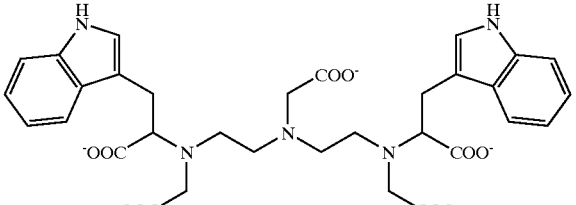 Gd³⁺ 2Na⁺ | 5.62 | 6.33 | 39.0 | 45.0 |
| Compound 2 of Ex. 7 | 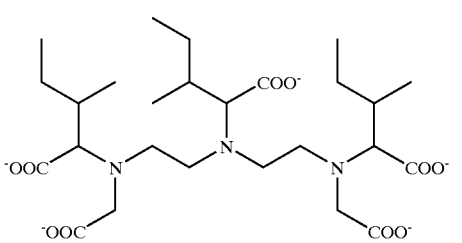 Gd³⁺·2Na⁺ | 5.07 | 5.82 | 11.9 | 13.4 |
| Compound 1 of Ex. 6 | 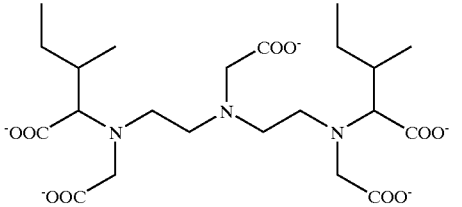 Gd³⁺·2Na⁺ | 4.55 | 5.11 | 9.5 | 10.7 |

TABLE 1-continued

| | | Relaxivity (mM⁻¹s⁻¹) | | | |
| | | Saline (*) | | Serum (**) | |
| Compound | Structure | $r_1$ | $r_2$ | $r_1$ | $r_2$ |
| --- | --- | --- | --- | --- | --- |
| Compound 5 of Ex. 10 | 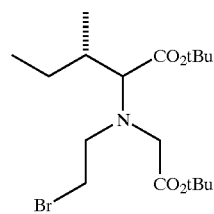 Gd³⁺·2Na⁺ | 5.83 | 6.75 | 21.5 | 25.0 |

(*) NaCl 0.15M in water - pH 7.3 - 20 MHz - 39° C.
(**) Between 0 and 1 mM (Seronorm ™ Human) - 20 MHz - 39° C.
(***) Between 0 and 2 mM
($)Bracco EP-B 230893
(+)Schering EP 405704

Table 1 above discloses the high relaxivity shown in serum by the compounds of the present invention; $r_1$ and $r_2$ relaxivity values of some of the preferred compounds are reported, in comparison with the corresponding $r_1$ and $r_2$ values measured for some of the mayor prior-art compounds: Gd-DTPA Dimeglumine salt (MAGNEVIST®); Gd-BOPTA Dimeglumine salt and Gd-EOB-DTPA Dimeglumine salt.

The data of Table 1 clearly show that the compounds of the present invention have surprisingly high relaxivity values $r_1$ and $r_2$, measured in Seronorm™ Human, thus confirming the formation of unexpectedly strong non-covalent bonds with serum proteins. The ralaxivity values measured in serum for the other compounds of the invention, in particular for compounds 13 and 14 of Examples 18 and 19, are of the same order of magnitude as the ones reported in Table 1.

This is particularly interesting from the application point of view, both as far as the improvement in the obtainable images, the development of formulations specific to blood pool use and the determination of optimum low dosages of the contrast medium are concerned.

EXAMPLE 1

Glycine 1,1-dimethylethyl ester

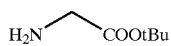

To a suspension of glycine (22.52 g; 0.3 mol) in t-butyl acetate (1200 mL; 9 mol), maintained at 20° C. under an inert atmosphere, HClO₄ 70% (35 mL; 0.41 mol) was added in 1 h. The reaction mixture was stirred at 20° C. for 18 h and monitored by TLC. The mixture was extracted with H₂O (1000 mL) and the aqueous phase, basified to pH 10 with solid Na₂CO₃, was extracted with CHCl₃ (1800 mL). The organic layer was dried over Na₂SO₄ and concentrated until constant weight to give the desired product (30.4 g; 0.23 mol). Yield 77%.

TLC: Rf 0.5

Stationary phase: silica gel plates 60 F₂₅₄

Eluent: 9:1 CH₂Cl₂/CH₃OH

Detection: 0.5% KMnO₄ in 1N NaOH

¹³C-NMR, ¹H-NMR, MS and IR spectra were consistent with the structure.

EXAMPLE 2

N-(2-Bromoethyl)-N-[2-(1,1-dimethylethoxy)-2-oxoethyl]-L-isoleucine 1,1-dimethylethyl ester

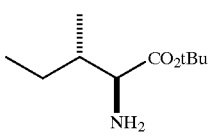

A) L-isoleucine 1,1-dimethylethylester

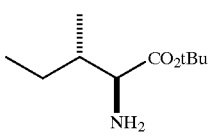

To an ice-bath cooled slurry of L-isoleucine (301.0 g; 2.29 mol) in tert-butyl acetate (2.5 L), 70% aq HClO₄ (208 mL, 2.43 mol) was slowly added. The mixture was kept stirring for 10 days at room temperature. Then water (0.5 L) was poured into, followed by cooling in an ice bath and addition of NaOH pellets (100 g) and Na$_2$CO$_3$ (110 g) so that pH turned to basic. The mixture was extracted with EtOAc (4×0.5 L); the combined organic phases were washed with water (2×0.5 L) and brine (0.3 L), at last dried over Na$_2$SO$_4$. After careful removal of solvents in vacuo, the desired compound was obtained (262.2 g; 1.40 mol) and stored at −18° C. No further purification was required on the basis of TLC and NMR data. Yield 61%.

TLC: R$_f$ 0.8

Stationary phase: silica gel.

Eluent: CH$_3$Cl/CH$_3$OH/25% (w/w) NH$_4$OH 90:9:1.

Detection: 0.2% ninhydrine (w/v) in EtOH.

$^1$H-NMR, $^{13}$C-NMR, MS and IR spectra were consistent with the structure.

B) (2-Bromoethoxy)(1,1-dimethylethyl)dimethylsilane

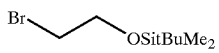

This product is commercially available (Aldrich art. 42,842–6).

C) N-[2-(1,1-Dimethylethoxy)-2-oxoethyl]-N-[2-[[(1,1-dimethylethyl) dimethylsilyl]oxy]ethyl]-L-isoleucine 1,1-dimethylethyl ester

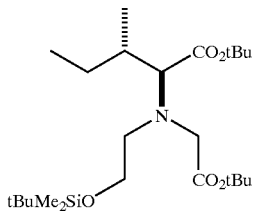

L-isoleucine 1,1-dimethylethylester (23.00 g; 122.8 mmol), (2-Bromoethoxy)-(1,1-dimethylethyl) dimethylsilane (30.26 g, 126.5 mmol) and Na$_2$CO$_3$ (26.18 g; 247.0 mmol) were stirred in DMPU (Aldrich art. 25,156–9) (300 mL) at 90° C. for 20 h. The intermediate product was not isolated, but after cooling the mixture to roughly 40° C., tert-butyl bromoacetate (commercial product) (19.0 mL; 130 mmol) and further Na$_2$CO$_3$ (27.00 g; 254.7 mmol) were added, then heating at 90° C. was restored. More tert-butyl bromoacetate (2.0 mL; 14 mmol) was added after 4 h and heating prolonged for another 2 h. The mixture was cooled to 0° C., then water (600 mL) was cautiously added (exothermic solubilization). Once clear, the solution was extracted with diethyl ether (4×250 mL); the combined organic layers were washed with water (3×250 mL), brine (250 mL), at last dried over Na$_2$SO$_4$. After removal of solvents in vacuo, the residual oil was purified by flash chromatography (n-hexane/iPr$_2$O 95:5). The desired compound was obtained (42.25 g; 91.90 mmol). Yield 75%.

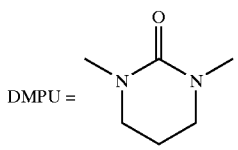

TLC: R$_f$ 0.75

Stationary phase: silica gel.

Eluent: n-hexane/Et$_2$O 8:2 (v/v).

Detection: 254 nm; I$_2$; 0.5% KMnO$_4$ in 1 N NaOH;2% (w/v) Ce(SO$_4$)$_2$.4H$_2$O, 4.2% (w/v) (NH$_4$)$_6$Mo$_7$O$_{24}$, 6% (w/v) H$_2$SO$_4$ in water (Pancaldi).

$^1$H-NMR, $^{13}$C-NMR, MS and IR spectra were consistent with the structure.

D) N-[2-(1,1-Dimethylethoxy)-2-oxoethyl]-N-(2-hydroxyethyl)-L-isoleucine 1,1-dimethylethyl ester

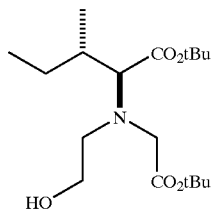

In a solution of the compound obtained in the previous step (33.57 g; 73.02 mmol) in freshly dried THF (200 mL, distilled over sodium/benzophenone) cooled at −10° C. under a nitrogen atmosphere, a 1 M solution of nBu$_4$NF in THF (110 mL; 110 mmol) was slowly dropped. The stirred solution was allowed to rise to room temperature throughout 5 h. The solvent was then removed on a rotavapor, the residue taken up in diethyl ether (400 mL), and the solution washed with water (100 mL), saturated NH$_4$HCO$_3$ (200 mL), water (100 mL), brine (100 mL). After prolonged evaporation in vacuo (250 Pa) a thick oil was obtained (28.71 g): the crude product was deemed pure enough for the following derivatization.

TLC: R$_f$ 0.5

Stationary phase: silica gel.

Eluent: n-hexane/EtOAc 85:15 (v/v).

Detection: 254 nm; I$_2$; 0.5% KMnO$_4$ in 1 N NaOH; 1% (w/v) vanilline in 96% (w/v) H$_2$SO$_4$/abs EtOH 4:1 (v/v).

$^1$H-NMR, 13C-NMR, MS and IR spectra were consistent with the structure.

E) N-(2-Bromoethyl)-N-[2-(1,1-dimethylethoxy)-2-oxoethyl]-L-isoleucine 1,1-dimethylethyl ester To a solution of the crude product obtained from the previous preparation (73 mmol approximately) and triphenylphosphine (20.31 g; 77.43 mmol) in CH$_2$Cl$_2$ (0.5 L, freshly distilled over CaH$_2$) under a nitrogen atmosphere, N-bromosuccinimide (>98%; 13.80 g) was portionwise added throughout 1 h at 0° C. The reaction was left stirring overnight and allowed to rise gradually to room temperature. Most of the solvent was evaporated, diethyl ether and n-hexane were added in sequence, enabling the bulk of Ph$_3$PO to precipitate as a filterable solid. The remaining solution was concentrated in the presence of silica gel and submitted to a flash chromatography (n-hexane/iPr$_2$O 91:9). The desired compound was isolated (21.22 g; 51.96 mmol). Yield over the last two steps: 71%.

TLC: R$_f$ 0.5

Stationary phase: silica gel.

Eluent: n-hexane/iPr$_2$O 9:1 (v/v).

Detection: 254 nm; I$_2$; 0.5% KMnO$_4$ in 1 N NaOH.

$^1$H-NMR, $^{13}$C-NMR, MS and IR spectra were consistent with the structure.

EXAMPLE 3

N-(2-Bromoethyl)-N-[2-(1,1-dimethylethoxy)-2-oxoethyl]-L-phenylalanine 1,1-dimethylethyl ester

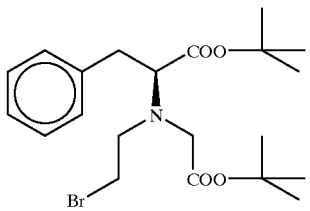

A) L-phenylalanine 1,1-dimethylethyl ester

98% $H_2SO_4$ (7 mL; 0.13 mol) was dripped over 20 min into dioxane (70 mL), maintaining the temperature of the solution below 20° C. After addition of L-phenylalanine (commercial product) (16.5 g; 0.10 mol), the solution was stirred over 12 h at 132 kPa under an isobutene (commercial product) atmosphere (consumed isobutene 45 g; 0.80 mol). The solution was dropped into a mixture of ice (200 g) and 10 N NaOH (30 mL, 0.30 mol) and extracted with $Et_2O$ (1 L). After washing with $H_2O$ (150 mL), the organic phase was dried over $Na_2SO_4$ and evaporated in vacuo. The residue was distilled to give L-phenylalanine 1,1-dimethylethyl ester (13 g; 0.059 mol). Yield 59%.

bp: 85–90° C. at 5.3 Pa
Acidic titer (0.1 N HCl): 99.7%; equivalent point pH 4.77
HPLC: 98% (area %)—Chromatographic method:
Stationary phase: Lichrosorb RP-Select B 5 mm;
250×4 mm column packed by Merck KGaA;
Temperature: 45° C.;
Mobile phase: gradient elution;
A=0.01 M $KH_2PO4$ and 0.017 M $H_3PO_4$ in water
B=$CH_3CN$

| Gradient timetable: | min | % A | % B |
|---|---|---|---|
| | 0 | 95 | 5 |
| | 30 | 20 | 80 |
| | 45 | 20 | 80 |

Flow rate: 1 mL min$^{-1}$;
Detection (UV): 210 nm, 280 nm;
Injection: 10 μL;
Sample concentration: 1 mg mL$^{-1}$;
Instrumentation: Merck KGaA—Hitachi high pressure gradient pump system (two Lachrom L 7100 pumps), Merck KGaA—Hitachi Lachrom L 7200 autosampler, Merck KGaA—Hitachi Lachrom L 7300 column thermostat, Merck KGA—Hitachi Lachrom L 7400 UV detector.
K.F.: <0.1%
$^1$H-NMR, $^{13}$C-NMR, MS and IR spectra were consistent with the structure.
$[\alpha]_D^{20}$: +16.64° (c 5.29, $CHCl_3$)
Elemental analysis (%):

| | C | H | N |
|---|---|---|---|
| Calcd. | 70.56 | 8.65 | 6.33 |
| Found | 71.21 | 8.89 | 6.61 |

B) N-[2-(1,1-Dimethylethoxy)-2-oxoethyl]-N-(2-hydroxyethyl)-L-phenylalanine 1,1-dimethylethyl ester A solution of L-phenylalanine 1,1-dimethylethyl ester (221.3 g; 1 mol), 2-(2-bromoethoxy)-tetra-hydropyran, prepared according to J. Org. Chem. 1986, 51, 752–755 (282.3 9; 1.35 mol) and diisopropylethylamine (commercial product) (175 mL; 1 mol) in $CH_3CN$ (1 L) was refluxed for 14 h. Diisopropylethylamine (commercial product) (175 mL; 1 mol) and tert-butyl bromoacetate (commercial product) (233 g; 1.2 mol) were added and the mixture refluxed for further 2 h. The solution was evaporated to give a residue which was dissolved in n-hexane (2 L) and washed with $H_2O$ (1,4L), 1 N HCl (500 mL), 1 N NaOH (100 mL) and $H_2O$ (200 mL). The solution was evaporated and the residue was dissolved in MeOH (2 L) and 2 N HCl (1 L) was added. After 2 h, 2 N NaOH (1.2 L) was added, the solution was evaporated to remove methanol and n-hexane (2 L) was added to extract the product. The organic solution was evaporated to obtain the desired product (280 g; 0.738 mol). The product was utilised for the following step without further purification.

Yield 74%.
HPLC: 91% (area %)—Chromatographic method of previous step A).
$[\alpha]_D^{20}$: +17.13° (c 5.08, $CHCl_3$)

In another preparation the compound was purified by flash chromatography: Stationary phase: Silica gel 230–400 mesh Merck KGaA art 9385
Eluent: 4:1 n-hexane/EtOAc
to give N-[2-(1,1-dimethylethoxy)-2-oxoethyl]-N-(2-hydroxyethyl)-L-phenylalanine 1,1-dimethylethyl ester for the analytical characterisation.
Acidic titer (0.1 N $HClO_4$): 98.6%
HPLC: 97.4% (area %) Chromatographic method of previous step A).
K.F.: <0.10%
$^1$H-NMR, $^{13}$C-NMR, MS and IR spectra were consistent with the structure.
$[\alpha]_D^{20}$: −19.89° (c 5.01, $CHCl_3$)
Elemental analysis

| | C | H | N |
|---|---|---|---|
| Calcd. | 66.46 | 8.76 | 3.69 |
| Found | 66.13 | 9.32 | 3.68 |

C) N-(2-Bromoethyl)-N-[2-(1,1-dimethylethoxy)-2-oxoethyl]-L-phenylalanine 1,1-dimethylethyl ester N-Bromosuccinimide (46.3 g; 0.26 mol) was added in portions to a solution of the product obtained in the previous step (75.9 g; 0.20 mol) and triphenylphosphine (68.1 g; 0.26 mol) in $CH_2Cl_2$ (500 mL) cooled at 0 5° C. and stirred. The solution was allowed to rise to r.t. and, after 4 h, was washed with $H_2O$ (400 mL), 5% aq. $NaHCO_3$ (200 mL) and $H_2O$ (100 mL). After drying ($Na_2SO_4$) the solution was evaporated and the residue was suspended in $Et_2O$ (1 L); the solid (triphenylphosphine oxide) was filtered and the solution evaporated. The residue was dissolved in n-hexane (500 mL), Carbopuron 4N (commercial product) (4 g) was added and filtered after stirring for a while. The solution was evaporated to give a residue (77 g) that was purified by flash chromatography (Stationary phase: Silica gel 230–400 mesh Merck KGaA art. 9385 (1 kg); Eluent: $Et_2O$) to afford the desired compound (68 g; 0.154 mol). Yield 77%.
TLC: Rf 0.46
Stationary phase: Silica gel plates 60 $F_{254}$ (Merck KGaA code 5715)

Eluent: n-hexane/EtOAc 4:1
Detection: 1% KMnO₄ in 1N NaOH
HPLC: 92% (area %)—Chromatographic method of previous step A).

EXAMPLE 4

N-(2-Bromoethyl)-N-[2-(1,1-dimethylethoxy)-2-oxoethyl]-L-tryptophan 1,1-dimethylethyl ester

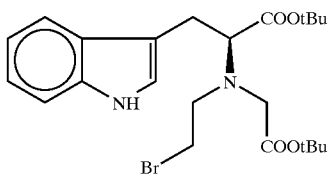

A) N -[(Phenylmethoxy)carbonyl]-L-tryptophan

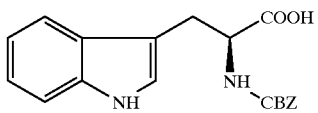

To a suspension of tryptophan (20.08 g; 98.32 mmol) in H₂O, cooled to 0° C., was added 1N NaOH (98 mL; 98 mmol) and the solution became clear. Maintaining the temperature at 0° C., 1N NaOH (108 mL; 108 mmol) and benzyl chloroformate (CBZCl, commercial product) (15.38 mL; 107.7 mmol) were simultaneously dropped in the reaction mixture. After the addition the mixture was kept at 0° C. for 30 min and then allowed to rise to r. t. The reaction was monitored by HPLC (Chromatographic method of Example 3, A). After further 3 h the pH was corrected to 9.5 by addition of 1N NaOH and the mixture was washed with Et₂O (200 mL). The aqueous layer was acidified to pH 2 using 2N HCl and the precipitate was filtered through a G3 septum, washed with cold water (2× 200 mL) and dried over P₂O₅ under vacuum (2 kPa). N-[(Phenylmethoxy)carbonyl]-L-tryptophan (33.96 g) was obtained and used in the following step without further purification.

m.p.: 230° C.
TLC: Rf 0.60
Stationary phase: silica gel plates 60 F₂₅₄
Eluent 9:1:0.1 CHCl₃/MeOH/AcOH
Detection: 254 nm; 0.5% KMnO₄ in 1N NaOH
HPLC: 95.6% Chromatographic method of Example 3, A).
$^{13}$C-NMR, $^{1}$H-NMR and MS spectra were consistent with the structure.

B) N-[(Phenylmethoxy)carbonyl]-L-tryptophan 1,1-dimethylethyl ester

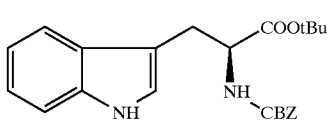

Into a suspension of N-[(phenylmethoxy)carbonyl]-L-tryptophan (33.27 g; 98.32 mmol), benzyltriethylammonium chloride (BTEAC) (22.4 g; 98.32 mmol) and K₂CO₃ (176.91 g; 1.28 mol) in dimethylacetamide (750 mL), tert-butyl bromide (265 mL; 2.36 mol) was dropped. The solution was heated to 550° C. and maintained under vigorous stirring for 19 h. The reaction was monitored by HPLC (Chromatographic method of Example 3, A)). The solution was cooled to r.t., diluted with H₂O (3 L) and then extracted with EtOAc (2 L). The organic layer was washed with H₂O (2 L) and, after elimination of the solvent, N-[(phenylmethoxy)carbonyl]-L-tryptophan 1,1-dimethylethyl ester (36 g) was obtained and used in the following step without further purification.

TLC: Rf 0.44
Stationary phase: silica gel plates 60 F₂₅₄
Eluent 7:3 n-hexane/EtOAc
Detection: 254 nm; 0.5% KMnO₄ in 1N NaOH
HPLC: 99% (area %) Chromatographic method of Example 3, A).
$^{13}$C-NMR, $^{1}$H-NMR and MS spectra were consistent with the structure.

C) L-Tryptophan 1,1-dimethylethyl ester

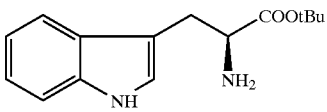

To a solution of N-[(phenylmethoxy)carbonyl]-L-tryptophan 1,1-dimethylethyl ester (36 g; 98 mmol) in EtOH (150 mL) Pd/C 10% (5 g) was added. A H₂ atmosphere was set and hydrogenation was performed with the aid of a Venturi type stirrer. Reaction conversion was estimated by HPLC (Chromatographic method L/46). After 6 h at r.t. the suspension was filtered through paper, then through Millipore® HA 0.45 µm and the filtrate was concentrated under reduced pressure to give a crude oil. The crude was dissolved in CHCl₃ (200 mL) and washed with 5% aq. Na₂CO₃ (200 mL) and brine (150 mL). The organic layer was dried over Na₂SO₄ and concentrated to give L-tryptophan-1,1-dimethylethyl ester (18.16 g), which was used in the following step without further purification.

HPLC: 97% (area %) Chromatographic method of Example 3, A).
$^{13}$C-NMR, $^{1}$H-NMR and MS spectra were consistent with the structure.

D) N-[2-(1,1-Dimethylethoxy)-2-oxoethyl]-L-tryptophan 1,1-dimethylethyl ester

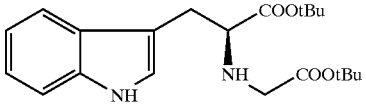

To a solution of L-tryptophan 1,1-dimethylethyl ester (17.10 g; 65.68 mmol) in CH₃CN (150 mL) 2M phosphate. buffer (pH 8; 150 mL) was added. Tert-butyl bromoacetate (10.7 mL; 72.25 mmol) was dropped into the mixture and vigorous mechanical stirring set on. The reaction was monitored by HPLC (Chromatographic method of Example 3, A)). After 23 h the organic layer was separated and concentrated to dryness to give a crude oil (26.62 g), which was purified by flash chromatography (silica gel; n-hexane/ethyl acetate, 8:2 v/v) to give the desired product (20.07 g; 53.59 mmol). Yield 54.5% starting from L-tryptophan.

TLC: Rf 0.28
Stationary phase: silica gel plates 60 F₂₅₄
Eluent 7:3 n-hexane/EtOAc
Detection: 254 nm; 0.5% KMnO₄ in 1N NaOH
HPLC: 100% Chromatographic method of Example 3, A).
$^{13}$C-NMR, $^{1}$H-NMR and MS spectra were consistent with the structure.

E) N-[2-(1,1-Dimethylethoxy)-2-oxoethyl]-N-(2-hydroxyethyl)-L-tryptophan 1,1-dimethylethyl ester

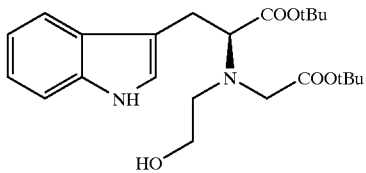

In a four-necked flask cooled to −80° C. equipped with a mechanical stirrer, a thermometer, and a jacketed dropping funnel N-[2-(1,1-dimethylethoxy)-2-oxoethyl]-L-tryptophan 1,1-dimethylethyl ester (5 g; 13.35 mmol) was dissolved in CH$_3$CN (25 mL). In the dropping funnel, cooled at −80° C., ethylene oxide (13 mL; 0.26 mol) was collected from the cylinder and then quickly dropped into the solution. Solid ytterbium triflate (0.83 g; 1.34 mmol) was added and after removal of the cooling bath the temperature was allowed to rise to r.t. The reaction was monitored by HPLC (Chromatographic method of Example 3, A)). After 15 h the solution was diluted with H$_2$O (50 mL) and extracted with Et$_2$O (150 mL). After evaporation of the solvent the crude was purified by flash chromatography (silica gel; n-hexane/ethyl acetate, 7:3 v/v) giving the desired product (4.32 g; 10.32 mmol).
Yield 77%.
TLC: Rf 0.23
Stationary phase: silica gel plates 60 F$_{254}$
Eluent 7:3 n-hexane/EtOAc
Detection: 254 nm; 0.5% KMnO$_4$ in 1N NaOH
HPLC: 99% (area %) Chromatographic method of Example 3, A).
$^{13}$C-NMR, $^1$H-NMR and MS spectra were consistent with the structure.

F) N-(2-Bromoethyl)-N-[2-(1,1-dimethylethoxy)-2oxoethyl]-L-tryptophan 1,1-dimethylethyl ester

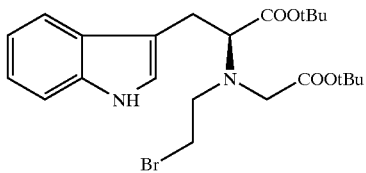

To a solution of N-[2-(1,1-dimethylethoxy)-2-oxoethyl]-N-(2-hydroxyethyl)-L-tryptophan 1,1-dimethyl-ethyl ester (4.64 g; 11.09 mmol) in CH$_2$Cl$_2$ (44 mL; freshly distilled over CaH$_2$) under an inert atmosphere, solid Ph$_3$P (2.9 g; 11.09 mmol) was added. The solution was cooled to 0° C. and then solid NBS (1.97 g; 11.09 mmol) was portionwise added (45 min), waiting for complete dissolution after each addition. The reaction was monitored by TLC:
1. Stationary phase: silica gel plates 60 F$_{254}$
   Eluent 7:3 n-hexane/EtOAc
   Detection: 254 nm; 0.5% KMnO$_4$ in 1N NaOH
2. Stationary phase: silica gel plates 60 F$_{254}$
   Eluent 8:2 n-hexane/EtOAc
   Detection: 254 nm; 0.5% KMnO4 in 1N NaOH After 3 h at 0° C. and 1 h at r.t. the mixture was concentrated until a white solid started to precipitate and the cloudy solution was left on standing at 4° C. for 72 h. The white precipitate (Ph$_3$PO) was filtered off and the clear solution concentrated. The crude was purified by flash chromatography (silica gel; n-hexane/ethyl acetate, 8:2 v/v) to give the desired product (4.46 g; 9.26 mmol). Yield 83%.

TLC: Rf 0.42
Stationary phase: silica gel plates 60 F$_{254}$
Eluent 8:2 n-hexane/EtOAc
Detection: 254 nm; 0.5% KMnO$_4$ in 1N NaOH
HPLC: 94% (area %) Chromatographic method of Example 3, A).
$^{13}$C-NMR, $^1$H-NMR and MS spectra were consistent with the structure.

EXAMPLE 5

N-(2-Bromoethyl)-N-[2-(1,1-dimethylethoxy)-2-oxoethyl]-O-(phenylmethyl)-L-serine 1,1-dimethylethyl ester

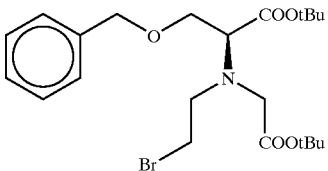

A) 2-(2-Bromoethoxy)tetrahydropyran
This compound has been prepared according to: J. Org. Chem. 1986, 51, 752–755.

B) O-Phenylmethyl-L-serine 1,1-dimethylethylester
To a suspension of O-phenylmethyl-L-serine (50 g; 0.26 mol) in t-butyl acetate (1000 mL; 7.49 mol) 70% perchloric acid was added (50 mL; 0.58 mol). The solution was maintained under stirring for 72 h at 250° C. under inert atmosphere. The reaction mixture was diluted with Et$_2$O (300 mL), then a 10% Na$_2$CO$_3$ aqueous solution was slowly added until pH 9 was reached. The organic layer was separated, dried over Na$_2$SO$_4$ and concentrated. The residual t-butyl acetate was distilled under reduced pressure (40° C.0.1 mm Hg). The desired product was obtained (54.2 g; 0.21 mol). Yield 83%.
TLC: Rf 0.4
Stationary phase: silica gel
Eluent: CHCl$_3$: CH$_3$OH=9.5:0.5 (v/v)
$^{13}$C-NMR, $^1$H-NMR and MS spectra were consistent with the structure.
$[\alpha]_D^{20}$: −9,08° (c 5.0; CHCl$_3$)

C) N-(2-Hydroxyethyl)-N-[2-(1,1-dimethylethoxy)-2-oxoethyl]-O-(phenylmethyl)-L-serine 1,1-dimethylethyl ester

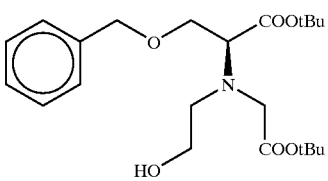

A solution of O-phenylmethyl-L-serine 1,1-dimethylethylester (251 g; 1 mol), 2-(2-bromoethoxy)tetrahydropyran (244 g; 1.1 mol) and diisopropylethylamine (commercial product) (155 g; 1.2 mol) in CH$_3$CN (1 L) was refluxed for 14 h. Diisopropylethylamine (commercial product) (193 g; 1.5 mol) and tert-butyl bromoacetate (234 g; 1.2 mol) were added and the mixture refluxed for further 2 h. The solution was evaporated and the residue was dissolved in CH$_2$Cl$_2$ (2 L) and washed with H$_2$O (3 L). The solution was evaporated and the residue (650 g) dissolved in 90% EtOH (2 L)4-toluenesulfonic acid pyridinium salt (obtained by salification of 4-toluenesulfonic acid with pyridine in diethyl ether, filtration of the precipitate and drying) (30 g; 0.12 mol) was added and the solution heated at 550° C. for 45 h. The solution was evaporated, the residue dissolved in $CH_2Cl_2$ (2 L) and the solution washed with $H_2O$ (1 L), 5% $Na_2CO_3$ (1 L) and $H_2O$ (1 L). The organic solution was dried on $Na_2SO_4$ and evaporated; the residue (450 g) was purified by flash chromatography:

Stationary phase: Silica gel 230–400 mesh Merck KGaA art 9385

Eluent: 4:1 n-hexane/EtOAc

The desired product was obtained (172 g; 0.42 mol). Yield 42%.

mp: 310° C.

Acidic titer (0.1 N $HClO_4$): 98.0%

TLC: Rf 0.32

Stationary phase: Silica gel plates 60 $F_{254}$ (Merck KGaA code 5715)

Eluent: 8:2 n-hexane/EtOAc

Detection: 1% $KMnO_4$ in 1N NaOH

HPLC: 96% (area %) Chromatographic method of Example 3, A).

$[\alpha]_D^{20}$: +0.46° (c 5.6, $CHCl_3$)

$^{13}C$-NMR, $^{1}H$-NMR, MS and IR spectra were consistent with the structure.

Elemental analysis (%):

|  | C | H | N |
|---|---|---|---|
| Calcd. | 64.52 | 8.61 | 3.42 |
| Found | 65.70 | 9.01 | 3.33 |

D) N-(2-Bromoethyl)-N-[2-(1,1-dimethylethoxy)-2-oxoethyl]-O-(phenylmethyl)-L-serine 1,1-dimethylethyl ester

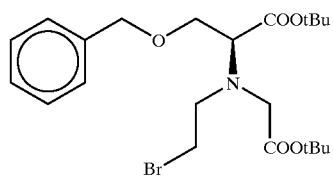

N-Bromosuccinimide (commercial product) (13.9 g; 0.078 mol) was added in portions to a solution of N-(2-hydroxyethyl)-N-[2-(1,1-dimethylethoxy)-2-oxoethyl]-O-(phenylmethyl)-L-serine 1,1-dimethylethyl ester and triphenylphosphine (commercial product) (20.5 g; 0.078 mol) in $CH_2Cl_2$ (250 mL) cooled at 0:5° C. and stirred. After 4 h the solution was washed with $H_2O$ (100 mL), 5% $NaHCO_3$ (100 mL) and $H_2O$ (100 mL). After drying ($Na_2SO_4$) the solution was evaporated and the residue was suspended in $Et_2O$ (150 mL); the solid (triphenyl-phosphine oxide) was filtered and the solution evaporated. The residue (31 g) was purified by flash chromatography:

Stationary phase: Silica gel 230–400 mesh Merck KGaA art 9385 (200 g)

Eluent: 9:1 n-hexane/EtOAc

The desired product was obtained (24 g; 0.051 mol). Yield 78%.

Potentiometric titer (0.1 N $HClO_4/CH_3COCH$): 101%

Argentometric titer (0.1 N $AgNO_3$ after demolition with KOH/DMSO): 101.2%

TLC: Rf 0.40

Stationary phase: Silica gel plates 60 $F_{254}$ (Merck KGaA code 5715)

Eluent: n-hexane/EtOAc 9:1

Detection: 1% KMnO4 in 1N NaOH

GC: 98% (area %)—Gaschromatographic method:

Stationary phase: CIP—SIL DB 5;

Film thickness: 0.25 μm;

Column (WCOT): 10 m×0.53 mm;

Carrier (He)

flow rates:

column flow rate: 10 mL $min^{-1}$;

split flow rate: 110 mL $min^{-1}$;

make up flow rate: 30 mL $min^{-1}$;

septum purge flow rate: 4 mL $min^{-1}$;

Detector (FID) feeding:

hydrogen pressure: 1.2 bar;

air pressure: 2.8 bar;

Oven temperature timetable:initial temperature: 150° C.;

initial time: 2 min;

rate: 20° C. $min^{-1}$;

final temperature: 210° C.;

final time: 25 min;

Injector temperature: 250° C.;

Detector temperature: 250° C.;

Injection: 3 μL;

Sample concentration: 25 mg $mL^{-1}$;

Instrumentation: Hewlett—Packard HP 5890.

$[\alpha]_D^{20}$: −2.51° (c 4.2, $CHCl_3$)

$^{13}C$-NMR, $^{1}H$-NMR, MS and IR spectra were consistent with the structure.

Elemental analysis (%):

|  | C | H | Br | N |
|---|---|---|---|---|
| Calcd. | 55.93 | 7.26 | 16.91 | 2.97 |
| Found | 55.96 | 7.26 | 16.76 | 2.93 |

EXAMPLE 6

Compound 1

[[[-N,N'-[(Carboxymethylimino)di-2,1-ethanediyl] bis[N-carboxymethyl-L-isoleucinate]](5-)]gadolinate (2-)]disodium salt

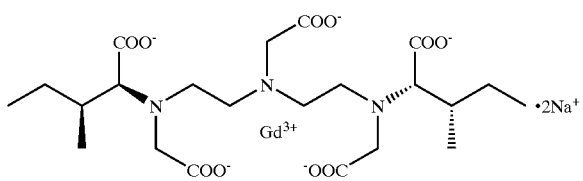

A) N-(2-Bromoethyl)-N-[2-(1,1-dimethylethoxy)-2-oxoethyl]-L-isoleucine 1,1-dimethylethyl ester

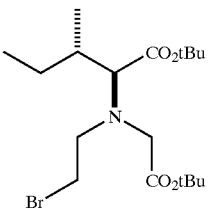

The product is prepared according to Example 2.

B) Glycine 1,1-dimethylethyl ester

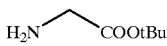

The product is prepared according to Example 1.

C) N,N'-[[[2-(1,1-Dimethylethoxy)-2-oxoethyl]imino]di-2,1-ethanediyl]bis[N-[2-(1,1-dimethylethoxy)-2-oxoethyl] L-isoleucine 1,1-dimethylethyl ester]

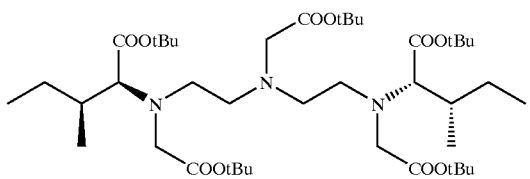

To a solution of N-(2-bromoethyl)-N-[2-(1,1-dimethylethoxy)-2-oxoethyl]-L-isoleucine 1,1-dimethylethyl ester (8.16 g; 25 mmol) and glycine 1,1-dimethylethyl ester (1.31 g; 12.5 mmol) in $CH_3CN$ (100 mL), maintained under vigorous stirring, 2M phosphate buffer pH 8 (100 mL) was added. The biphasic mixture was stirred at 20° C. for 48 h. The organic layer was separated and the solvent evaporated on a rotavapor. The residue was taken up in $CH_2Cl_2$ (100 mL) and the solution washed with water (100 mL) and brine (100 mL). The organic layer was dried over $Na_2SO_4$, concentrated and the residue purified by flash chromatography (n-hexane/EtOAc 9:1 v/v) to give the desired compound (8.2 g; 12.5 mmol). Yield 83.5%.

TLC: Rf 0.5
Stationary phase: silica gel plates 60 $F_{254}$
Eluent: 8:2 n-hexane/EtOAc
Detection: 254 nm; 0.5% $KMnO_4$ in 1N NaOH
$^{13}$C-NMR, $^1$H-NMR, MS and IR spectra were consistent with the structure.
K.F.: <0.1%
Elemental analysis (%):

|  | C | H | N |
|---|---|---|---|
| Calcd. | 64.17 | 10.13 | 5.35 |
| Found | 64.01 | 10.57 | 5.20 |

D) N,N'-[(Carboxymethylimino)di-2,1-ethanediyl]bis[N-carboxymethyl-L-isoleucine]

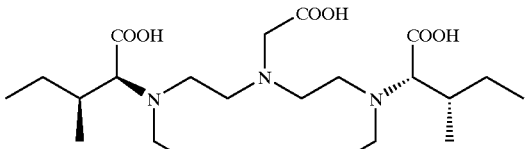

To a solution of the pentaester of the previous preparation (7.92 g; 10.1 mmol) in $CHCl_3$ (150 mL) maintained at 0–5° C. under an inert atmosphere, $(CH_3)_3SiI$ (13.6 mL; 0.1 mol) was added in 30 min. The solution was stirred for 4 days at 20° C., following the reaction by HPLC (chromatographic method of Example 3, A)). The reaction mixture was cooled to 50° C. and $H_2O$ (150 mL) was added. After separation, the pH of the aqueous phase was adjusted to pH 1.7 with 10N NaOH and the solution was loaded onto a column of Amberlite® XAD 1600 resin (500 mL), which was eluted with $H_2O$ (5 L) and then with $H_2O/CH_3CN$ (gradient elution 90:10 75:25 v/v ratios). After evaporation of the solvent the desired product was obtained (4.3 g; 8.5 mmol). Yield 84%.
mp: 117–120° C.
HPLC: 99.9% (area %)
1. Chromatographic method of Example 3, A).
2. Chromatographic method:
Stationary phase: Spheri –10 RP-2 10 μm;
250×4,6 mm column packed by Applied Biosystem;
Temperature: 50° C.;
Mobile phase: isocratic elution with premixed mobile phase: 1 g of n-octylamine is added to 240 mL of acetonitrile mixed with 760 mL of water. The solution is buffered to pH 6 with $H_3PO_4$;
Flow rate: 1.0 mL min$^{-1}$;
Detection (UV): 200 nm;
Injection: 10 μL;
Sample concentration: 2 mg mL$^{-1}$;
Instrumentation: Hewlett—Packard HP 1090 M liquid chromatograph equipped with DR 5 solvent delivery system, autosampler, column thermostat and diode array detector.
$^{13}$C-NMR, $^1$H-NMR, MS and IR spectra were consistent with the structure.
K.F.: 0.44%
Elemental analysis (%):

|  | C | H | N |  |
|---|---|---|---|---|
| Calcd. | 52.27 | 7.78 | 8.31 |  |
| Found | 52.53 | 7.93 | 8.78 | anhydrous |

E) [[[N,N'-[(Carboxymethylimino)di-2,1-ethanediyl]bis[N-carboxymethyl-L-isoleucinate]](5-)]gadolinate(2-)] disodium salt

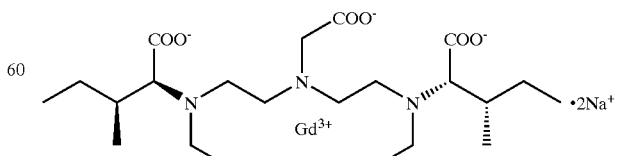

A suspension of the free ligand from the previous preparation (2.53 g; 5 mmol) in $H_2O$ (70 mL) at 5° C. was neutralized by addition of 1N NaOH. To the clear solution was slowly added a 0.2 M solution of GdCl₃ (25 mL; 5 mmol) maintaining the mixture at pH around 7 by addition of 1N NaOH. The resulting cloudy solution was stirred for 30 min at room temperature, then filtered over Millipore GSWP 0,22 m. The clear solution was loaded onto a column of Amberlite XAD 1600 polystyrene resin (300 mL), eluted with H₂O (2 L) and then with H₂O/CH₃OH (1 L; 90:10 v/v). The title. product (3.4 g; 4.83 mmol) was obtained. Yield 97%.

mp: >300° C.
Free ligand (0.001 M GdCl₃): <0.1%
HPLC: 100% (area %)
1. Chromatographic method of Example 3, A).
2. Chromatographic method 2 of previous step D).
MS and IR spectra were consistent with the structure.
K.F.: 7.80%
Weight loss (130° C.): 7.72%
Elemental analysis (%):

|  | C | H | N | Gd | Na |
|---|---|---|---|---|---|
| calcd. | 37.55 | 4.87 | 5.97 | 22.34 | 6.53 |
| found | 37.36 | 4.98 | 5.89 | 22.20 | 6.56 |

EXAMPLE 7

Compound 2

[[[1S-[1R*(1R*,2R*),2R*]]-N,N-Bis[2-[(carboxymethyl)(1- carboxy-2-methylbutyl)amino]ethyl]-L-isoleucinate-(5-)]gadolinate(2-)]disodium salt.

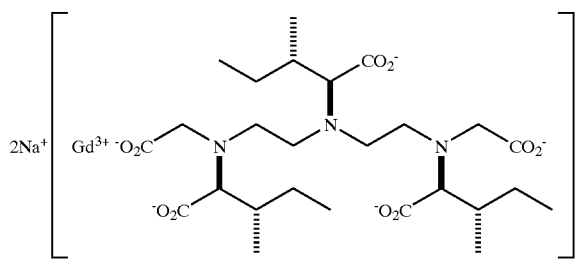

A) N-(2-Bromoethyl)-N-[2-(1,1-dimethylethoxy)-2-oxoethyl]-L-isoleucine 1,1-dimethylethyl ester

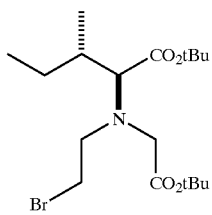

The product is prepared according to Example 2.

B) [1S-[1R*(1R*,2R*),2R*]]-N,N-Bis[2-[[1-[(1,1-dimethylethoxy)carbonyl]-2-methylbutyl][2-[(1,1-dimethylethoxy)-2-oxoethyl]amino]ethyl]-L-isoleucine 1,1-dimethylethyl ester

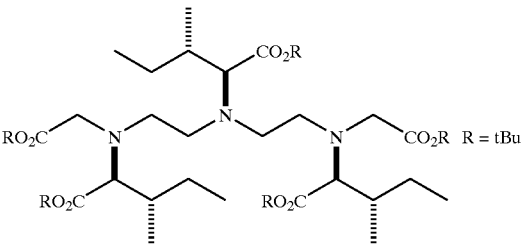

An emulsion of L-isoleucine tert-butyl ester (Example 2, Step A) (1.89 g; 10.1 mmol) and of N-(2-Bromoethyl)-N-[2-(1,1-dimethylethoxy)-2-oxoethyl]-L-isoleucine 1,1-dimethylethyl ester (8.97 g; 22.0 mmol) in acetonitrile (75 mL) and 2 M pH 8 phosphate buffer (50 mL) was vigorously stirred at room temperature for 3 days; the aqueous layer was substituted with fresh buffer and stirring went on for another day. As reaction rate sensibly decreased when conversion of starting materials approached 70 to 80%, conditions were forced by heating at 50° C. for 40 h and at 70° C. for 16 h. The phases were allowed to separate and cool; the organic layer was evaporated and taken up in EtOAc, the aqueous layer was extracted with EtOAc (2×100 mL). The combined organic layers were washed with water (2×150 mL), brine (100 mL) and at last dried over Na₂SO₄. The crude (11.74 g) was purified by flash chromatography (n-hexane/iPr₂O 9:1 to 8:2). After careful removal of solvents in vacuo, the desired compound was obtained (5.55 g; 6.59 mmol). Yield 65%.

TLC: R_f 0.4
Stationary phase: silica gel.
Eluent: n-hexane/iPr₂O 9:1 (v/v).
Detection: 254 nm; I₂;0.5% KMnO₄ in 1 N NaOH.
¹H-NMR, ¹³C-NMR, MS and IR spectra were consistent with the structure.

C) [1S-[1R*(1R*,2R*),2R*]-N,N-Bis[2-[(carboxy-methyl)-(1-carboxy-2-methylbutyl)amino]ethyl]-L-isoleucine

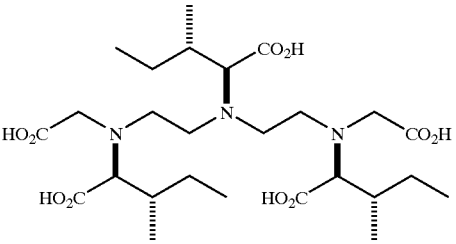

To a solution of the pentaester obtained in the previous preparation (6.36 g; 7.55 mmol) in CHCl₃ (0.3 L, freshly distilled over CaH₂) under a nitrogen atmosphere, iodotrimethylsilane (12.0 mL; 88.2 mmol) was slowly added at −15° C. The mixture was allowed to gradually rise to room temperature and left stirring for 3 days. Then it was cooled in an ice bath and so much 1 N NaOH was added that a pH value of 10 could be established in the upper layer. Vigorous stirring was prolonged until both phases became homogeneous and separable. After separation the organic phase was extracted with 0.1 N NaOH (100 mL); the combined aqueous layers were washed with diethyl ether (2×200 mL), then concentrated to a volume of 100 mL. To the solution warmed in a steam bath at 40° C., 9 N HCl was slowly added under vigorous stirring; as pH drifted under a value of 5, acidification was brought forth even slower with 2 N HCl down to a pH value of 2.74 (below which precipitation of a white unworkable gum began). The just acidified solution was loaded onto a column of resin Amberlite® XAD 1600 (370 mL). After initial very slow percolation of water (which drew off not only inorganic salts but also a minor quantity of the desired product as a polysodium salt), a gradient elution of water/acetonitrile was applied (95:5, 0.5 L; 90:10, 0.5 L; 85:15 0.5 L; 80:20, 0.5 L; 75:25 0.5 L; 70:30, 0.5 L; 65:35, 1 L). The homogeneous fractions were combined and concentrated to a volume of 500 mL. This solution [containing 3.3 mmol of ligand] was submitted to the ensuing complexation without isolation of the product. Approximate yield: 44%.

mp: broad softening range (125–175° C.)
HPLC: 100% (area)—Chromatographic method:
Stationary phase: Lichrospher 100 RP-8 5 μm;
250×4 mm column packed by Merck KGAA;
Temperature: 45° C.;
Mobile phase: isocratic elution with premixed mobile phase: 1 g of n-octylamine is added to 262 mL of acetonitrile mixed with 738 mL of water. The solution is buffered to pH 6.0 with $H_3PO_4$;
Flow rate: 1.3 mL min$^{-1}$;
Detection (UV): 205 nm;
Injection: 30 μL;
Sample concentration: 1 or 5 mg mL$^{-1}$;
Instrumentation: Merck KGaA—Hitachi high pressure gradient pump system (L6200 and L6000), Merck KGaA—Hitachi AS 2000 autosampler, Merck KGaA T 6300 column thermostat, Merck KGaA—Hitachi L 4250 UV detector.
$^1$H-NMR, $^{13}$C-NMR, MS and IR spectra were consistent with the structure.

D) [[[1S-[1R*(1R*,2R*),2R*]]-N,N-Bis[2-[(carboxymethyl)(1-carboxy-2-methylbutyl)amino]ethyl]-L-isoleucinate(5-)]gadolinate(2-)]disodium salt.

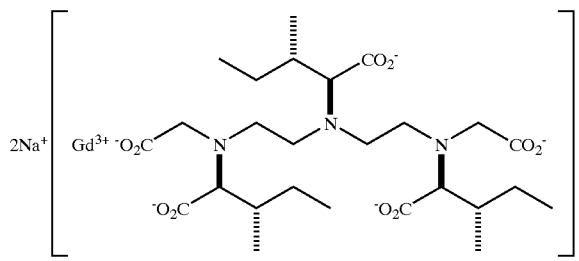

To the aqueous solution (500 mL) of the ligand obtained in the previous preparation (ca. 3.3 mmol) $Gd_2O_3$ (596 mg; 1.64 mmol) and 0.1 N NaOH (64 mL; 6.4 mmol) were added. The reaction progress was monitored by HPLC. After setting on heating at 60° C. for 3 h, the mixture became clear although complexation was not complete, so another portion of $Gd_2O_3$ (64 mg; 0.18 mmol) was added and stirring maintained for 4 days at room temperature. Because at this point a relevant quantity of free ligand was again discernible in the HPLC pattern, although some oxide was available in the mixture, further large excess $Gd_2O_3$ (427 mg; 1.18 mmol) was added and heating restored at 65° C. for 14 h. Complete conversion was achieved by addition of Gd(OAc)3 (91 mg; 0.22 mmol) and brief heating at 65° C. The slurry was then cooled to room temperature, filtered through paper and concentrated on a rotavapor. Azeotropic distillations with toluene were repeated in order to remove any trace of acetic acid. The residue was diluted in water/methanol 95:5 (100 mL) and loaded onto a column of resin Amberlite® XAD 1600 (280 mL), conditioned with water/methanol 95:5. A gradient elution of water/methanol was applied (95:5, 92:8, 86:14—percentage at which the chelate complex began to elute—82:18, 78:22, 74:26, 70:30; 7×0.5 L). After removal of solvents in vacuo and repeated azeotropic distillations with toluene, the title compound was obtained (2.41 g; 3.17 mmol). Approximate yield: 96%. Yield over the last two steps: 42%.

mp: >2950° C. (dec)
HPLC: 97% (area)—Chromatographic method:
Stationary phase: Lichrospher 100 RP-8 5 μm;
250×4 mm column packed by Merck KGaA;
Temperature: 450° C.;
Mobile phase: isocratic elution with premixed mobile phase: 1 g of n-octylamine is added to 325 mL of acetonitrile mixed with 675 mL of water. The solution is buffered to pH 6.0 with $H_3PO_4$;
Flow rate: 1.3 mL min$^{-1}$;
Detection (UV): 205 nm;
Injection: 30 μL;
Sample concentration: 5 mg mL$^{-1}$;
Instrumentation: Merck KGAA—Hitachi high pressure gradient pump system (L6200 and L6000), Merck KGaA—Hitachi AS 2000 autosampler, Merck KGaA T 6300 column thermostat, Merck KGaA—Hitachi L 4250 UV detector.
MS and IR spectra were consistent with the structure.
K.F.: 5.17%
Specific rotation (305): $[\alpha]_{436}^{20}$=+1.7°; $[\alpha]_{405}^{20}$=+5.7°; $[\alpha]_{365}^{20}$=+11.50; (c 1.16; $CH_3OH$)
Weight loss (130° C.): 6.32%
Elemental analysis (after drying at 130° C.) (%):

|  | C | H | Gd | N | Na |
|---|---|---|---|---|---|
| Calcd. | 41.10 | 5.57 | 20.69 | 5.53 | 6.05 |
| Found | 41.08 | 5.78 | 20.46 | 5.48 | 6.02 |

EXAMPLE 8

Compound 3

[[[-N,N'-[(Carboxymethylimino)di-2,1-ethanediyl]bis[N-carboxymethyl-L-tryptophanate]](5-)]gadolinate(2-)]disodium salt

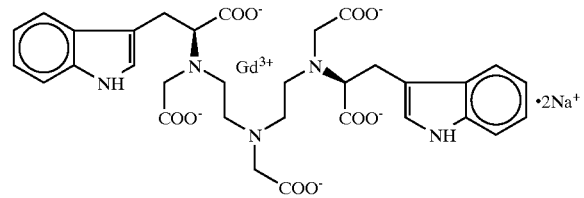

A) Glycine 1,1-dimethylethyl ester
The product is prepared according to Example 1.
B) N-(2-bromoethyl)-N-[2-(1,1-dimethylethoxy)-2-oxoethyl]-L-tryptophan 1,1-dimethylethyl ester
The product is prepared according to Example 4.

C) N,N'-[[[2-(1,1-Dimethylethoxy)-2-oxoethyl]imino]di-2,1-ethanediyl]bis[N-[2-(1,1-dimethylethoxy)-2-oxoethyl]-L-tryptophan 1,1-dimethylethyl ester]

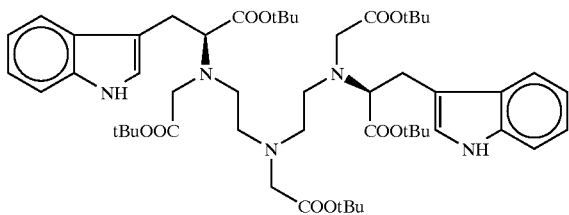

To a solution of glycine 1,1-dimethylethyl ester (1.7 g; 12.5 mmol) and N-(2-bromoethyl)-N-[2-(1,1-dimethylethoxy)-2-oxoethyl]-L-tryptophan 1,1-dimethylethyl ester (12 g; 24.9 mmol) in $CH_3CN$ (70 mL), 2M phosphate buffer pH 8 (100 mL) was added. The bifasic mixture was maintained under vigorous mechanical stirring for 20 h. The organic layer was separated and concentrated. The oily residue was purified by flash chromatography (n-hexane/EtOAc 8:2) to give the desired compound (17.5 g; 18.75 mmol). Yield 75%.

TLC: Rf 0.45
Stationary phase: silica gel plates 60 $F_{254}$
Eluent: 7:3 n-hexane/EtOAc
Detection: 254 nm; 0.5% $KMnO_4$ in 1N NaOH
HPLC: 98.9% (area %)—Chromatographic method of Example 3, A).
$^{13}C$-NMR, $^1H$-NMR, MS and IR spectra were consistent with the structure.
K.F.: 0.56%
Elemental analysis (%):

|  | C | H | N |
|---|---|---|---|
| Calcd. | 67.00 | 8.33 | 7.51 |
| Found | 65.89 | 8.29 | 7.54 anhydrous |

D) N,N'-[(Carboxymethylimino)di-2,1-ethanediyl]bis[N-carboxymethyl-L-tryptophan]

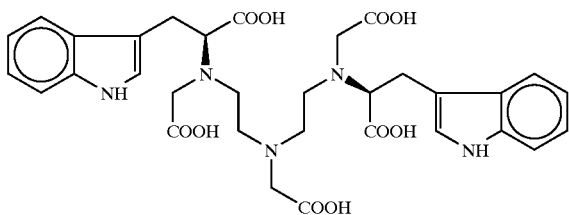

To a solution of the pentaester obtained in the previous preparation (8.51 g; 9 mmol) in anhydrous CHCl3 (150 mL) maintained at 0–5° C. under an inert atmosphere, $(CH_3)_3SiI$ (12.4 mL; 90 mmol) was added in 30 min. The temperature was allowed to rise to r.t., the violet solution was stirred for 64 h and the reaction progress was monitored by HPLC (Chromatographic method of Example 3, A)). After cooling to 0° C. the reaction mixture was maintained under vigorous stirring, while 1N NaOH (120 mL) was added to achieve complete dissolution of the precipitate. The organic layer was separated and the aqueous phase was acidified to pH 3 with 6N HCl. The precipitate was filtered off, washed with cold $H_2O$ (200 mL), and dried over $P_2O_5$ until constant weight (6 g). The brownish solid was suspended in $H_2O$ (100 mL) and 3N HCl was added until complete dissolution (pH 1.5). The solution was loaded onto a column filled with Amberlite® XAD 1600 resin (600 mL) which was eluted with $H_2O$ (1000 mL) and then with $H_2O/CH_3CN$ (gradient elution 90:10 85:15 v/v ratios). After evaporation of the solvent the desired compound (4 g; 6.14 mmol) was obtained. Yield 68%.

mp: 168–170° C
HPLC: 99.5% (area %)—Chromatographic method of Example 3, A).
$^{13}C$-NMR, $^1H$-NMR, MS and IR spectra were consistent with the structure.
K.F.: 2.28%
Elemental analysis (%):

|  | C | H | N |  |
|---|---|---|---|---|
| Calcd. | 58.98 | 5.72 | 10.75 |  |
| Found | 58.55 | 5.79 | 10.73 | anhydrous |

E) [[[-N,N'-[(Carboxymethylimino)di-2,1-ethane-diyl]-bis[N-carboxymethyl-L-tryptophanate]](5-)]gadolinate-(2-)] disodium salt

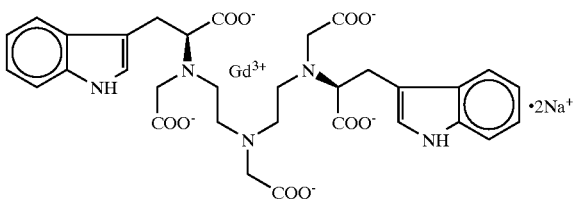

To a solution of the free ligand from the previous preparation (3.23 g; 5 mmol) in $H_2O$ (100 mL) brought to pH 6.5 with 1N NaOH, $Gd_2O_3$ (0.91 g; 2.5 mmol) was added and the suspension was warmed at 70° C. for 5 h. The reaction course was monitored by HPLC:

Chromatographic method:
Stationary phase: Lichrospher 100 RP-8 5 mm;
250×4 mm column packed by Merck KGaA;
Temperature: 40° C.;
Mobile phase: isocratic elution with premixed mobile phase: 1 g of n-octylamine is added to 300 mL of acetonitrile mixed with 700 mL of water. The solution is buffered to pH 6 with $H_3PO_4$;
Flow rate: 1 mL $min^{-1}$;
Detection (UV): 200 nm;
Injection: 10 μL;
Sample concentration: 1 mg $mL^{-1}$;
Instrumentation: Merck KGaA—Hitachi high pressure gradient pump system (L6200 and L6000), Merck KGaA—Hitachi AS 2000 autosampler, Merck KGaA T 6300 column thermostat, Merck KGaA—Hitachi L 4250 UV detector.

The cloudy solution was filtered through a Millipore® HA 0.45 m filter and the pH was adjusted to 6.7 with 1N NaOH. The filtrate was concentrated under reduced pressure to give the title compound (3.3 g; 3.88 mmol). Yield 78%.

mp: >250° C.
Free ligand (0.001 M $GdCl_3$): <0.1%
HPLC: 99.8% (area %)—Chromatographic method of above.
MS and IR spectra were consistent with the structure.
K.F.: 14.09%

Elemental analysis (%):

|  | C | H | N | Gd | Na |  |
|---|---|---|---|---|---|---|
| calcd. | 45.23 | 3.80 | 8.24 | 18.50 | 5.41 |  |
| found | 45.36 | 3.69 | 8.20 | 18.26 | 5.17 | anhydrous |

EXAMPLE 9

Compound 4

[[[[S-(R*,R*)]-N,N'-[[(1-Carboxy-2-methylbutyl)imino]di-2,1-ethanediyl]bis[N-carboxymethyl-L-tryptophanate]]-(5-)]gadolinate(2-)]disodium salt

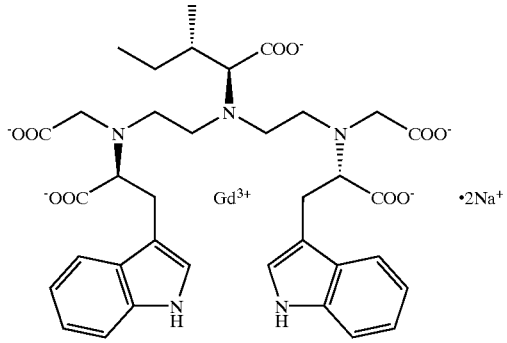

A) L-isoleucine 1,1-dimethylethyl ester
  The product is prepared according to Example 2, Step A.
B) N-(2-bromoethyl)-N-[2-(1,1-dimethylethoxy)-2-oxoethyl]-L-tryptophan 1,1-dimethylethyl ester
  The product is prepared according to Example 4.
C) [(S-(R*,R*)]-N,N'-[[1-[((1,1-Dimethylethoxy)-carbonyl]-2-methylbutyl]imino]di-2,1-ethanediyl]bis[N-[2-(1,1dimethylethoxy)-2-oxoethyl]-L-tryptophan 1,1-dimethylethyl ester]

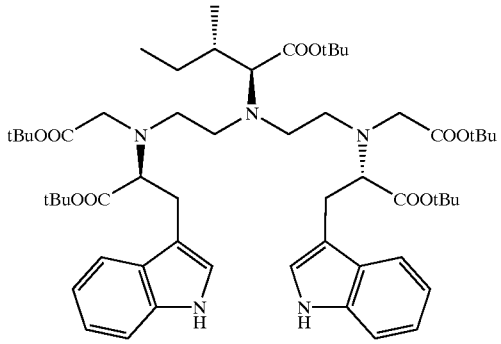

To a solution of L-isoleucine 1,1-dimethylethyl ester (0.86 g; 4.59 mmol) and N-(2-bromoethyl)-N-[2-(1,1-dimethylethoxy)-2-oxoethyl]-L-tryptophan 1,1-dimethylethyl ester (4.42 g; 9.18 mmol) in CH$_3$CN (65 mL) 2M pH 8 phosphate buffer (65 mL) was added. The reaction was maintained under vigorous mechanical stirring and followed by T.L.C. After 3 h the aqueous phase was replaced with the same amount of fresh 2M pH 8 phosphate buffer and the same operation was repeated after 18 h. After 23 h the organic layer was separated and evaporated. The residue was purified by flash chromatography:
  1$^{st}$ column: silica gel; n-hexane/ethyl acetate, 8:2 v/v
  2$^{st}$ column: silica gel; CHCl$_3$/MeOH, 15:0.2 v/v
The desired product (3.88 g; 3.9 mmol) was obtained. Yield 85.5%.
  TLC: Rf 0.25
  Stationary phase: silica gel plates 60 F$_{254}$
  Eluent 8:2 n-hexane/EtOAc
  Detection: 254 nm; 0.5% KMnO$_4$ in 1N NaOH
  $^{13}$C-NMR, $^1$H-NMR and MS spectra were consistent with the structure.
D) [(S-(R*,R*)]-N,N'-[[(1-Carboxy-2-methylbutyl)-imino]-di-2,1ethanediyl]bis[N-carboxymethyl-L-tryptophan]

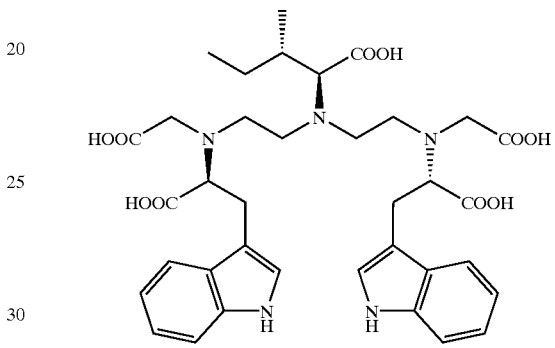

Into a solution of the pentaester from the previous preparation (6.0 g; 6.07 mmol) in CH$_2$Cl$_2$ (freshly distilled over CaH$_2$) in an inert atmosphere (CH$_3$)$_3$SiI (8.3 mL; 60.97 mmol) was slowly dropped (0.5 h) maintaining the temperature around 0° C. After removal of the cooling bath the temperature was allowed to rise to r.t. and the reaction was followed by HPLC (Chromatographic method of Example 3, A)). After 44 h fresh (CH$_3$)$_3$SiI (5 mL; 36.73 mmol) was added and after further 70 h (overall 114 h) other (CH$_3$)$_3$SiI (1 mL; 7.35 mmol) was added. After 23 h (overall 137 h) the solution was poured into a 250 mL becker and vigorously stirred while 1N NaOH (5×100 mL) was added. The mixture was settled after each addition of NaOH until the organic layer became clear and from HPLC analysis the desired product completely disappeared. After separation the aqueous layer was acidified to pH 6.5 by addition of 37% HCl and the solution, without isolation of the product, used for the following complexation.
  mp: 185° C. dec.
  HPLC: 95% (area %) Chromatographic method of Example 3, A).
  K.F.: 7.15%
  $^{13}$C-NMR, $^1$H-NMR and MS spectra were consistent with the structure.
Elemental analysis (%):

|  | C | H | N | Cl | Na |  |
|---|---|---|---|---|---|---|
| Calcd. | 61.09 | 6.41 | 9.89 | — | — |  |
| Found | 60.91 | 6.08 | 10.19 | — | — | anhydrous |

E) [[([[S-(R*,R*)]-N,N'-[[(1-Carboxy-2-methylbutyl)-imino]di-2,1-ethanediyl]bis[N-carboxymethyl-L-tryptophanate]](5-)]gadolinate(2-)]disodium salt

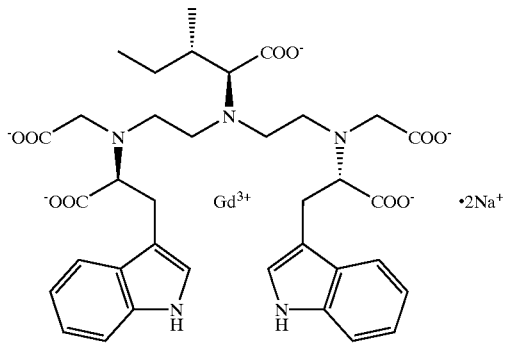

To the solution coming from the previous step were simultaneously added a solution of GdCl$_3$.6 H$_2$O (2.26 g; 6.07 mmol) in H$_2$O (50 mL) and 1N NaOH to maintain the mixture at pH 6.5. The reaction was followed by HPLC analysis. After 1 h the pH was adjusted to 7 with 1N NaOH and the solution loaded onto a column of Amberlite® XAD-1600 resin (500 mL). The column was eluted with H$_2$O until complete elimination of the salts, then the product was eluted with a solution of H$_2$O/CH$_3$CN 9:1. The solution containing the product (90% purity) was eluted a second time through Amberlite® XAD-1600 resin (500 mL) in a similar way. A portion of the product was not pure enough yet, so it was necessary a third purification through Amberlite® XAD-1600 resin (500 mL) but this time the resin was conditioned and the product was dissolved in H$_2$O/CH$_3$CN 9:1. The solution containing the purified product (pH 8.7) was concentrated to 50 mL and, while maintained under stirring, some Dowex CCR-3 LB resin was added until the pH of the solution was adjusted to 4. The resin was filtered through a G3 septum and washed with warm (40° C.) H$_2$O (100 mL). The pH of the clear solution was corrected to 7 by addition of 1N NaOH. After elimination of the solvent the title compound (2.18 g; 2.41 mmol) was obtained. Yield 40% starting from the pentaester.

mp: >250° C.

HPLC: 100% (area %)—Chromatographic method:

Stationary phase: Lichrospher 100 RP-8 5 mm;

250×4 mm column packed by Merck KGaA;

Temperature: 45° C.;

Mobile phase: isocratic elution with premixed mobile phase: 1 g of n-nonylamine is added to 330 mL of acetonitrile mixed with 670 mL of water. The solution is buffered to pH 6 with H$_3$PO$_4$;

Flow rate: 1 mL min$^{-1}$;

Detection (UV): 245 nm;

Injection: 10 μL;

Sample concentration:1 mg mL$^{-1}$;

Instrumentation: Merck KGaA—Hitachi high pressure gradient pump system (L6200 and L6000), Merck KGaA—Hitachi AS 2000 autosampler, Merck KGaA T 6300 column thermostat, Merck KGaA—Hitachi L 4250 UV detector.

K.F.: 12.91%

MS and IR spectra were consistent with the structure.

Elemental analysis (%):

|  | C | H | N | Gd | Na |  |
|---|---|---|---|---|---|---|
| Calcd. | 47.73 | 4.45 | 7.73 | 17.36 | 5.08 |  |
| Found | 47.19 | 4.28 | 7.67 | 17.12 | 5.13 | anhydrous |

EXAMPLE 10

Compound 5

[[[1S-[1R*(1R*,2R*),2R*]]-N,N-Bis[2-[(carboxymethyl)(1-carboxy-2-methylbutyl)amino]ethyl]-L-tyrosinate-(5-)]gadolinate(2-)]disodium salt

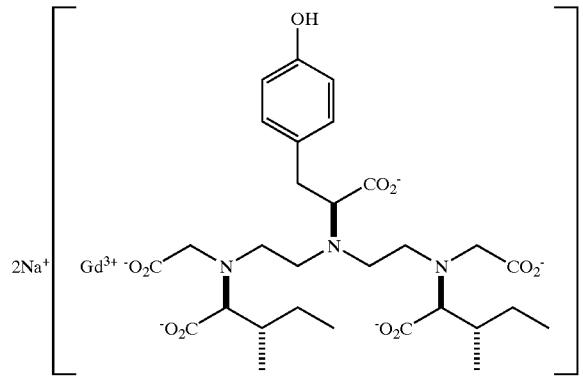

A) N-(2-Bromoethyl)-N-[2-(1,1-dimethylethoxy)-2-oxoethyl]-L-isoleucine 1,1-dimethylethyl ester

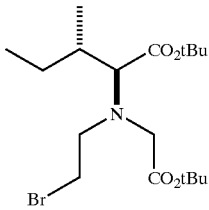

The product is prepared according to Example 2.

B) L-tyrosine tert-butyl ester

This product is commercially available (Novabiochem art. 04-12-5026, batch no. A09451-CAS No. [16874-12-7]).

C) [1S-[1R*(1R*,2R*),2R*]]-N,N-Bis[2-[[1-[(1,1-dimethylethoxy)carbonyl]-2-methylbutyl][2-(1,1-dimethylethoxy)-2-oxoethyl]amino]ethyl]-L-tyrosine 1,1-dimethylethyl ester

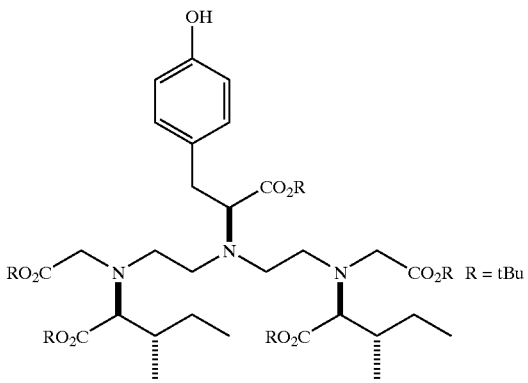

An emulsion of L-tyrosine tert-butyl ester (2.15 g; 9.06 mmol), N-(2-bromoethyl)-N-[2-(1,1-dimethylethoxy)-2-oxoethyl]-L-isoleucine 1,1-dimethyl ethyl ester (7.43 g; 18.2 mmol) in acetonitrile (150 mL) and 2 M phosphate buffer pH 8 (100 mL) was vigorously stirred at room temperature for 2 days; the aqueous layer was substituted with fresh buffer and stirring went on for another day. As reaction rate sensibly decreased when conversion of starting materials approached 70 to 80%, a slight excess of N-(2-bromoethyl)-N-[2-(1,1-dimethylethoxy)-2-oxoethyl]-L-isoleucine 1,1-dimethyl ethyl ester (1.12 g; 2.74 mmol) was added and stirring was prolonged 4 days more. The phases were allowed to separate; the organic layer was evaporated and taken up in EtOAc, the aqueous layer was extracted with EtOAc (300 mL). The combined organic layers were washed with water (400 mL), brine (100 mL) and at last dried over $Na_2SO_4$. The crude (11.74 g) was purified by flash chromatography (n-hexane/EtOAc 9:1 to 8:2). After careful removal of solvents in vacuo, the desired compound was obtained (8.13 9; 9.11 mmol). Quantitative yield.

TLC: $R_f$ 0.4

Stationary phase: silica gel.

Eluent: n-hexane/EtOAc 75:25 (v/v).

Detection: 254 nm; $I_2$; 0.5% $KMnO_4$ in 1 N NaOH.

$^1$H-NMR, $^{13}$C-NMR, MS and IR spectra were consistent with the structure.

D) [1S-[1R*(1R*,2R*),2R*]]-N,N-Bis[2-[(carboxymethyl)-(1-carboxy-2-methyl-butyl)amino]ethyl]-L-tyrosine

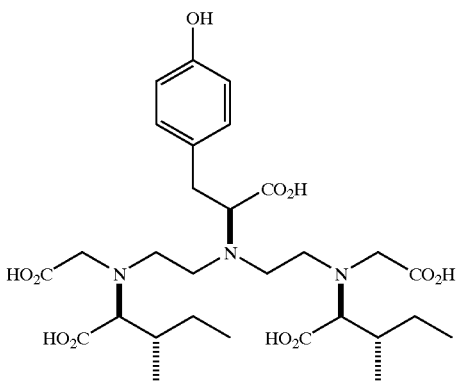

To a solution of the pentaester obtained from the previous preparation (7.63 g; 8.55 mmol) in $CHCl_3$ (250 mL, freshly distilled over $CaH_2$) under a nitrogen atmosphere, iodotrimethylsilane (14.0 mL; 102 mmol) was slowly added at −15° C. The mixture was allowed to gradually rise to room temperature and then was stirred for 3 days. Then it was cooled in an ice bath and so much 1 N NaOH was added that a pH value of 10 could be established in the upper layer. Vigorous stirring was prolonged until both phases became homogeneous and separable. After separation the organic phase was extracted with 0.1 N NaOH (100 mL); the combined aqueous layers were washed with diethyl ether (400 mL), then concentrated to a volume of 100 mL. To the solution warmed in a steam bath at 50° C., 6 N HCl was slowly added under vigorous stirring; as pH drifted under a value of 5, acidification was brought forth even slower with 2 N HCl down to a pH value of 2.70 (below which precipitation of a white unworkable gum began). The just acidified solution was loaded onto a column of resin Amberlite® XAD 1600 (250 mL). After initial very slow percolation of water, a gradient elution of water/acetonitrile was applied (95:5, 0.5 L; 92.5:7.5, 0.5 L; 90:10 0.5 L; 87:13, 0.5 L; 84:16, 0.5 L; 80:20, 1 L; 76:24, 0.5 L; 72:28, 0.5 L; 68:32, 0.5 L; 64:36, 0.5 L; 60:40, 0.5 L). The homogeneous fractions were combined and concentrated to a volume of 1000 mL; this solution was submitted to the ensuing complexation without isolation of the ligand. Approximate yield: 50%.

mp: broad softening range (115–175° C.), then decomposition

HPLC: 98.2% (area)—Chromatographic method:

Stationary phase: Lichrospher 100 RP-8 5 μm;

250×4 mm column packed by Merck KGaA;

Temperature: 45° C.;

Mobile phase: isocratic elution with premixed mobile phase: 1 g of n-octylamine is added to 244 mL of acetonitrile mixed with 756 mL of water. The solution is buffered to pH 6.0 with $H_3PO_4$;

Flow rate: 1.3 mL min$^{-1}$;

Detection (UV): 210 nm;

Injection: 10 μL;

Sample concentration: 1 mg mL$^{-1}$;

Instrumentation: Merck KGaA—Hitachi high pressure gradient pump system (L6200 and L6000), Merck KGaA—Hitachi AS 2000 autosampler, Merck KGaA T 6300 column thermostat, Merck KGaA—Hitachi L 4250 UV detector.

$^1$H-NMR, $^{13}$C-NMR, MS and IR spectra were consistent with the structure.

Specific rotation: $[Ó]_D^{20}$=−41.2°; (c 1.13; DMF)

K.F.: 2.66%

Elemental analysis (%):

|  | C | H | N | O |  |
| --- | --- | --- | --- | --- | --- |
| Calcd. | 56.94 | 7.41 | 6.87 | 28.77 |  |
| Found | 57.12 | 7.56 | 6.88 | 28.09 | anhydrous |

E) [[[1S-[1R*(1R*,2R*),2R*]]-N,N-Bis[2-[(carboxymethyl)(1-carboxy-2-methylbutyl)amino]ethyl]-L-tyrosinate-(5-)]gadolinate(2-)]disodium salt

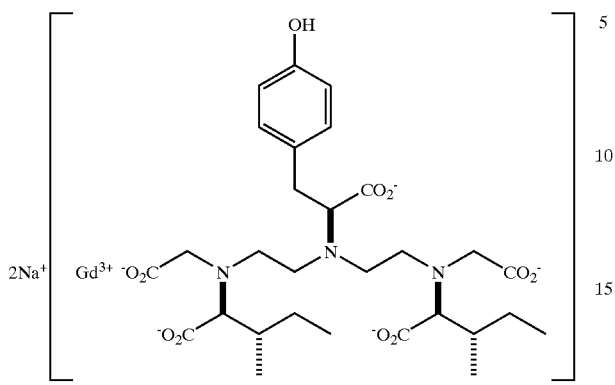

To the aqueous solution (750 mL) of the free ligand [ca. 3.29 mmol from the previous preparation] $Gd_2O_3$ (604 mg; 1.67 mmol) and 0.1 N NaOH (65.8 mL; 6.58 mmol) were added. The reaction progress was monitored by HPLC (Chromatographic method of the previous step E)). After setting on heating at 60° C. for 3 h, the mixture became clear although complexation was not complete, so another portion of $Gd_2O_3$ (23 mg; 0.063 mmol) was added and stirring maintained for 4 days at room temperature. The slurry was then filtered through paper and concentrated on a rotavapor to 100 mL. The resulting clear solution was slowly percolated (flow 40 mL/h) through a column of Dowex® CCR3LB ($Na^+$ form; 35 mL). The collected eluates underwent liophilization and the title compound was isolated (2.42 g; 2.99 mmol). Approximate yield: 91%. Yield over the last two steps: 45%.

mp: >240° C. (dec)

HPLC: 100% (area)—Chromatographic method:
Stationary phase: Lichrospher 100 RP-8 5 mm;
250×4 mm column packed by Merck KGaA;
Temperature: 45° C.;
Mobile phase: isocratic elution with premixed mobile phase: 1 g of n-octylamine is added to 298 mL of acetonitrile mixed with 702 mL of water. The solution is buffered to pH 6.0 with $H_3PO_4$;
Flow rate: 1.3 mL $min^{-1}$;
Detection (UV): 210 nm;
Injection: 10 µL;
Sample concentration: 1 and 5 mg $mL^{-1}$;
Instrumentation: Merck KGaA—Hitachi high pressure gradient pump system (L6200 and L6000), Merck KGaA—Hitachi AS 2000 autosampler, Merck KGaA T 6300 column thermostat, Merck KGaA—Hitachi L 4250 UV detector.

MS and IR spectra were consistent with the structure.

Specific rotation (300) $[\alpha]_{589}^{20}=-20.8°$; $[\alpha]_{578}^{20}=-21.4$; $[\alpha]_{546}^{20}=-29.8°$; $[\alpha]_{436}^{20}=-46.9°$; $[\alpha]_{405}^{20}=-54.2°$; $[\alpha]_{365}^{20}=-72.1°$ (c 1.11; $CH_3OH$)

K.F.: 8.57%
Weight loss (130° C.): 8.82%
Elemental analysis (%):

|  | C | H | Gd | N | Na |
|---|---|---|---|---|---|
| Calcd. | 43.01 | 4.98 | 19.42 | 5.19 | 5.68 |
| Found | 42.96 | 5.19 | 18.69 | 5.04 | 5.59 |

EXAMPLE 11

Compound 6

[[[4S-[4R*,8(R*),12R*]]-4-Carboxy-8-[1-carboxy-2-(4-hydroxyphenyl)-ethyl]-5,11-bis(carboxymethyl)-1-phenyl-12-[(phenylmethoxy)methyl]-2-oxa-5,8,11-triazatridecan-13-oate(5-)]gadolinate(2-)]dihydrogen compound with 1-deoxy-1-methylamino-D-glucitol (1:2)

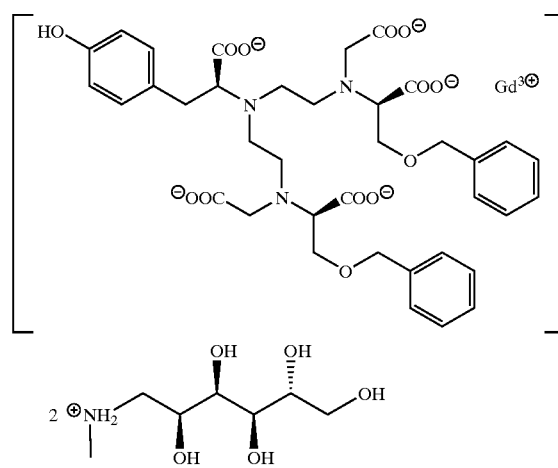

A) L-tyrosine 1,1-dimethylethyl ester
This product is commercially available (Novabiochem art. 04-12-5026-CAS No. [16874-12-7]).

B) N-(2-Bromoethyl)-N-[2-(1,1-dimethylethoxy)-2-oxoethyl]-O-(phenylmethyl)-L-serine
The product has been prepared according to Example 5.

C) [4S-[4R*,8(R*),12R*]]-4-[(1,1-Dimethylethoxy)carbonyl]-8-[1-[(1,1-dimethylethoxy)carbonyl]-2-(4-hydroxyphenyl)ethyl]-5,11-bis[2-(1,1-dimethylethoxy)-2-oxo-ethyl]-1-phenyl-12-[(phenylmethoxy)-methyl]-2-oxa-5,8,11-triazatridecan-13-oic acid 1,1-dimethylethyl ester

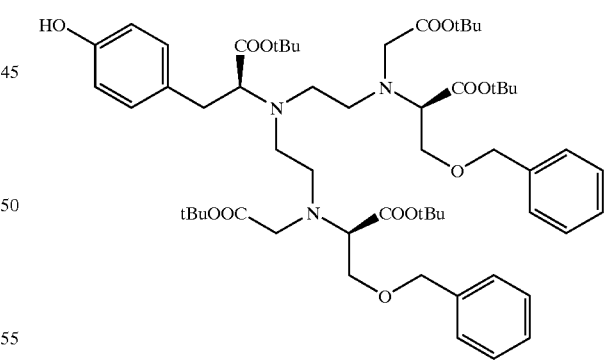

L-Tyrosine 1,1-dimethylethyl ester (5.1 g; 22 mmol) was added to a stirred solution of N-(2-bromoethyl)-N-[2-(1,1-dimethylethoxy)-2-oxoethyl]-O-(phenylmethyl)-L-serine 1,1-dimethylethyl ester (21.6 g; 46 mmol) in $CH_3CN$ (250 mL). A 2 M pH 8 phosphate buffer solution (350 mL) was added and the resulting biphasic mixture was vigorously stirred for 12 h. The two phases were separated and fresh 2 M pH 8 phosphate buffer solution (200 mL) was added to the organic phase. After stirring for an additional 2 h the organic phase was evaporated under reduced pressure (2 kPa) and the residue dissolved in $CH_2Cl_2$ (300 mL). The resulting solution was washed with water (200 mL), dried over $Na_2SO_4$ and concentrated to residue. The crude (28.7 g) was purified by flash chromatography:

Stationary phase: silica gel 230–400 Mesh (E. Merck art. 9385)

Eluent: 8:2 to 6:4 hexane/EtOAc

The desired product was obtained (19.9 g, 19 mmol). Yield 90%.

HPLC: 96.5% (area %) Chromatographic method of Example 3, A).

TLC: Rf=0.26

Silica gel plates 60 $F_{254}$ (E. Merck art. 5715)

Eluent: 8: 2 hexane/EtOAc

Detection: UV (254 nm) and 1% $KMnO_4$ in 1 M NaOH $^{13}$C-NMR, $^1$H-NMR and MS spectra were consistent with the structure.

D) [4S-[4R*,8(R*),12R*]]-4-Carboxy-8-[1-carboxy-2-(4-hydroxyphenyl)ethyl]-5,11-bis(carboxymethyl)-1-phenyl-12-[(phenylmethoxy)-methyl]-2-oxa-5,8,11-triazatridecan-13-oic acid

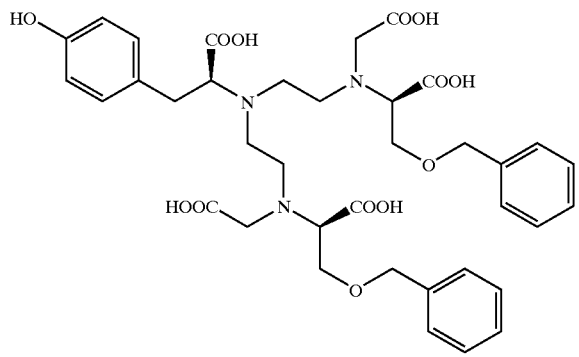

$CF_3COOH$ (7 mL; 10.4 g; 90 mmol) was added to a solution of [4S-[4R*,8(R*),12R*]]-4-[(1,1-dimethylethoxy)carbonyl]-8-[1-[(1,1-dimethylethoxy)carbonyl]-2-(4-hydroxyphenyl)ethyl]-5,11-bis[2-(1,1-dimethylethoxy)-2-oxoethyl]-1-phenyl-12-[(phenylmethoxy)methyl]-2-oxa-5,8,11-triazatridecan-13-oic acid 1,1-dimethylethyl ester (22.4 g; 22 mmol) in $CH_2Cl_2$ (100 mL) cooling the mixture at 0–5° C. The resulting solution was evaporated under reduced pressure (2 kPa) and the residue was dissolved in $CF_3COOH$ (150 mL; 224 g; 2 mol). The solution was stirred at room temperature for 60 h, then evaporated (2 kPa) and the residue was washed with $CH_2Cl_2$ (3×150 mL) evaporating each time the solvent under reduced pressure (2 kPa). The resulting crystalline material was suspended in diethyl ether (100 mL) and filtered. After repeating the treatment for three times the crude material (17 g) was dissolved in a 1:1 EtOH/$H_2O$ mixture and loaded onto an Amberlite® XAD 1600 polystyrene resin (700 mL; conditioned with 1:1 EtOH/$H_2O$) eluting with 1:1 EtOH/$H_2O$ to give the desired product (14. mmol). Yield 64%.

HPLC: 96% (area %)

$^{13}$C-NMR, $^1$H-NMR and MS spectra were consistent with the structure.

$[\alpha]_D^{20}$-8.2° (c 1.025, 0.4 M NaOH)

Elemental analysis (%):

|  | C | H | N |
|---|---|---|---|
| calcd. | 60.06 | 6.14 | 5.68 |
| found | 59.37 | 6.33 | 5.46 |

E) [[[4S-[4R*,8(R*),12R*]]-4-Carboxy-8-[1-carboxy-2-(4-hydroxyphenyl)ethyl]-5,11-bis(carboxymethyl)-1-phenyl-12-[(phenylmethoxy)methyl]-2-oxa-5,8,11-triazatridecan-13-oate(5-)]gadolinate(2-)]dihydrogen compound with 1-deoxy-1-methylamino-D-glucitol (1:2)

A 0.875 M solution of 1-deoxy-1-methylamino-D-glucitol (commercial product) (48.4 mL; 42.3 mmol) was dropped into a suspension of [4S-[4R*,8(R*),12R*]]-4-carboxy-8-[1-carboxy-2-(4-hydroxyphenyl)ethyl]-5,11-bis(carboxymethyl)-1-phenyl-12-[(phenylmethoxy)methyl]-2-oxa-5,8,11-triazatridecan-13-oic acid (14 mmol) in $H_2O$ (100 mL), stirring until complete dissolution. A 0.477 M solution of $GdCl_3$ (29.5 mL; 14 mmol) was slowly added maintaining the mixture at pH around 7 by addition of a 0.875 M solution of 1-deoxy-1-methylamino-D-glucitol (31.4 mL; 27.47 mmol). The resulting cloudy solution was stirred for 30 min at room temperature, then filtered over Millipore® (HA-0,22 μm). A 1M solution of HCl (28 mL; 28 mmol) was added to the clear solution under stirring until pH 2.0 was reached. The resulting precipitate was filtered, washed with water (5×40 mL) and then suspended in water (100 mL). The pH of the suspension was adjusted to neutrality by addition of a 0.875 M solution of 1-deoxy-1-methylamino-D-glucitol (25 mL; 22 mmol) stirring until complete dissolution of the acid complex. The neutral solution was evaporated (2 kPa) and the residue dried to give the title compound (15.2 g; 11.8 mmol). Yield 84%.

m.p.: 151° C.

HPLC: 94.5% (area %)—Chromatographic method:

Stationary phase: E. Merck Lichrospher 100 RP-18 5 μm; 250×4 mm column packed by E. Merck;

Temperature: 50° C.;

Mobile phase: isocratic elution with premixed mobile phase: 1 g of n-octylamine is added to 350 mL of acetonitrile mixed with 650 mL of water. The solution is buffered to pH 6 with $H_3PO_4$;

Flow rate: 1 mL min$^{-1}$;

Detection (UV): 210 nm;

Injection: 10 μL;

Sample concentration: 1 mg mL$^{-1}$;

Instrumentation: E. Merck—Hitachi L 6000 isocratic pump, E. Merck—Hitachi AS 2000 autosampler, Rheodyne 7414 six-port injection valve, E. Merck T 6300 column thermostat, E. Merck—Hitachi L 4250 UV detector.

MS and IR spectra were consistent with the structure.

Elemental analysis (%):

|  | C | H | N | Gd |
|---|---|---|---|---|
| calcd. | 47.68 | 5.97 | 5.54 | 12.24 |
| found | 47.85 | 6.03 | 5.46 | 12.11 |

EXAMPLE 12

Compound 7

[[[4S-[4R*,8(1R*,2R*),12R*]]-4-Carboxy-5,11-bis-(carboxymethyl)-8-[(1-carboxy-2-methyl)butyl]-1-phenyl-12-[(phenylmethoxy)methyl]-2-oxa-5,8,11-triazatridecan-13-oate(5-)]gadolinate(2-)]dihydrogen compound with 1-deoxy-1-(methylamino)-D-glucitol (1:2)

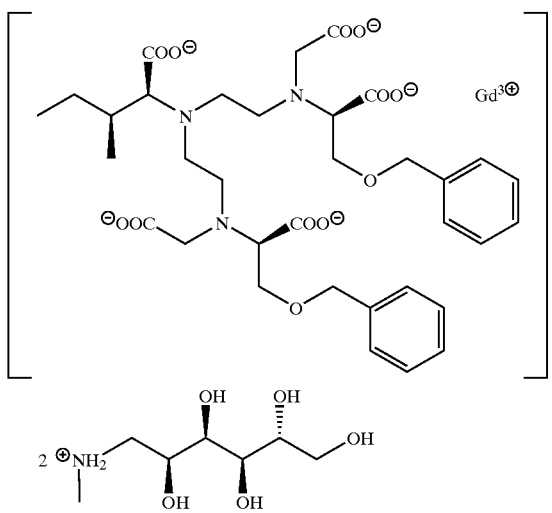

A) L-Isoleucine 1,1-dimethylethyl ester

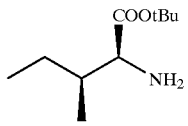

The product has been prepared according to Example 2, Step A.

B) N-(2-Bromoethyl)-N-[2-(1,1-dimethylethoxy)-2-oxoethyl]-O-(phenylmethyl)-L-serine 1,1-dimethylethyl ester The product has been prepared according to Example 5.

C) [4S-[4R*,8(1R*,2R*),12R*]]-4-[(1,1-Dimethylethoxy)-carbonyl]-8-[[1-[(1,1-dimethylethoxy)carbonyl]-2-methyl]-butyl]-5,11-bis[2-(1,1-dimethylethoxy)-2-oxoethyl]-1-phenyl-12-[(phenylmethoxy)methyl]-2-oxa-5,8,11-triazatridecan-13-oic acid 1,1-dimethylethyl ester

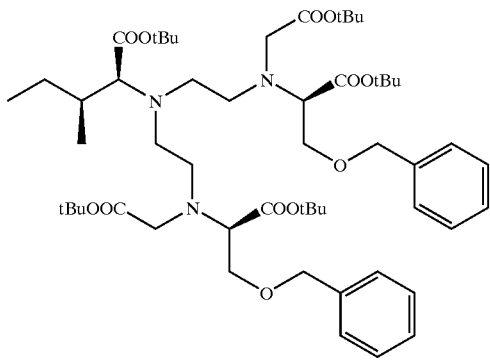

A 2 M pH 8 phosphate buffer (1710 mL) was added to a solution of N-(2-bromoethyl)-N-[2-(1,1-dimethylethoxy)-2-oxoethyl]-O-(phenylmethyl)-L-serine 1,1-dimethylethyl ester (181.69 g; 0.36 mol) and L-isoleucine 1,1-dimethylethyl ester (34.48 g; 0.17 mol) in $CH_3CN$ (1430 mL). After 23 h of vigorous stirring the two phases were separated and further 2 M pH 8 phosphate buffer (850 mL) was added to the organic phase. After 23 h the organic phase was separated and evaporated under reduced pressure (2 kPa). The residue was dissolved in $CH_2Cl_2$ (1700 mL) and the resulting solution was washed with water (850 mL), dried ($Na_2SO_4$) and concentrated to dryness (2 kPa). The crude (174.8 g) was purified by flash chromatography (Stationary phase: silica gel 230–400 mesh (1250 g); Eluent: 9:1 4:1 hexane/EtOAc gradient) to give the desired compound (150.6 g, 0.15 mol). Yield 91%.

HPLC: 92.5% (area %)—Chromatographic method:

Stationary phase: Merck KGaA Lichrosorb RP-Select B 5 μm;

250×4 mm column packed by Merck KGaA;

Temperature: 35° C.;

Mobile phase: gradient elution;

A=0.017 M $H_3PO_4$ in water

B=$CH_3CN$

| Gradient timetable: | min | % A | % B |
|---|---|---|---|
| | 0 | 70 | 30 |
| | 40 | 20 | 80 |
| | 50 | 20 | 80 |

Flow rate: 1 mL $min^{-1}$;

Detection (UV): 210 nm;

Injection: 10 μL;

Sample concentration: 1 mg $mL^{-1}$;

Instrumentation: Merck KGaA—Hitachi L 6200 low pressure gradient pump, Merck KGaA—Hitachi AS 2000 autosampler, Merck KGaA T6300 column thermostat, Merck KGaA—Hitachi L 3000 diode array detector.

TLC: Rf=0.38

Silica gel plates 60 $F_{254}$ (Merck KGaA art. 5715)

Eluent: 4: 1 hexane/EtOAc

Detection: UV (254 nm) and 1% $KMnO_4$ in 1 M NaOH $^{13}$C-NMR, $^1$H-NMR and MS spectra were consistent with the structure.

K.F.: 0.33%

Elemental analysis (%):

| | C | H | N |
|---|---|---|---|
| calcd. | 66.84 | 9.06 | 4.33 |
| found | 66.14 | 8.97 | 4.25 |

D) [4S-[4R*8(1R*,2R*),12R*]]-4-Carboxy-5,11-bis (caroxymethyl)-8-[(1-carboxy-2-methyl)butyl]-1-phenyl-12-[(phenylmethoxy)methyl]-2-oxa-5,8,11-triazatridecan-13-oic acid

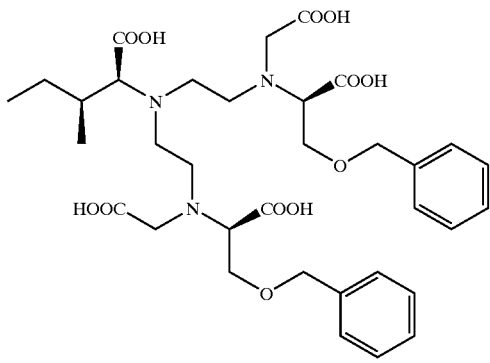

CF$_3$COOH (35.9 mL; 53.4 g; 0.47 mol) was added to a solution of the pentaester from the previous preparation (124 g; 0.128 mmol) in CH$_2$Cl$_2$ (540 mL) maintaining the temperature at 0:5° C. The resulting solution was evaporated (2 kPa) and the residue was dissolved in CF$_3$COOH (1070 mL; 1600 g; 14.04 mol). The solution was stirred at room temperature for 69 h and then evaporated to dryness (2 kPa). The crude (215.8 g) was dissolved in a 1:1 MeOH/H$_2$O mixture (670 mL) and loaded onto a column of Amberlite XAD 1600 polystyrene resin (1.9 L). After elution with 7/3 MeOH/H$_2$O the crude ligand was obtained (71.4 g). The product was dissolved in H$_2$O (300 mL) and the pH adjusted to 11 with 10 N NaOH (42.15 mL; 0.42 mol). The solution was maintained at pH 11 for 16 h by the slow addition of 10 N NaOH (6.26 mL; 62.6 mmol) through a pH-stat apparatus. Acidification of the mixture to pH 2 with 1 N HCl led to the formation of a precipitate which was filtered, washed with H$_2$O and dried to give the desired compound (63 g; 91.3 mmol). Yield 72%.

m.p.: 108–110° C.
Acidic titer (0.1 N NaOH): 99.7%
Complexometric titer (0.1 N ZnSO$_4$): 96.7%
HPLC: 96.0% (area %)—Chromatographic method:
Stationary phase: Lichrosorb RP-Select B 5 μm;
250×4 mm column packed by Merck KGaA;
Temperature: 35° C.;
Mobile phase: isocratic elution: A/B=55:45
A=0.017 M H$_3$PO4 in water
B=CH$_3$CN
Flow rate: 1 mL min$^{-1}$;
Detection (UV): 210 nm;
Injection: 10 μL;
Sample concentration: 1 mg mL$^{-1}$;
Instrumentation: Merck KGaA—Hitachi high pressure gradient pump system (two Lachrom L 7100 pumps), Merck KGaA—Hitachi Lachrom L 7200 autosampler, Merck KGaA—Hitachi Lachrom L 7300 column thermostat, Merck KGA—Hitachi Lachrom L 7400 UV detector.
K.F.: 1.80%
$^{13}$C-NMR, $^1$H-NMR, MS and IR spectra were consistent with the structure.
[α]$_D^{20}$: −26.03° (c 2.01, 0.4 N NaOH)

Elemental analysis (%):

|  | C | H | N |
|---|---|---|---|
| calcd. | 59.21 | 6.87 | 6.09 |
| found | 59.68 | 6.80 | 6.15 anhydrous |

E) [[[4S-[4R*,8(1R*,2R*),12R*]]-4-Carboxy-5,11-bis-caroxymethyl)-8-[(1-carboxy-2-methyl)butyl]-1-phenyl-12-[(phenylmethoxy)methyl]-2-oxa-5,8,11-triazatridecan-13-oate(5-)]gadolinate(2-)]dihydrogen compound with 1-deoxy-1-(methylamino)-D-glucitol (1:2)

A 1 M aqueous solution of 1-deoxy-1-(methylamino)-D-glucitol (120 mL; 120 mmol) was dropped into a suspension of the free ligand from the previous preparation (27.6 g; 40 mmol) in H$_2$O (200 mL), stirring until a clear solution was obtained. A solution of GdCl$_3$.6 H$_2$O (14.9 g; 40 mmol) in H$_2$O (50 mL) was slowly added, maintaining the mixture at pH 7 by addition of a 1 N aqueous solution of 1-deoxy-1-(methylamino)-D-glucitol (75.28 mL; 75.28 mmol) by means of a pH-stat apparatus. The reaction mixture was filtered through a Millipore HA 0.45 mm filter and then nanofiltered:

UNIT 123 (Celfa)
Membrane: DESAL DK 4040
Pressure: 1 MPa
Retentate
max conductivity: 12 mS/cm
final conductivity: 3.5 mS/cm
volume: 0.3 L
Permeate
max conductivity: 3.3 mS/cm
final conductivity: 0.04 mS/cm
volume: 5.23 L
Time: 18 h After adjusting the pH at 7 by adding a 1 N aqueous solution of 1-deoxy-1-(methylamino)-D-glucitol (0.15 mL; 0.15 mmol), the retentate was loaded onto a column of Amberlite XAD 1600 polystyrene resin (40 mL) which was eluted with H$_2$O (500 mL). The eluate was freeze dried and then further dried (P$_2$O$_5$, 40° C., 2 kPa) to give the title compound (42.8 9; anhydrous 40.7 g; 33 mmol). Yield 83%.

m.p.: 114–115° C.
Free ligand (0.001 M GdCl$_3$): 0.2%
HPLC: 98% (area %)—Chromatographic method:
Stationary phase: Eka Nobel Kromasil C4 5 μm;
250×4 mm column packed by Bishoff;
Temperature: 50° C.;
Mobile phase: gradient elution;
A=aqueous solution containing 1 g L$^{-1}$ n-hexylamine buffered at pH 6 with H$_3$PO$_4$ and 33% v/v CH$_3$CN
B=aqueous solution containing 1 g L$^{-1}$ n-hexylamine buffered at pH 6 with H$_3$PO$_4$ and 55S% v/v CH$_3$CN

| Gradient timetable: | min | % A | % B |
|---|---|---|---|
|  | 0 | 100 | 0 |
|  | 10 | 100 | 0 |
|  | 20 | 0 | 100 |
|  | 35 | 0 | 100 |

Flow rate: 1 mL min$^{-1}$;
Detection (UV): 210 nm;

Injection: 10 μL;
Sample concentration: 1 mg mL$^{-1}$;
Instrumentation: Hewlett-Packard HP 1090 M liquid chromatograph equipped with DR 5 solvent delivery system, autosampler, column thermostat and diode array detector.
K.F.: 4.80%
MS and IR spectra were consistent with the structure.
[α] −27.26° (c 2.01, H$_2$O)
Elemental analysis (%):

|  | C | H | N | Gd |
|---|---|---|---|---|
| calcd. | 46.70 | 6.37 | 5.67 | 12.74 |
| found | 46.70 | 6.14 | 5.77 | 13.00 anhydrous |

EXAMPLE 13

Compound 8

[[[4S-[4R*,8(1R*,2R*)]]-4-Carboxy-5,11-bis(carboxymethyl)-8-[(1-carboxy-2-methyl)butyl]-1-phenyl-12-[(phenylmethoxy)methyl]-2-oxa-5,8,11-triazatridecan-13-oate(5-)]gadolinate(2-)]disodium salt (1:2)

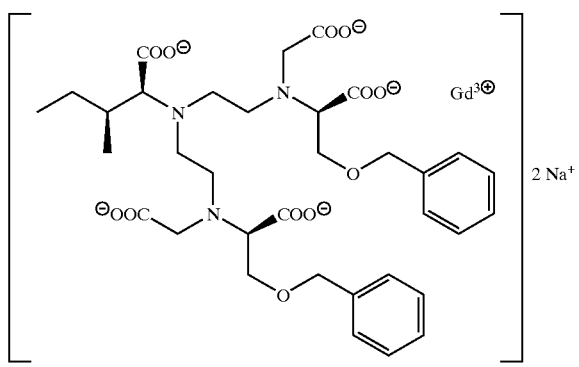

10 N NaOH (4.696 mL; 46.9 mmol) was dropped into a suspension of the free ligand obtained in Example 12, Step (D) (10.35 g; 15 mmol) in H$_2$O (150 mL) stirring until a clear solution was obtained. A solution of GdCl$_3$.6 H$_2$O (5.6 g; 15 mmol) in H$_2$O (50 mL) was slowly added maintaining the mixture at pH 7 by addition of 10 N NaOH (2.546 mL; 25.4 mmol) by means of a ph-stat apparatus. The reaction mixture was filtered through a Millipore HA 0.45 μm filter and then nanofiltered:
UNIT 123 (Celfa)
Membrane: DESAL DK 4040
Pressure: 1 MPa
Retentate
max. conductivity: 6.2 mS/cm
final conductivity: 2.5 mS/cm
volume: 0.3 L
Permeate
max. conductivity: 2.2 mS/cm
final conductivity: 0.04 mS/cm
volume: 5.5 L
Time: 18 h
After adjusting the pH to 7 by adding 2 N NaOH (0.05 mL; 0.10 mmol) the retentate was evaporated in vacuo (2 kPa) to give the title compound (8.4 g; anhydrous 7.96 g; 8.97 mmol). Yield 60%.
m.p.: 150–152° C.(synt.)
Free ligand (0.001 M GdCl$_3$): 0.1%
HPLC: 97% (area %)—Chromatographic method of Example 12, E).
K.F.: 5.21%
MS and IR spectra were consistent with the structure.
[α]$_D^{20}$ −28.29° (c 2.06, H$_2$O)
Elemental analysis (%):

EXAMPLE 14

Compound 9

[[[4S-[(4R*,8(R*),12R*]]-4-Carboxy-5,11-bis(carboxymethyl)-8-(1-carboxy-pentyl)-1-phenyl-12-[(phenylmethoxy)methyl]-2-oxa-5,8,11-triazatridecan-13-oate(5-)]-gadolinate(2-)]disodium salt

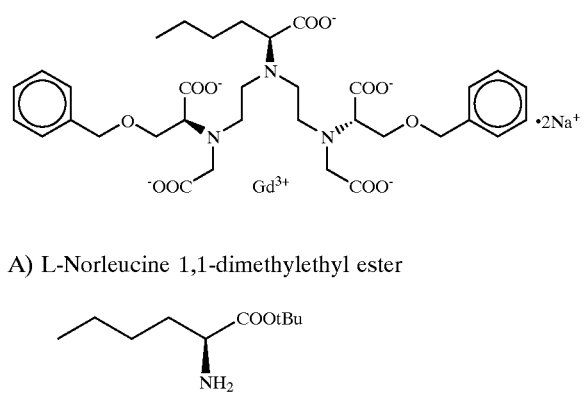

A) L-Norleucine 1,1-dimethylethyl ester

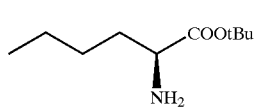

To a suspension of L-norleucine (commercial product) (13.1 g; 0.1 mol) in t-butyl acetate (600 mL; 4.45 mol) maintained at 20° C., 70% aq. HClO$_4$ (10.3 mL; 0.12 mol) was added in 10 min. The reaction was maintained at r.t. for 7 h. Saturated aq. Na$_2$CO$_3$ was slowly added until pH 9 was reached and the organic phase was separated and concentrated. The oily residue was dissolved in Et$_2$O (250 mL) and extracted with 1N HCl (120 mL). The aqueous phase was basified to pH 10 with 1 N NaOH and extracted with Et$_2$O (400 mL). The organic layer, dried over Na$_2$SO$_4$, was concentrated to give the desired compound (14.3 g; 76.4 mmol). Yield 76%.
TLC: R$_f$=0.36
Stationary phase: silica gel plates 60 F$_{254}$
Eluent: 9:1 CHCl$_3$/CH$_3$OH
Detection: 0.5% KMnO$_4$ in 1N NaOH
$^{13}$C-NMR, $^1$H-NMR, MS and IR spectra were consistent with the structure.
B) N-(2-Bromoethyl)-N-[2-(1,1-dimethylethoxy)-2-oxoethyl]-O-(phenylmethyl)-L-serine 1,1-dimethylethyl ester
The product has been prepared according to Example 5.
C) [4S-[4R*,8(R*),12R*]]-4-[(1,1-Dimethylethoxy)carbonyl]-8-[1-[(1,1-dimethylethoxy)carbonyl]pentyl]-5,11-bis-[2-(1,1-dimethylethoxy)-2-oxoethyl]-1-phenyl- 12-[(phenylmethoxy)methyl]-2-oxa-5,8,11-triazatridecan-13-oic acid 1,1-dimethylethyl ester

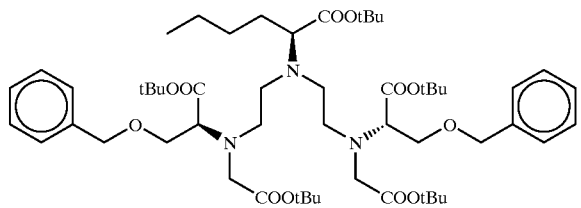

To a solution of L-norleucine 1,1-dimethylethyl ester (4.7 g; 25 mmol) and N-(2-bromoethyl)-N-[2-(1,1-dimethylethoxy)-2-oxoethyl]-O-(phenylmethyl)-L-serine 1,1-dimethylethyl ester (28 g; 60 mmol) in $CH_3CN$ (100 mL) 2M pH 8 phosphate buffer (250 mL) was added. The biphasic mixture was maintained under vigorous mechanical stirring for 16 h. The organic layer was separated and concentrated. The oily residue was purified by flash chromatography (n-hexane/EtOAc 9:1 v/v) to give the desired compound (23.6 g; 24.32 mmol). Yield 97%.

TLC: $R_f$=0.67
Stationary phase: silica gel plates 60 $F_{254}$
Eluent: 8:2 n-hexane/EtOAc
Detection: 254 nm; 0.5% $KMnO_4$ in 1N NaOH
$^{13}C$-NMR, $^1H$-NMR, MS and IR spectra were consistent with the structure.

D) [4S-[4R*,8(R*),12R*]]-4-Carboxy-5,11-bis(carboxymethyl)-8-(1-carboxypentyl)-1-phenyl-12-[(phenyl-methoxy)methyl]-2-oxa-5,8,11-triazatridecan-13-oic acid

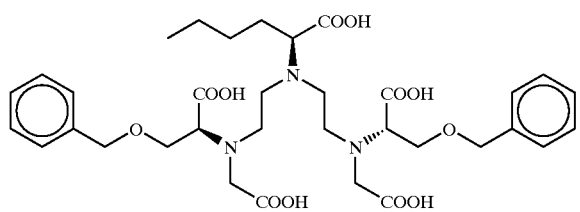

To a solution of the pentaester from the previous preparation (19.4 g; 19.99 mmol) in $CHCl_3$ (300 mL), maintained at 0–5° C. under an inert atmosphere, $(CH_3)_3SiI$ (40 g; 0.2 mol) was added in 2 h. The solution was allowed to rise to room temperature and left under stirring for 40 h. The solution was cooled to 0–5° C. and $H_2O$ (150 mL) was added. After separation the pH of the aqueous layer was adjusted to pH 3.5 with 4N NaCH. The cloudy solution was loaded onto a column of resin Amberlite® XAD 1600 (600 mL) and eluted with $H_2O$ (5 L) and then with $H_2O/CH_3CN$ (gradient elution 90:10 60:40 v/v ratios). The free ligand (9.87 g; 14.3 mmol) was obtained. Yield 72%.

mp: 100–103° C.
HPLC: 100% (area %)—Chromatographic method:
Stationary phase: Lichrospher 100 RP-8 5 µm;
250×4 mm column packed by Merck KGaA;
Temperature: 40° C.;
Mobile phase: isocratic elution with premixed mobile phase: 1 g of n-octylamine is added to 300 mL of acetonitrile mixed with 700 mL of water.
The solution is buffered to pH 6 with $H_3PO_4$;
Flow rate: 1 mL min$^{-1}$;
Detection (UV): 200 nm;
Injection: 10 µL;
Sample concentration: 1 mg mL$^{-1}$;

Instrumentation: Merck KGaA—Hitachi high pressure gradient pump system (L6200 and L6000), Merck KGA—Hitachi AS 2000 autosampler, Merck KGaA T 6300 column thermostat, Merck KGaA—Hitachi L 4250 UV detector.
CE: 98.5% (area %)—Electrophoretic method:
Capillary: fused silica 0.56 m×75 µm with bubble cell;
Voltage: 25 kV;
Buffer: 0.05 M borate pH 9.3, EDTA 0.3 mM;
Temperature: 40° C.;
Stoptime: 20 min;
Detection (UV): 200–210 nm;
Injection: hydrostatic (50 mbar, 5 s);
Sample concentration: 1 mg mL$^{-1}$;
Instrumentation: Hewlett Packard 3D HPCE

| Preconditioning timetable: | t (min) | action |
|---|---|---|
| | 0 | flush with $H_2O$ |
| | 2 | flush with 0.1 M NaOH |
| | 4 | flush with $H_2O$ |
| | 5 | flush with buffer |
| | 9 | start analysis |

$^{13}C$-NMR, $^1H$-NMR, MS and IR spectra were consistent with the structure.
K.F.: <0.1%
Elemental analysis (%)

| | C | H | N | Na |
|---|---|---|---|---|
| Calcd. | 59.21 | 6.87 | 6.09 | — |
| Found | 58.85 | 7.26 | 5.84 | 0.11 |

E) [[[4S-[4R*,8(R*),12R*]]-4-Carboxy-5,11-bis(carboxymethyl)-8-(1-carboxy-pentyl)-1-phenyl-12-[(phenyl-methoxy)methyl]-2-oxa-5,8,11-triazatridecan-13-oate(5-)]-gadolinate(2-)]disodium salt To a suspension of the free ligand from the previous preparation (4.5 g; 6.52 mmol) in $H_2O$ (70 mL), maintained at 5° C., 1N NaOH (13 mL) was added until a clear solution was obtained. A 0.22M solution of $GdCl_3$ (29.7 mL; 6.54 mmol) was slowly added (1 h), maintaining the mixture at pH 7 by addition of 1N NaOH. The solution was stirred for 1 h at room temperature, filtered over Millipore GSWP 0,22 m, and loaded onto a column of Amberlite XAD 1600 polystyrene resin (500 mL), which was eluted with $H_2O$ (1500 mL) and then with $H_2O/CH_3CN$ (2 L; 80:20 v/v). The title compound (5.2 g; 5.86 mmol) was obtained. Yield 90%.
mp: >250° C.
HPLC: 100% (area %) Chromatographic method of Example 3, A).
CE: 99.5% (area) Electrophoretic method of previous Step D)
Free ligand (0.001 M $GdCl_3$): <0.1%
MS and IR spectra were consistent with the structure.
K.F.: 6.05%
Weight loss (130° C.): 6.05%
Elemental analysis (after drying at 130° C.) (%):

| | C | H | N | Gd | Na |
|---|---|---|---|---|---|
| calcd. | 45.99 | 4.77 | 4.73 | 17.71 | 5.18 |
| found | 46.00 | 4.78 | 4.69 | 17.59 | 5.25 |

EXAMPLE 15

Compound 10

[[[4S-[4R*,8(R*),12R*]]-4-Carboxy-5,11-bis(carboxymethyl)-8-[1,3-bis(carboxy)propyl]-1-phenyl-12-[(phenylmethoxy)methyl]-2-oxa-5,8,11-triazatridecan-13-oate-(6-)]gadolinate(3-)] trihydrogen compound with 1-deoxy-1-(methylamino)-D-glucitol (1:3)

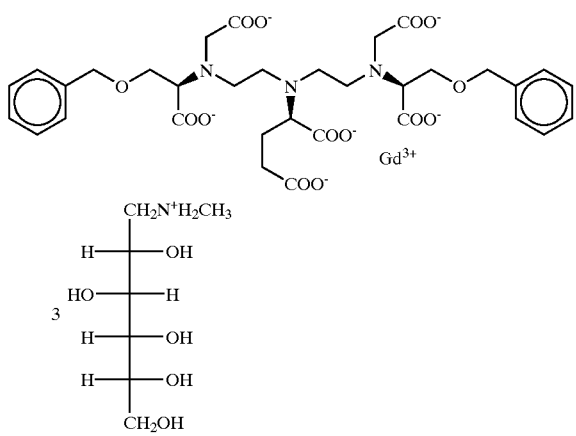

A) L-Glutamic acid bis(1,1-dimethylethyl) ester

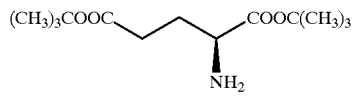

Acetic acid 1,1-dimethylethyl ester (1742 g; 2 L; 15 mol) (commercial product), 70% aq. perchloric acid (51 mL; 0.59 mol) and L-glutamic acid (78.8 g; 0.54 mol) (commercial product) were stirred at 25° C. over 5 days. After addition of a solution of $K_2CO_3$ (41.46 g, 0.3 mol) in $H_2O$ (140 mL) to the reaction mixture, the organic phase was separated, washed with water (2×500 mL), dried ($NaSO_4$) and concentrated to dryness. The residue (27.2 g) was dissolved in $Et_2O$ (200 mL) and extracted with 1N HCl (2×70 mL), the combined aqueous phase was washed with $Et_2O$ (40 mL) and collected with the aqueous phases previously obtained from the first neutralization and successive washings. Addition of 10 N NaOH up to pH 8.8 led to an emulsion which was extracted with $Et_2O$ (2×600 mL). The combined organic phases were washed with $H_2O$ (250 mL), dried and evaporated to give the desired compound (57.7 g; 0.22 mol). Yield 41%.

Acidic titer (0.1 N HCl): 99,8%
Acidic titer (0.1 N $HClO_4$ in $CH_3COOH$): 99,1%
GC: 99.4% (area %)—Gaschromatographic method:
Stationary phase: DB 5 (OV-73 );
Film thickness: 0.25 μm;
Column (WCOT): 30 m×0.25 mm;
Carrier (He)
flow rates:
    column flow rate: 0.9 mL min$^{-1}$;
    split flow rate: 100 mL min$^{-1}$;
    make up flow rate: 30 mL min$^{-1}$;
    septum purge flow rate: 3 mL min$^{-1}$;
Detector (FID) feeding:
hydrogen pressure: 1.2 bar;
air pressure: 2.8 bar;

Oven temperature timetable:
initial temperature: 120° C.;
initial time: 2 min;
rate: 10° C. min$^{-1}$;
final temperature: 270° C.;
final time: 5 min;
Injector temperature: 150° C.;
Detector temperature: 200° C.;
Injection: 1 μL;
Sample concentration: 25 mg mL$^{-1}$;
Instrumentation: Hewlett-Packard HP 5890.
$[\alpha]_D^{20}$: +20.83° (c 2.0; MeOH)
$^{13}C$-NMR, $^1H$-NMR and MS spectra were consistent with the structure.
Elemental analysis (%):

|  | C | H | N |
|---|---|---|---|
| Calcd. | 60.20 | 9.72 | 5.40 |
| Found | 60.33 | 9.70 | 5.35 |

B) N-(2-Bromoethyl)-N-[2-(1,1-dimethylethoxy)-2-oxoethyl]-O-(phenylmethyl)-L-serine The product has been prepared according to Example 5.

C) [4S-[4R*,8(R*),12R*]]-4-[(1,1-Dimethylethoxy)-carbonyl]-8-[4-(1,1-dimethylethoxy)-1-[(1,1-dimethylethoxy)carbonyl]-4-oxobutyl]-5,11-bis[2-(1,1-dimethyl-ethoxy)-2-oxoethyl]-1-phenyl-12-[(phenylmethoxy)methyl]-2-oxa-5,8,11-triazatridecan-13-oic-acid 1,1-dimethylethyl ester

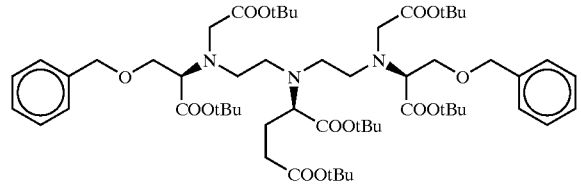

Phosphate buffer 2 M, pH 8 (1700 mL) was added to a solution of N-(2-bromoethyl)-N-[2-(1,1-dimethylethoxy)-2-oxoethyl]-O-(phenylmethyl)-L-serine 1,1-dimethylethyl ester (171.2 g; 0.36 mol) and L-glutamic acid bis(1,1-dimethylethyl) ester (44.1 g; 0.17 mol) in $CH_3CN$ (1450 mL). After 15 h of vigorous stirring the two phases were separated and further 2 M pH 8 phosphate buffer (900 mL) was added to the organic phase. After 27 h the organic phase was separated and evaporated under reduced pressure (2 kPa). The residue was dissolved in $CH_2Cl_2$ (1700 mL) and the resulting solution was washed with water (900 mL), dried ($Na_2SO_4$) and concentrated. The crude was dissolved in n-hexane (1000 mL) to give a precipitate ($Ph_3P=O$) which was filtered off. The solution was evaporated to dryness (2 kPa) and the residue was purified by flash chromatography (Stationary phase: silica gel 230–400 mesh ASTM; Eluent: n-hexane and from 9: 1 to 5.7: 1 n-hexane/EtOAc) to give the desired product (154 g, 0.15 mol). Yield 87%.

Acidic titer (0.1 N HCl): 100.0%
HPLC: 96.2% (area %)—Chromatographic method:
Stationary phase: Merck KGaA Lichrosorb RP-Select B 5 μM;
250×4 mm column packed by Merck KGaA;
Temperature: 35° C.;

Mobile phase: gradient elution;
A=0.017 M H₃PO₄ in water
B=CH₃CN

| Gradient timetable: | min | % A | % B |
|---|---|---|---|
| | 0 | 70 | 30 |
| | 40 | 20 | 80 |
| | 50 | 20 | 80 |

Flow rate: 1 mL min$^{-1}$;
Detection (UV): 210 nm;
Injection: 10 μL;
Sample concentration: 1 mg mL$^{-1}$;
Instrumentation: Merck KGaA—Hitachi L 6200 low pressure gradient pump, Merck KGaA—Hitachi AS 2000 autosampler, Merck KGaA T6300 column thermostat, Merck KGaA—Hitachi L 3000 diode array detector.
TLC: Rf=0.36
Silica gel plates 60 F$_{254}$
Eluent: 4:1 n-hexane/EtOAc
Detection: UV (254 nm) and 1% KMnO₄ in 1 M NaOH
Weight loss (60° C.): <0.10%
$^{13}$C-NMR, $^1$H-NMR, MS and IR spectra were consistent with the structure.
[α]$_D^{20}$: −31.26° (c 5.03, CHCl₃)
Elemental analysis (%):

| | C | H | N |
|---|---|---|---|
| calcd. | 65.68 | 8.79 | 4.03 |
| found | 65.78 | 9.11 | 4.10 |

D) [4S-[4R*,8(R*),12R*]]-4-Carboxy-5,11-bis(carboxymethyl)-8-[1,3-bis(carboxy)propyl]-1-phenyl-12-[(phenylmethoxy)methyl]-2-oxa-5,8,11-triazatridecan-13-oic acid

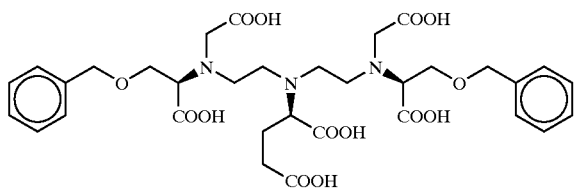

CF₃COOH (40.6 mL; 60.5 g; 0.53 mol) was added to a solution of the hexaester from the previous preparation (151.7 g; 0.14 mol) in CH₂Cl₂ (530 mL) maintaining the temperature at 0–5° C. The resulting solution was evaporated (2 kPa), the residue was dissolved in CF₃COOH (264 mL; 393 g; 3.45 mol) and the solution stirred at room temperature for 15 h. After evaporation (2 kPa) the residue was again dissolved in CF₃COOH (100 mL; 150 g; 1.3 mol) in order to complete the reaction. The resulting mixture was stirred at room temperature for 14 h and then evaporated under reduced pressure (2 kPa). The crude (243.7 g) was dissolved in 1:5 CH₃CN/H₂O (550 mL) and loaded onto a column of Amberlite XAD 1600 polystyrene resin (1.9 L) which was eluted with CH₃CN/H₂O to give the desired compound (89.2 g; anhydrous 87.2 g; 0.124 mol). Yield 85%.
m.p.: 109–110° C.
Acidic titer (0.1 N NaOH): 100.9%
Complexometric titer (0.1N ZnSO₄): 98.8%
HPLC: 97.4% (area %) Chromatographic method of previous Step C).
Weight loss (90° C.): 2.29%
$^{13}$C-NMR, $^1$H-NMR, MS and IR spectra were consistent with the structure.
[α]$_D^{20}$: −17.07° (c 2.06, 0.4 M NaOH)
Elemental analysis (%):

| | C | H | N |
|---|---|---|---|
| calcd. | 56.16 | 6.14 | 5.95 |
| found | 56.61 | 6.29 | 6.07 anhydrous |

E) [[[4S-[4R*,8(R*),12R*]]-4-Carboxy-5,11-bis(carboxymethyl)-8-[1,3-bis(carboxy)propyl]-1-phenyl-12-[(phenylmethoxy)methyl]-2-oxa-5,8,11-triazatridecan-13-oate-(6-)]gadolinate(3-)]trihydrogen compound with 1-deoxy-1-(methylamino)-D-glucitol (1:3)

A 1 M aqueous solution of 1-deoxy-1-(methylamino)-D-glucitol (154 mL; 0.154 mol) was dropped into a suspension of the product from the previous preparation (28.2 g; 0.040 mol) in H₂O (150 mL), stirring until a clear solution was obtained. A solution of GdCl₃.6 H₂O (14.9 g; 0.040 mol) in H₂O (40 mL) was slowly added maintaining the mixture at pH 7 by addition of a 1 M aq solution of 1-deoxy-1-(methylamino)-D-glucitol (91.5 mL; 0.092 mol) by means of a pH-stat apparatus. The reaction mixture was filtered through a Millipore HA 0.45 μfilter and then nanofiltered:
UNIT 123 (Celfa)
Membrane: DESAL DK 4040
Pressure: 1 MPa
Retentate
max conductivity: 11.5 mS/cm
final conductivity: 5.1 mS/cm
volume: 0.3 L
Permeate
max conductivity: 3.0 mS/cm
final conductivity: 0.13 mS/cm
volume: 2.8 L
Time: 15 h
The retentate (pH 7.1) was freeze dried at first and then further dried (P₂O₅, 2 kPa) to give the title compound (52.4 g; anhydrous 51.8 g; 0.036 mol). Yield 90%.
m.p.: 116–118° C.
Free ligand (0.001 M GdCl₃): <0.10%
HPLC: 97% (area %)—Chromatographic method:
Stationary phase: Spheri −10 RP-2 10 μm;
250×4, 6 mm column packed by Applied Biosystem;
Temperature: 40° C.;
Mobile phase: isocratic elution: A/B=80:20
A=1 g of n-octylamine is added to 1000 mL of water. The solution is buffered to pH=6 with H₃PO₄;
B=CH₃CN
Flow rate: 1.0 mL min$^{-1}$;
Detection (UV): 210 nm;
Injection: 10 μL;
Sample concentration: 1 mg mL$^{-1}$;
Instrumentation: Merck KGaA—Hitachi high pressure gradient pump system (two Lachrom L 7100 pumps), Merck KGaA—Hitachi Lachrom L 7200 autosampler, Merck KGaA—Hitachi Lachrom L 7300 column thermostat, Merck KGaA—Hitachi Lachrom L 7400 UV detector.

K.F.: 1.21%
MS and IR spectra were consistent with the structure.
$[\alpha]_D^{20}$: −24.29° (c 2.01, $H_2O$)
Elemental analysis (%):

|  | C | H | N | Gd |  |
|---|---|---|---|---|---|
| calcd. | 44.87 | 6.34 | 5.81 | 10.88 |  |
| found | 44.62 | 6.44 | 5.80 | 10.79 | anhydrous |

EXAMPLE 16

Compound 11

[[[N,N'-[[(Carboxymethyl)imino]di-2,1-ethanediyl]
bis[N-(carboxymethyl)-L-phenylalaninate]](5-)]
gadolinate(2-)]dihydrogen compound with 1-deoxy-
1-(methylamino)-D-glucitol (1:2)

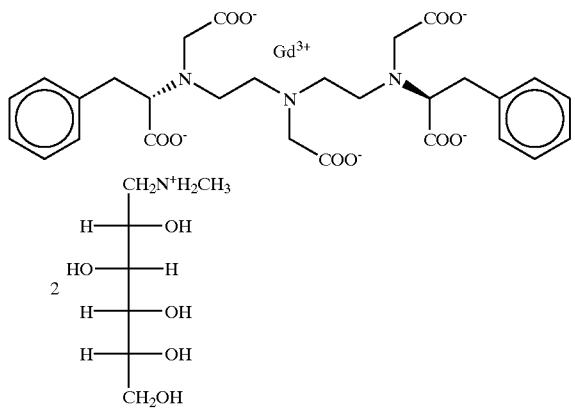

A) N-(2-bromoethyl)-N-[2-(1,1-dimethylethoxy)-2-
oxoethyl]-L-phenylalanine 1,1-dimethylethyl ester
The product is prepared according to Example 3.

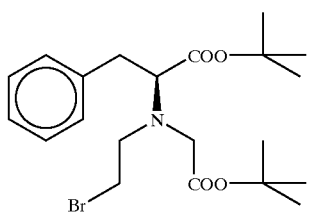

B) Glycine 1,1-dimethylethyl ester

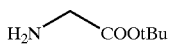

The product is prepared according to Example 1.

C) N,N'-[[[2-(1,1-Dimethylethoxy)-2-oxoethyl]imino]di-2,
1-ethanediyl]bis[N-[2-(1,1-dimethylethoxy)-2-oxoethyl]-
L-phenylalanine 1,1-dimethylethyl ester]

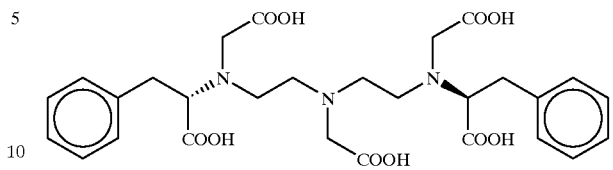

A two phase mixture of N-(2-bromoethyl)-N-[2-(1,1-dimethylethoxy)-2-oxoethyl]-L-phenylalanine 1,1-dimethylethyl ester (116.4 g; 0.221 mol) and glycine 1,1-dimethylethyl ester (13.6 g; 0.104 mol) in MeCN (1000 mL) and 2 M pH 8 phosphate buffer (600 mL) was stirred for 20 h. The upper layer was separated and replaced with fresh 2 M pH 8 phosphate buffer (400 mL). The reaction mixture was stirred for additional 14 h. The upper layer was separated and the solvent evaporated. The residue was dissolved in n-hexane (500 mL) and the solution washed with $H_2O$ (400 mL). After drying ($Na_2SO_4$), the solvent was evaporated under reduced pressure (2 kPa) and the residue (107 g) purified by flash chromatography:
Sample: Solid dispersion in silica gel 35–70 mesh
Stationary phase: 1200 g Silica gel 230–400 mesh
Stationary phase conditioning: n-hexane

| (v/v) | Volume (L) |
|---|---|
| 100/0 | 1.5 |
| 95/5 | 1 |
| 92.5/7.5 | 2 |
| 90/10 | 2 |
| 87.5/12.5 | 2 |
| 85/15 | 6.5 |

After further drying ($P_2O_5$; 0.13 kPa; 50° C.) the desired product was obtained (71.9 g; 0.084 mol). Yield 81%.
Acidic titer (0.1 N HCl): 98.2%
TLC: Rf 0.3
Stationary phase: Silica gel plates 60 $F_{254}$
Eluent: 4:1 (v/v) n-Hexane/EtOAc
Detection: 1% $KMnO_4$ in 1 N NaOH
HPLC: 98.5% (area %) Chromatographic method:
Stationary phase: Lichrosorb RP-Select B 5 mm;
250×4 mm column packed by Merck KGaA;
Temperature: 45° C.;
Mobile phase: gradient elution;
A=0.017 M $H_3PO_4$ in water
B=$CH_3CN$

| Gradient timetable: | min | % A | % B |
|---|---|---|---|
|  | 0 | 82 | 18 |
|  | 30 | 15 | 85 |
|  | 45 | 15 | 85 |

Flow rate: 1 mL $min^{-1}$;
Detection (UV): 210 nm;
Injection: 10 μL;
Sample concentration: 1 mg $mL^{-1}$;
Instrumentation: Merck KGA—Hitachi L 6200 low pressure gradient pump, Merck KGaA—Hitachi AS 2000 autosampler, Merck KGaA T6300 column thermostat, Merck KGaA—Hitachi L 3000 diode array detector.

Weight loss (70° C. high vacuum): 0.66%

$^{13}$C-NMR, $^1$H-NMR, MS and IR spectra were consistent with the structure.

$[\alpha]_{80}{}^{20}$ (c 5.12; CHCl$_3$)

| λ(nm) | 589 | 578 | 546 | 436 | 405 | 365 |
|---|---|---|---|---|---|---|
| $[\alpha]_\lambda{}^{20}$ | −19.56° | −20.55° | −23.52° | −42.18° | −51.58° | −71.27° |

Elemental analysis (%);

|  | C | H | N |
|---|---|---|---|
| Calcd. | 67.50 | 8.85 | 4.92 |
| Found | 67.27 | 8.82 | 4.98 |

D) N,N'-[[(Carboxymethyl)imino]di-2,1-ethanediyl]-bis[N-(carboxymethyl)-L-phenylalanine]

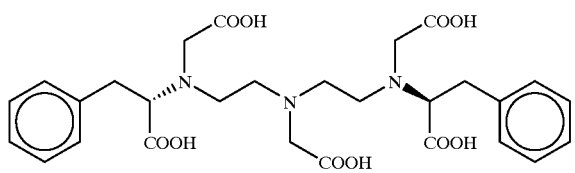

Trifluoroacetic acid (96.3 g; 0.845 mol) was dripped, over 30 min, into a solution of the product obtained at the previous step (33.3 g; 0.039 mol) in CH$_2$Cl$_2$ (20 mL) stirred at −15+−10° C. The cooling bath was removed and the reaction stirred at room temperature for 64 h. The solvent was removed by evaporation under reduced pressure (2 kPa) and the residue taken up with fresh trifluoroacetic acid (96.3 g; 0.845 mol). After additional 26 h stirring, the reaction mixture was evaporated under reduced pressure (2 kPa) obtaining a brown oil that was dissolved in CH$_2$Cl$_2$ (100 mL) and again evaporated in vacuo. This operation was repeated twice. Following the same procedure the residue was treated with Et$_2$O (200 mL) and then with CH$_3$CN (50 mL) obtaining a brownish amorphous solid that was dissolved in 1/1 (v/v) CH$_3$CN/H$_2$O (50 mL) acidified with 37% HCl (10 mL) and diluted to 200 mL with H$_2$O. The solution was loaded onto a column of Amberlite® XAD 1600 (1 L) and the product eluted with a H$_2$O/CH$_3$CN gradient:

Conditioning: 90/10 (v/v) H$_2$O/CH$_3$CN
Elution: H$_2$O/CH$_3$CN gradient

| (v/v) | Volume (L) |
|---|---|
| 90/10 | 3.5 |
| 80/20 | 2.5 |
| 75/25 | 1.5 |
| 70/30 | 1.5 |
| 65/35 | 1.5 |
| 60/40 | 1 |
| 40/60 | 1 |
| 20/80 | 1.5 |

The product elutes with 75/25 (v/v) H$_2$O/CH$_3$CN.

Fractions containing the pure ligand were collected and evaporated in vacuo (2 kPa) to give a solid residue that was dried overnight (2 kPa; P$_2$O$_5$; 35° C.). This solid was suspended in CH$_3$CN (100 mL) and stirred for several hours, filtered and dried (2 kPa; P$_2$O$_5$; 35° C.) to afford the desired product (19.72 g; 0.0345 mol). Yield 88%.

m.p.: 111–115° C.

Acidic titer (0.1 N NaOH) 96.2%; equivalent point pH 6.54

Complexometric titer (0.1 N ZnSO$_4$): 96%

HPLC: 99.5% (area %)

Weight loss (70° C. high vacuum): 1.58%

$^{13}$C-NMR, $^1$H-NMR, MS and IR spectra are consistent with the structure.

$[\alpha]_{80}{}^{20}$ (c 2.5; 0.4 N NaOH)

| λ(nm) | 589 | 578 | 546 | 436 | 405 | 365 |
|---|---|---|---|---|---|---|
| $[\alpha]_\lambda{}^{20}$ | +10.68° | +11.60° | +13.32° | +26.79° | +36.35° | +58.47° |

Elemental analysis (%)

|  | C | H | N |
|---|---|---|---|
| Calcd. | 58.63 | 6.15 | 7.33 |
| Found | 58.61 | 6.36 | 7.97 |

E) [[[(N,N'-[[(Carboxymethyl)imino]di-2,1-ethanediyl]-bis[Ncarboxymethyl)-L-phenylalaninate]](5-)]gadolinate(2-)]dihydrogen compound with 1-deoxy-1-(methylamino)-D-glucitol (1:2)

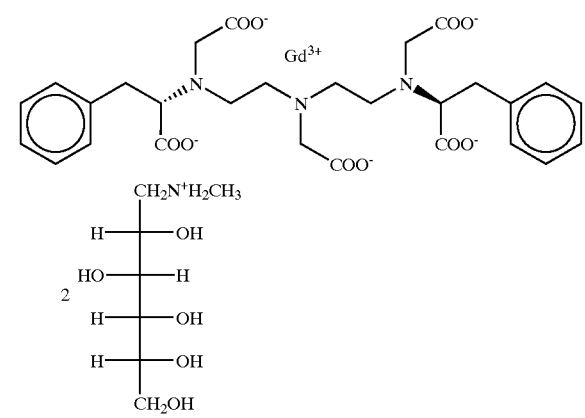

To a solution obtained suspending the product obtained at the previous step (14.34 g; 0.025 mol) in H$_2$O and neutralizing (pH 7.0) by addition of 1 N aq. meglumine (83 mL; 0.083 mol), was added, over 15 min, a solution of GdCl$_3$ 6 H$_2$O (8.92 g; 0.024 mol) in H$_2$O (100 mL) maintaining the pH at 7 with 1 N aq. meglumine (37 mL; 0.037 mol) by means of a pH-stat apparatus. The reaction mixture was nanofiltered:

Apparatus: Celfa Unit C-123-P
Membrane: Desal DK 4040
Pressure: 1 MPa
Time: 17 h

| | Conditions: | | |
|---|---|---|---|
| | volume | starting conductivity | final conductivity |
| retentate | 0.35 L | 11 mS/cm | 2.9 mS/cm |
| permeate | 5.5 L | 2.8 mS/cm | 0.03 mS/cm | and then freeze-dried. After further drying (2 kPa; P$_2$O$_5$; 40° C.) the title compound was obtained (24.5 g; 0.0219 mol). Yield 87%.

m.p.: 135–139° C.

HPLC: 99.2% (area %)—Chromatographic method:

Stationary phase: Spheri -10 RP-2 10 mm;

250×4, 6 mm column packed by Applied Biosystem;

Temperature: 45° C.;

Mobile phase: isocratic elution with premixed mobile phase: 1 g of n-octylamine is added to 240 mL of acetonitrile mixed with 760 mL of water. The solution is buffered to pH 6 with $H_3PO_4$;

Flow rate: 1.0 mL min$^{-1}$;

Detection (UV): 210 nm;

Injection: 10 ml;

Sample concentration: 1–10 mg mL$^{-1}$;

Instrumentation: Merck KGaA—Hitachi L 6200 low pressure gradient pump, Merck KGaA—Hitachi AS 2000 autosampler, Merck KGaA T6300 column thermostat, Merck KGaA—Hitachi L 3000 diode array detector.

K.F.: 1.86%

MS and IR spectra were consistent with the structure.

Elemental analysis (%):

|  | C | H | Gd | N |  |
| --- | --- | --- | --- | --- | --- |
| Calcd. | 45.11 | 5.95 | 14.06 | 6.26 |  |
| Found | 44.80 | 5.97 | 14.15 | 6.26 | anhydrous |

EXAMPLE 17

Compound 12

[[[S-(R*,R*)]-N,N-Bis[2-[(carboxymethyl)(1-carboxy-2-phenylethyl)amino]ethyl]-L-phenylalaninate(5-)]gadolinate(2-)]dihydrogen compound with 1-deoxy-1-(methylamino)-D-glucitol (1:2)

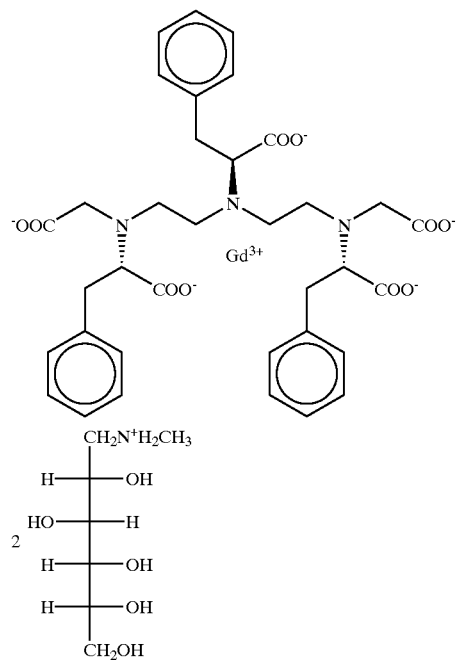

A) N-(2-Bromoethyl)-N-[2-(1,1-dimethylethoxy)-2-oxoethyl]-L-phenylalanine 1,1-dimethylethyl ester

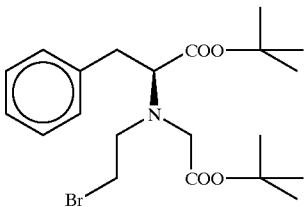

The product is prepared according to Example 3.

B) [S-(R*,R*)]-N,N-Bis[2-[[2-(1,1-dimethylethoxy)-2-oxoethyl][2-(1,1-dimethylethoxy)-2-oxo-1-(phenylmethyl)ethyl]amino]ethyl]-L-phenylalanine 1,1-dimethylethyl ester

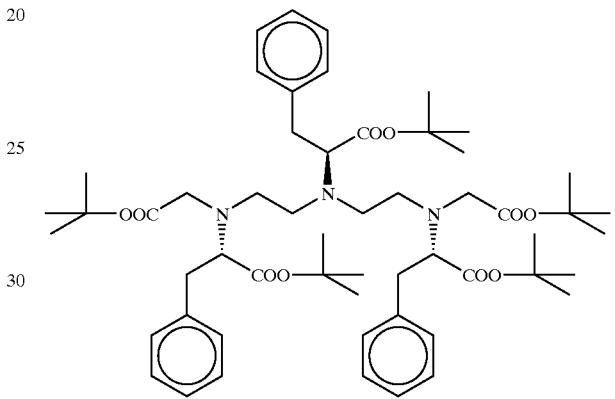

A two-phase mixture of N-(2-Bromoethyl)-N-[2-(1,1-dimethylethoxy)-2-oxoethyl]-L-phenylalanine 1,1-dimethylethyl ester (68 g; 0.15 mol) and L-phenylalanine 1,1-dimethylethyl ester (Example 3, Step A) (13.3 g; 0.06 mol) in MeCN (800 mL) and 2 M pH 8 phosphate buffer (500 mL) was stirred for 17 h. The upper layer was separated and further 2 M pH 8 phosphate buffer (200 mL) was added. After 24 h, the upper layer was separated and the solution was evaporated. The residue was dissolved in n-hexane (500 mL) and the solution was washed with $H_2O$ (300 mL). After drying ($Na_2SO_4$), the solution was evaporated and the residue was purified by flash chromatography (Stationary phase: silica gel 230–400 mesh Merck KGaA art 9385 (1 kg) Eluent: 10:1 n-hexane/EtOAc) to give the desired product (48 g; 0.051 mol). Yield 85%

TLC: Rf 0.50

Stationary phase: Silica gel plates 60 F254 (Merck KGaA code 5715)

Eluent: n-hexane/EtOAc 4:1

Detection: 1% $KMnO_4$ in 1N NaOH

HPLC: 96.9% (area %)—Chromatographic method:

Stationary phase: Lichrosorb RP-Select B 5 µm;

250×4 mm; column packed by Merck KGaA;

Temperature: 45° C.;

Mobile phase: gradient elution;

A=0.01 M $KH_2PO_4$ and 0.017 M $H_3PO_4$ in water

B=$CH_3CN$

| Gradient timetable: | min | % A | % B |
|---|---|---|---|
| | 0 | 95 | 5 |
| | 30 | 20 | 80 |
| | 55 | 20 | 80 |

Flow rate: 1 mL min$^{-1}$;
Detection (UV): 210 nm;
Injection: 10 μL;
Sample concentration: 1 mg mL$^{-1}$;
Instrumentation: Merck KGaA—Hitachi high pressure gradient pump system (two Lachrom L 7100 pumps), Merck KGaA—Hitachi Lachrom L 7200 autosampler, Merck KGaA—Hitachi Lachrom L 7300 column thermostat, Merck KGaA—Hitachi Lachrom L 7400 UV detector.

$^1$H-NMR, $^{13}$C-NMR, MS and IR spectra are consistent with the structure.

$[\alpha]_{80}^{20}$ (c 5.14; CHCl$_3$)

| λ(nm) | 569 | 578 | 546 | 436 | 405 | 365 |
|---|---|---|---|---|---|---|
| $[\alpha]_\lambda^{20}$ | −39.25° | −41.53° | −47.85° | −85.20° | −104.83° | no transmittance |

Elemental analysis (%):

| | C | H | N |
|---|---|---|---|
| Calcd. | 69.96 | 8.65 | 4.45 |
| Found | 69.83 | 8.31 | 4.21 |

C) [S-(R*,R*)]-N,N-Bis[2-[(carboxymethyl)(1-carboxy-2-phenylethyl)amino]ethyl]-L-phenylalanine

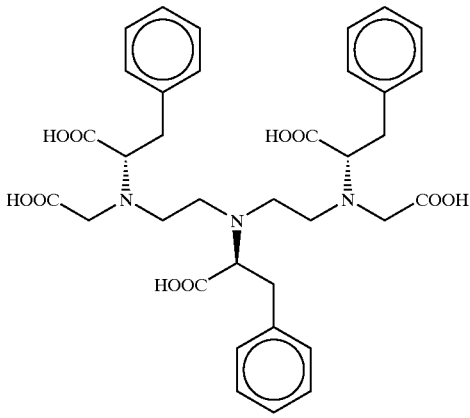

Trimethylsilyl iodide (commercial product) (80 g; 0.40 mol) was dripped, in 40 min, into a solution of the compound obtained from the previous preparation (37.8 g; 0.040 mol) in CHCl$_3$ (200 mL) maintained under stirring at 5 10° C. After 19 h the mixture was dropped in H$_2$O/ice (600 g). The amorphous precipitate was dissolved in MeOH (200 mL) and 2N NaOH (100 mL) was added to the solution up to pH 7. The solution was concentrated to remove methanol and dropped into 1 N HCl (250 mL) containing NaHSO$_3$ (1 g). The precipitate (containing iodide ions) was dissolved in CH$_3$CN (80 mL) and the solution was diluted with H2O (300 mL) and few drops of 37% HCl to maintain the solution clear. The solution was loaded on to a column of Amberlite XAD-1600 (1 L), eluted with 4:1 CH$_3$CN/0.1 N HCl just before and after the loading to prevent the precipitation of the product on to the resin. The column was washed with 4:1 CH$_3$CN/H$_2$O (2 L), then the product was eluted with 1:1 CH$_3$CN/H$_2$O (3 L). The eluate was evaporated at 40° C. and 1.3 kPa and the residue was treated with H$_2$O (50 mL) to afford a crystalline solid. After filtration and drying (P$_2$O$_5$, 50° C., 2 kPa) the desired product was obtained (19.6 g; 0.0295 mol). Yield 74% mp: 116° C. synt.; 142° C. dec.
Acidic titer (0.1 N NaOH) 97.9%; equivalent point pH 7.4
HPLC: 97.3% (area %) Chromatographic method of previous step B)
K.F.: 0.87%

$^1$H-NMR, $^{13}$C-NMR, MS and IR spectra were consistent with the structure.

$[\alpha]_\lambda^{20}$ (c 2.53; 4 N NaOH)

| λ(nm) | 589 | 576 | 546 | 436 | 405 | 365 |
|---|---|---|---|---|---|---|
| $[\alpha]_\lambda^{20}$ | +14.57° | +15.33° | 17.58° | +31.49° | +38.69° | +52.28° |

Elemental analysis (%):

| | C | H | N | |
|---|---|---|---|---|
| Calcd. | 63.34 | 6.23 | 6.33 | |
| Found | 63.28 | 6.02 | 6.39 | anhydrous |

D) [[[S-(R*,R*)]-N,N-Bis[2-[(carboxymethyl)(1-carboxy-2-phenylethyl)amino]-ethyl]-L-phenylalaninate(5-)] gadolinate(2-)]dihydrogen compound with 1-deoxy-1-(methylamino)-D-glucitol (1:2)

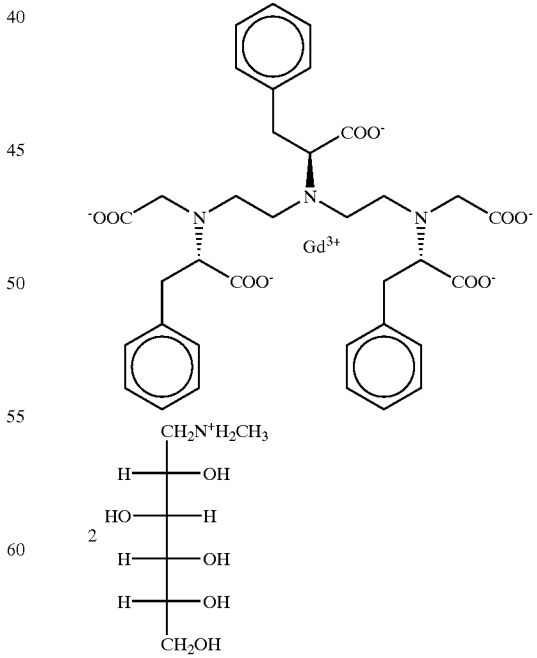

A solution of GdCl$_3$.6 H$_2$O (8.18 g; 0.022 mol) in H$_2$O (50 mL) was dripped over 3 h into a solution of the compound obtained in the previous step (14.6 g; 0.022 mol) neutralised (pH 7.0) by addition of 1 N meglumine (70 mL; 0.07 mol). The reaction mixture was maintained at pH 7 with 1 N meglumine (37.6 mL; 0.038 mol) by means of a pH-stat apparatus. The complexation was monitored by HPLC.

Chromatographic method:

Stationary phase: Lichrospher 100 RP-8 5 mm;

250×4 mm column packed by Merck KGaA;

Temperature: 40° C.;

Mobile phase: isocratic elution with premixed mobile phase: 1 g of n-nonylamine is added to 400 mL of μ acetonitrile mixed with 600 mL of water. The solution is buffered to pH 6 with $H_3PO_4$;

Flow rate: 1 mL $min^{-1}$;

Detection (UV): 210 nm;

Injection: 10 μL;

Sample concentration: 1 mg $mL^{-1}$;

Instrumentation: Merck KGaA—Hitachi high pressure gradient pump system (two Lachrom L 7100 pumps), Merck KGaA—Hitachi Lachrom L 7200 autosampler, Merck KGaA—Hitachi Lachrom L 7300 column thermostat, Merck KGaA—Hitachi Lachrom L 7400 UV detector.

The solution was filtered through Millipore HA 0.45 m and loaded on to Amberlite® XAD 1600 (1000 mL), the resin was washed with $H_2O$, 1:9 MeOH/$H_2O$, 1:4 MeOH/$H_2O$, 2:3 MeOH/$H_2O$, 4:1 MeOH/$H_2O$ and the product was eluted with MeOH. After evaporation of methanol, the pH of the solution was corrected to 6.8 with 1 N meglumine (0.4 mL) and the solution was concentrated to dryness at 40° C. and 1.3 kPa. After drying ($P_2O_5$, 50° C., 270 Pa) the title compound (23.9 g; anhydrous 23.0 g; 0.195 mol) was obtained as a white solid. Yield 89%.

mp: 56° C. (143° C. synt.)

HPLC: 99.7% (area %)

K.F.: 3.63%

The MS spectrum is consistent with the structure.

Elemental analysis (%):

|  | C | H | Gd | N |  |
|---|---|---|---|---|---|
| Calcd. | 48.70 | 6.01 | 13.01 | 5.80 |  |
| Found | 49.46 | 6.24 | 13.30 | 5.88 | anhydrous |

EXAMPLE 18

Compound 13

[[[[S-(R*,R*)]-α,α'-[[(Carboxymethyl)imino]bis[2,1-ethanediyl[(carboxymethyl)imino]]]bis[cyclohexanepropanoate]](5-)]gadolinate(2-)] dihydrogen compound with 1-deoxy-1-(methylamino)-D-glucitol (1:2)

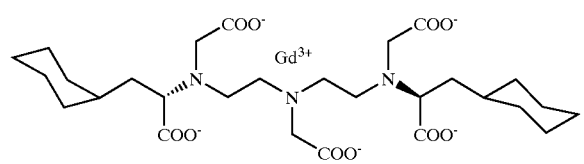

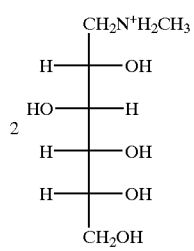

A) N,N'-[[[2-(1,1-Dimethylethoxy)-2-oxoethyl]imino]di-2,1-ethanediyl]bis[N-[2-(1,1-dimethylethoxy)-2-oxoethyl]-L-phenylalanine 1,1-dimethylethyl ester]

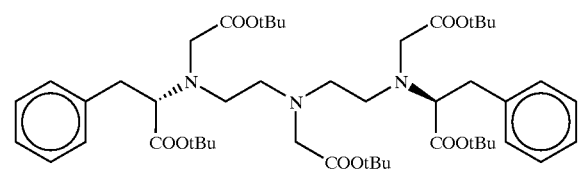

The product is prepared according to Example 16, Step (C)

B) [S-(R*,R*)]-α,α'-[[[2-(1,1-Dimethylethoxy)-2-oxoethyl]imino]bis[2,1-ethanediyl[[2-(1,1-dimethylethoxy)-2-oxoethyl]imino]]]bis-[cyclohexanepropanoic acid 1,1-dimethylethyl ester]

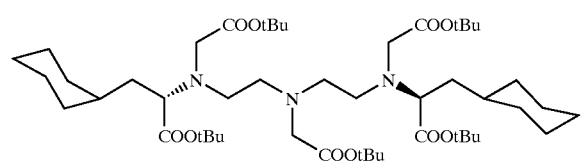

To a solution of N,N'-[[[2-(1,1-Dimethylethoxy)-2-oxoethyl]imino]di-2,1-ethanediyl]bis[N-[2-(1,1-dimethylethoxy)-2-oxoethyl]-L-phenylalanine 1,1-dimethylethyl ester] (35.9 g; 0.042 mol) in MeOH (300 mL), wet 5% Rh on carbon (commercial product) (8 g) was added and the resulting suspension was hydrogenated, in a Parr bomb (mod. 4561, 600 mL vessel) (theoretical hydrogen 5.64 L; 0.252 mol), at 4×10⁶ Pa (40 bar) and at 60–65° C. for 6 h. The mixture was cooled, the catalyst was removed by filtration through buchner funnel and the filtrate was evaporated under reduced pressure. The residue was dissolved in absolute EtOH (500 mL), concentrated to dryness, dissolved in n-hexane (500 mL) and again concentrated under reduced pressure. The residue (36 g) was purified by flash chromatography:

Sample: Solid dispersion in silica gel 35–70 mesh

Stationary phase: 1200 g Silica gel 230–400 mesh

Stationary phase conditioning: n-hexane

Eluent: n-hexane/EtOAc gradient

| (v/v) | Volume (L) |
|---|---|
| 100/0 | 1 |
| 97.5/2.5 | 1 |
| 95/5 | 2 |
| 92.5/7.5 | 2 |
| 90/10 | 2 |
| 87.5/12.5 | 2 |
| 85/15 | 3 | to give, after further drying ($P_2O_5$; 0.13 kPa; 50° C.), the desired product (30.5 g; 0.035 mol). Yield 83%.
Acidic titer (0.1 N HCl): 98.3%; equivalent point pH 4.49
TLC: Rf 0.52
Stationary phase: Silica gel plates 60 $F_{254}$
Eluent: 4:1 (v/v) n-hexane/EtOAc
Detection: 1% $KMnO_4$ in 1 N NaOH
HPLC: 98.5% (area %)
Chromatographic method:
Stationary phase: Lichrosorb RP-Select B 5 mm; 250×4 mm column packed by Merck KGaA;
Temperature: 45° C.;
Mobile phase: gradient elution;
A=0.017 M $H_3PO_4$ in water
B=$CH_3CN$

| Gradient timetable: | min | % A | % B |
|---|---|---|---|
| | 0 | 82 | 18 |
| | 30 | 15 | 85 |
| | 45 | 15 | 85 |

Flow rate: 1 mL $min^{-1}$;
Detection (UV): 210 nm;
Injection: 10 µL;
Sample concentration: 1 mg $mL^{-1}$;
Instrumentation: Merck KGaA—Hitachi L 6200 low pressure gradient pump, Merck KGaA—Hitachi AS 2000 autosampler, Merck KGaA T6300 column thermostat, Merck KGaA—Hitachi L 3000 diode array detector.
Weight loss (70° C. high vacuum): 1.59%
$^1$H-NMR, $^{13}$C-NMR, MS and IR spectra were consistent with the structure.
$[\alpha]_\lambda^{20}$ (c 5.43; $CHCl_3$)

| λ(nm) | 589 | 578 | 546 | 436 | 405 | 365 |
|---|---|---|---|---|---|---|
| $[\alpha]_\lambda^{20}$ | −24.24° | −25.41° | −29.12° | −52.39° | −63.85° | −87.07° |

Elemental analysis (%):

| | C | H | N |
|---|---|---|---|
| Calcd. | 66.56 | 10.12 | 4.85 |
| Found | 66.82 | 10.28 | 4.88 |

C) [S-(R*,R*)]-α,α'-[[(Carboxymethyl)imino]bis[2,1-ethanediyl-[(carboxymethyl)imino]]]-bis[cyclohexanepropanoic acid]

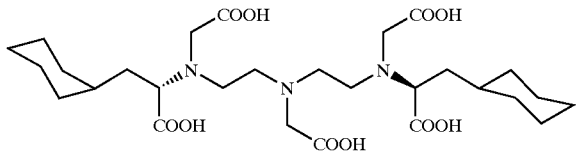

Trifluoroacetic acid (commercial product) (81.4 g; 0.714 mol) was dripped, over 30 min, into a solution of the pentaester obtained in the previous step (29 g; 0.0335 mol) in $CH_2Cl_2$ (20 mL) stirred at −15÷−10° C. The cooling bath was removed and the reaction stirred at room temperature for 90 h. The solvent was removed by evaporation under reduced pressure (2 kPa) and the residue taken up with fresh trifluoroacetic acid (81.4 g; 0.714 mol). After additional 50 h stirring, the reaction mixture was evaporated under reduced pressure (2 kPa) to give a brown oil that was dissolved in $CH_2Cl_2$ (100 mL) and again evaporated in vacuo. This operation was repeated twice. Following the same procedure the residue was treated with $Et_2O$ (2×100 mL) and with $CH_3CN$ (50 mL), obtaining a brownish amorphous solid that was dissolved in 1/1 (v/v) $CH_3CN$/$H_2O$ (50 mL), acidified with 37% HCl (10 mL) and diluted to 200 mL with $H_2O$. The solution was loaded onto a column of Amberlite® XAD 1600 (1 L) and the product eluted with a $H_2O$/$CH_3CN$ gradient:
Conditioning: 90/10 (v/v) $H_2O$/$CH_3CN$
Elution: $H_2O$/$CH_3CN$ gradient

| (v/v) | Volume (L) |
|---|---|
| 90/10 | 4.5 |
| 80/20 | 1.5 |
| 70/30 | 2 |
| 60/40 | 3.5 |
| 50/50 | 1.5 |
| 20/80 | 1.5 |

The product elutes with 60/40 (v/v) $H_2O$/$CH_3CN$

Fractions containing the pure ligand were collected and concentrated in vacuo (2 kPa). The azeotropic removal of $CH_3CN$ led to the separation of a precipitate that was filtered, washed with $H_2O$ and dried overnight (2 kPa; $P_2O_5$; 40° C.) to afford the desired product (14.71 g; 0.025 mol). Yield 75%.

m.p.: 116–120° C.

Acidic titer (0.1 N NaOH): 96.3%; equivalent point pH 7.24

Complexometric titer (0.1 N $ZnSO_4$): 96.5%

HPLC: 99% (area %)—Chromatographic method of previous step B).

K.F.: 2.29%

$^1$H-NMR, $^{13}$C-NMR, MS and IR spectra were consistent with the structure.

$[\alpha]_{80}^{20}$ (c 2.5; 0.4N NaOH)

| λ(nm) | 589 | 578 | 546 | 436 | 405 | 365 |
|---|---|---|---|---|---|---|
| $[\alpha]_\lambda^{20}$ | +4.87° | +5.15° | +5.67° | +9.19° | +12.58° | +19.73° |

Elemental analysis (%):

| | C | H | N | $Cl^-$ | F |
|---|---|---|---|---|---|
| Calcd. | 57.42 | 8.09 | 7.17 | | |
| Found | 56.16 | 8.39 | 7.00 | <0.1 | <0.1 |
| Corresp. to | 57.47 | 8.32 | 7.16 | anhydrous | |

D) [[[[S-(R*,R*)]-α,α'-[[(Carboxymethyl)imino]bis[2,1-ethanediyl[(carboxymethyl)imino]]]bis[cyclohexanepropanoate]](5-)]gadolinate(2-)]dihydrogen compound with 1-deoxy-1-(methylamino)-D-glucitol (1:2)

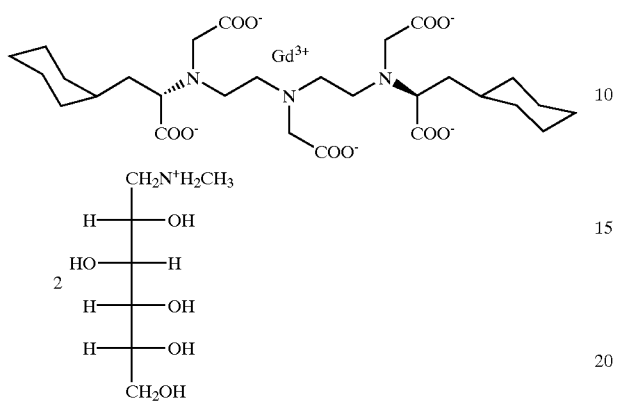

To a solution obtained suspending the product obtained in the previous step (12.6 g; 0.0215 mol) in $H_2O$ and neutralising (pH 7.0) by addition of 1 N aq meglumine (75 mL; 0.075 mol), was added, over 15 min, a solution of $GdCl_3$ 6 $H_2O$ (7.8 g; 0.021 mol) in $H_2O$ (100 mL) maintaining the pH at 7 with 1 N aq meglumine (30 mL; 0.03 mol) by means of a pH-stat apparatus. The reaction mixture was nanofiltered
Apparatus: Celfa Unit C 123 P
Membrane: Desal DK 4040
Pressure: 1 MPa
Time: 15 h

| | Conditions: | |
|---|---|---|
| | volume | starting conductivity | final conductivity |
| retentate | 0.35 L | 10.6 mS/cm | 2.2 mS/cm |
| permeate | 5 L | 2.6 mS/cm | 0.018 mS/cm | and then freeze-dried. After further drying (2 kPa; $P_2O_5$; 40° C.) the title compound was obtained (22.5 g; 0.0199 mol). Yield 92%.
m.p.: 145–150° C.
HPLC: 99.9% (area %)—Chromatographic method:
Stationary phase: Spheri-10 RP-2 10 μm;
250×4, 6 mm column packed by Applied Biosystem;
Temperature: 45° C.;
Mobile phase: isocratic elution with premixed mobile phase: 1 g of n-octylamine is added to 350 mL of acetonitrile mixed with 650 mL of water. The solution is buffered to pH 6 with conc. $H_3PO_4$;
Flow rate: 1.0 mL $min^{-1}$;
Fluorimeter Detection: Ex 275 nm, Em 315 nm;
Injection: 10 μL;
Sample concentration: 5–10 mg $mL^{-1}$;
Instrumentation: Merck KGaA—Hitachi L 6200 low pressure gradient pump, Merck KGaA—Hitachi AS 2000 autosampler, Merck KGaA T6300 column thermostat, Merck KGA—Hitachi F 1080 Fluorescence Detector
K.F.: 1.14%
MS and IR spectra were consistent with the structure.

Elemental analysis (%):

| | C | H | Gd | N | |
|---|---|---|---|---|---|
| Calcd. | 44.63 | 6.96 | 13.91 | 6.20 | |
| Found | 44.35 | 6.91 | 14.00 | 6.21 | anhydrous |

EXAMPLE 19

Compound 14

[[[[[aS-[aR*(a'R*),(1R*)]]-a,a1-[[(-Carboxy-2-cyclohexylethyl)imino]bis[2,1-ethanediyl-[(carboxymethyl)imino]]]bis[cyclohexanepropanoate]](5-)]gadolinate(2-)] dihydrogen compound with 1-deoxy-1-(methylamino)-D-glucitol (1:2)

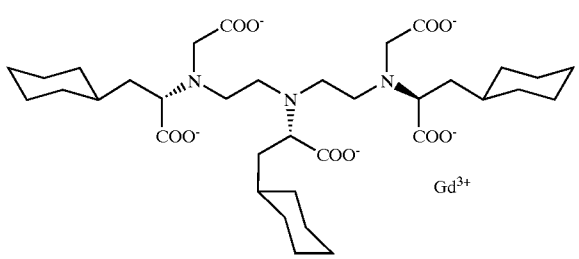

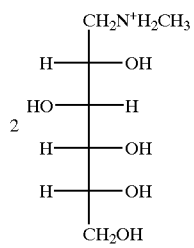

A) [S-(R*,R*)]-N,N-Bis[2-[[2-(1,1-dimethylethoxy)-2-oxoethyl][2-(1,1-dimethylethoxy)-2-oxo-1-(phenylmethyl)ethyl]amino]ethyl]-L-phenylalanine 1,1-dimethylethyl ester

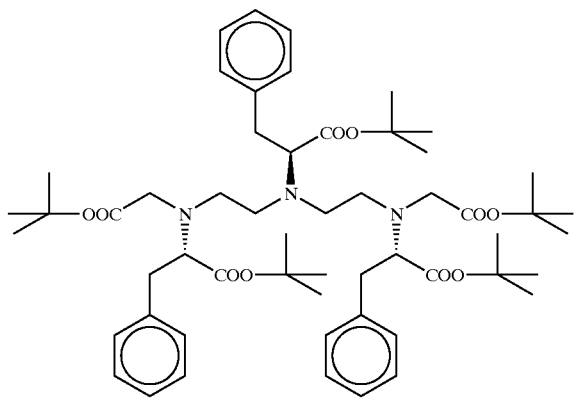

The product is prepared according to Example 17, Step (B).

B) [α-[R*(α'R*),(1R*)]]-α,α'-[[1-(1,1-Dimethylethoxy)carbonyl-2-cyclohexylethyl]imino]bis[2,1-ethanediyl-[(1,1-dimethylethoxy)-2-oxoethyl])imino]-bis[cyclohexanepropanoic acid 1,1-dimethylethyl ester]

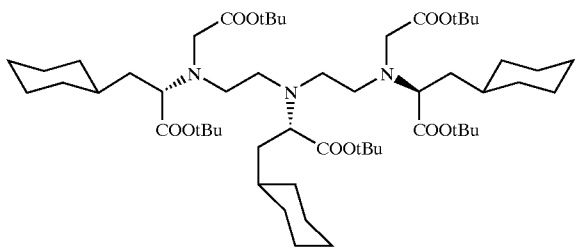

To a solution of [S-(R*,R*)]-N,N-bis[2-[[2-(1,-dimethylethoxy)-2-oxoethyl][2-(1,1-dimethylethoxy)-2-oxo-1-(phenylmethyl)ethyl]amino]ethyl]-L-phenylalanine 1,1-dimethylethyl ester (67.4 g; 0.07 mol) in MeOH (500 mL), 5% Rh on carbon (commercial product) (13.4 g) was added and the resulting suspension was hydrogenated (theoretical hydrogen 14.1 L; 0.63 mol) at 40 bar (4 MPa) and at 60–65° C. for 6 h. The reaction was monitored by HPLC (Chromatographic method of Example 17, B)). The mixture was cooled and the catalyst was removed by filtration on Buchner funnel. The filtrate was concentrated under reduced pressure and the residue was purified by flash-chromatography (Stationary phase:

Silica gel 230–400 mesh Merck KGaA art 9385 (600 g) Eluent: 100:1 30:1 n-hexane/EtOAc gradient) to give the desired product (51.9 g; 0.054 mol). Yield 77%

TLC: Rf 0.80

Stationary phase: Silica gel plates 60 $F_{254}$ (Merck KGaA code 5715)

Eluent: 4:1 n-hexane/EtOAc

Detection: 1% $KMnO_4$ in 1N NaOH or Pancaldi spray ($CeSO_4 \cdot 4 H_2O$ 1 g; $(NH_4)_6Mo_7O_{24} \cdot 4 H_2O$ 21 g; 98% $H_2SO_4$ 31 mL; $H_2O$ 470 mL) and heating to 200° C.

$^1$H-NMR, $^{13}$C-NMR, MS and IR spectra were consistent with the structure.

$[\alpha]_\lambda^{20}$ (c 5.00; CHCl

| λ(nm) | 589 | 578 | 546 | 436 | 405 | 365 |
|---|---|---|---|---|---|---|
| $[\alpha]_\lambda^{20}$ | −42.92° | −45.88° | −51.29° | −90.17° | −111.23° | −152.08° |

Elemental analysis (%):

| | C | H | N |
|---|---|---|---|
| Calcd. | 68.64 | 10.37 | 4.37 |
| Found | 68.83 | 10.74 | 4.26 |

C) [αS-[αR*(α'R*),(1R*)]]-α,α'-[[(1-Carboxy-2-cyclohexylethyl)imino]bis[2,1-ethanediyl-[(carboxymethyl)-imino]]]bis(cyclohexanepropanoic acid]

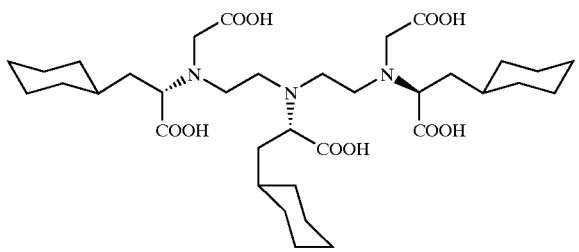

Trimethylsilyl iodide (commercial product) (106 g; 0.53 mol) was dripped, in 40 min, into a solution of the compound obtained in the previous step (51 g; 0.053 mol) in $CHCl_3$ (250 mL) maintained under stirring at 5 10° C. After 88 h the mixture was dropped in $H_2O$/ice (300 g). The amorphous precipitate was dissolved by the addition of 2 N NaOH until pH 8 was reached, the solution was evaporated to remove $CHCl_3$ and acidified with 18% HCl (to pH 2) to obtain an orange precipitate, that was filtered. The solid was dissolved in 30% MeOH (2 L) and 10 N NaOH (to pH 10), $Na_2SO_3$ (500 mg) was added and the solution was acidified with 18% HCl (to pH 4,8). The solution was loaded on to a column of Amberlite® XAD 1600 resin (50 mm; h 920 mm; 1800 mL) and washed with 3:6:1 MeOH/$H_2O$/37% HCl (1 L), 3:7 MeOH/$H_2O$; 1:1 MeOH/$H_2O$, 7:3 MeOH/$H_2O$, 9:1 MeOH/$H_2O$, MeOH. The product was then eluted with 9:1 MeOH/25% aq. $NH_3$. The eluate was concentrated to remove MeOH and $NH_3$ and the residual solution (300 mL) was acidified with 37% HCl. The precipitate (gel) was filtered, washed five times with $H_2O$ (to remove Cl⁻) and dried ($P_2O_5$, 50° C., 2 kPa). The desired product was obtained (27.5 g; 0.0403 mol). Yield 76% mp: 161° C. (synt.) 169° C. (dec.)

Acidic titer (0.1 N NaOH): 94%; equivalent point pH 7.9

Complexometric titer (0.1 N $ZnSO_4$): 93.5%

K.F.: 3.69%

$^1$H-NMR, $^{13}$C-NMR, MS and IR spectra were consistent with the structure.

$[\alpha]_{80}^{20}$ (c 2.50; 4 N NaOH)

| λ(nm) | 589 | 578 | 546 | 436 | 405 | 365 |
|---|---|---|---|---|---|---|
| $[\alpha]_\lambda^{20}$ | +37.02° | +38.74° | +44.17° | +73.64° | +88.90° | +118.53° |

Elemental analysis (%):

| | C | H | N | Cl— |
|---|---|---|---|---|
| Calcd. | 61.65 | 8.72 | 6.16 | — |
| Found | 62.11 | 8.76 | 6.23 | >0.10 anhydrous |

D) [[[[[αS-[αR*(α'R*),(1R*)]]-α,α'-[[(1-Carboxy-2-cyclohexylethyl)imino]bis[2,1-ethanediyl-[(carboxymethyl)imino]]]bis[cyclohexanepropanoate]] (5-)]gadolinate (2-)]dihydrogen compound with 1-deoxy-1-(methylamino)-D-glucitol (1:2).

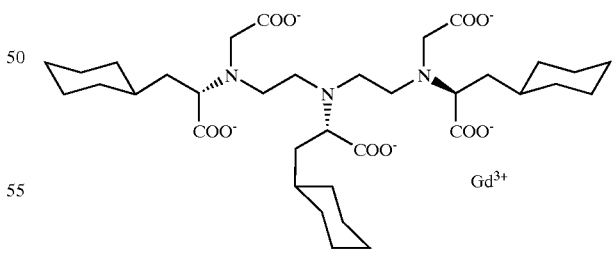
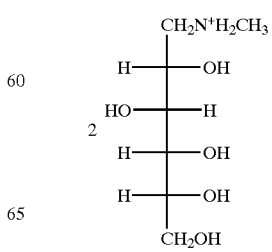

A solution of GdCl₃·6 H₂O (commercial product) (13 g; 0.035 mol) in H₂O (50 mL) was dripped over 3 h into a solution of the product obtained at the previous step (23.8 g; 0.035 mol) in H₂O (100 mL) neutralised (pH 7.0) by addition of 1 N meglumine (95.6 mL; 0.096 mol). The reaction mixture was maintained at pH 7 with 1 N meglumine (72.3 mL; 0.072 mol) by means of a pH-stat apparatus. The complexation was monitored by titration (12). The mixture was filtered through Celite and Millipore HA 0.45 μm and loaded on to a column of Amberlite XAD 1600 resin (50 mm; h 230 mm; 450 mL). The resin was washed with H₂O and the product was eluted with 1:4 MeOH/H₂O. After evaporation of methanol, the pH of the solution was corrected to 6.8 with 1 N meglumine (0.2 mL) and the solution was concentrated to dryness at 40° C. and 1.3 kPa. After drying (P₂O₅, 50° C., 270 Pa) the title compound was obtained (33.2 g; anhydrous 31.5 g; 0.025 mol). Yield 73%.

mp: 168° C. (125° C. synt.)

K.F.: 5.2%

The MS spectrum was consistent with the structure.

Elemental analysis (%):

|  | C | H | Gd | N |  |
|---|---|---|---|---|---|
| Calcd. | 47.98 | 7.40 | 12.82 | 5.71 |  |
| Found | 48.28 | 7.31 | 12.69 | 5.63 | anhydrous |

EXAMPLE 20

Compound 15

[[[[[αS-[αR*(α'R*),(1R*)]]-α,α'-[[(1-Carboxy-3-phenylpropyl)imino]bis[2,1-ethanediyl[(carboxymethyl)imino]]]bis[benzenebutanoate]] (5-)]gadolinate(2-)]dihydrogen compound with 1-deoxy-1-(methylamino)-D-glucitol (1:2)

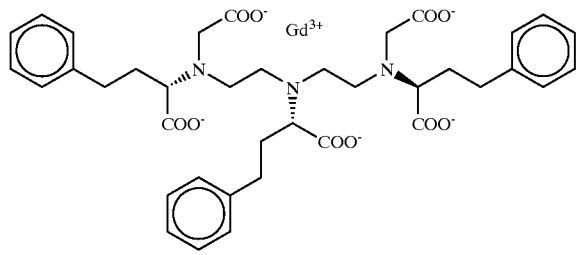

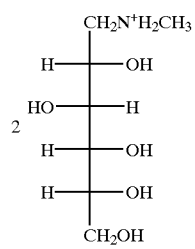

A) (S)-α-Aminobenzenebutanoic acid 1,1-dimethylethyl ester (C.A.S. [83079-77-0])

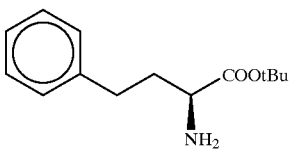

The compound has been prepared according to: Haslanger, M. F.; Sybertz, E. J.; Neustadt, B. R.; Smith, E. M.; Nechuta, T. L.; Berger, J. J. Med. Chem. 1989, 32(4), 737–739.

B) (S)-α-[[(2-(1,1-Dimethylethoxy)-2-oxoethyl](2-hydroxyethyl)amino]benzenebutanoic acid 1,1-dimethylethyl ester

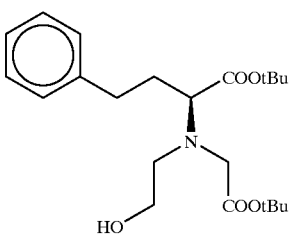

A solution of (S)-α-aminobenzenebutanoic acid 1,1-dimethylethyl ester (42.4 g; 0.18 mol), 2-(2-bromoethoxy)tetrahydropyran, prepared according to: J. Org. Chem. 1986, 51, 752–755, (39.7 g; 0.19 mol) and diisopropylethylamine (commercial product) (34 mL; 0.2 mol) in CH₃CN was refluxed for 21 h. Diisopropylethylamine (37.5 mL; 0.22 mol) and tert-butyl bromoacetate (commercial product) (39 g; 0.2 mol) were added and the reaction mixture refluxed for further 2.5 h. The solution was evaporated under reduced pressure (2 kPa) to give a residue that was dissolved in n-hexane (0.5 L) and washed with H2O (4×0.5 L). The organic phase was separated, treated with Carbopuron® 4 N, filtered, dried over Na₂SO₄ and evaporated under reduced pressure. The residue (90 g) was dissolved in cool (5° C.) MeOH (0.4 L) and cool (5° C.) 2N HCl (0.2 L) was added. After 4 h at r.t., cool (5° C.) 2N NaOH (0.25 L) and subsequently n-hexane (0.5 L) were added. The upper layer was separated and evaporated under reduced pressure to give a residue that was dissolved in n-hexane (0.5 L). The solution was washed with H₂O (2×0.25 L), dried over Na₂SO₄ and evaporated under reduced pressure. The residue (66 g) was purified by flash chromatography:

Sample: 1:1.5 (w/w) solid dispersion in silica gel 35–70 mesh

Stationary phase: 1 kg silica gel 230–400 mesh

Stationary phase conditioning: n-hexane

Eluent: n-hexane/EtOAc gradient

| (v/v) | Volume (L) |
|---|---|
| 100/0 | 1 |
| 95/5 | 1 |
| 90/10 | 2 |
| 85/15 | 2 |
| 80/20 | 7 |

After further drying ($P_2O_5$; 0.13 kPa; 50° C.) the desired product was obtained (38.8 g; 0.098 mol). Yield 55%.

Acidic titer (0.1 N $HClO_4$): 100.7%
TLC: Rf 0.18
Stationary phase: Silica gel plates 60 $F_{254}$
Eluent: 3:1 (v/v) n-hexane/EtOAc
Detection: 1% $KMnO_4$ in 1 N NaOH
HPLC: 99% (area %)—Chromatographic method:
Stationary phase: Lichrosorb RP-Select B 5 μm; 250×4 mm column packed by Merck KGaA;
Temperature: 45° C.;
Mobile phase: gradient elution;
A=0.017 M $H_3PO_4$ in water
B=$CH_3CN$

| Gradient timetable: | min | % A | % B |
|---|---|---|---|
| | 0 | 82 | 18 |
| | 30 | 15 | 85 |
| | 45 | 15 | 85 |

Flow rate: 1 mL min$^{-1}$;
Detection (UV): 210 nm;
Injection: 10 μL;
Sample concentration: 1 mg mL$^{-1}$;
Instrumentation: Merck KGaA—Hitachi L 6200 low pressure gradient pump, Merck KGaA—Hitachi AS 2000 autosampler, Merck KGaA T6300 column thermostat, Merck KGaA—Hitachi L 3000 diode array detector.
Weight loss (70° C., high vacuum): 1.10%
$^1$H-NMR, $^{13}$C-NMR, MS and IR spectra were consistent with the structure.
[α]$_λ^{20}$ (c 5.14; $CHCl_3$)

| (nm) | 589 | 578 | 546 | 436 | 405 | 365 |
|---|---|---|---|---|---|---|
| [α]$_λ^{20}$ | −22.61° | −23.68° | −27.24° | −48.28° | −59.19° | −80.34° |

Elemental analysis (%):

| | C | H | N |
|---|---|---|---|
| Calcd. | 67.15 | 8.96 | 3.56 |
| Found | 67.65 | 9.31 | 3.75 |

C) (S)-α-[(2-Bromoethyl)[2-(1,1-dimethylethoxy)-2-oxoethyl]amino]benzenebutanoic acid 1,1-dimethylethyl ester

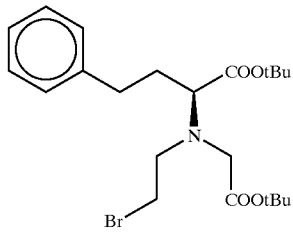

N-Bromosuccinimide (commercial product) (24.1 g; 0.13 mol) was added in a single portion to a solution of the product from the previous preparation (37 g; 0.094 mol) and triphenylphosphine (commercial product) (34.1 g; 0.13 mol) in $CH_2Cl_2$ (250 mL) cooled at −60° C. by means of EtOH-dry ice bath. After 5 min the bath was removed and the reaction was allowed to stand at r.t. for 2 h. After addition of ice (200 g), 5% aqueous $NaHCO_3$ (100 mL) and $CH_2Cl_2$ (100 mL), the organic phase was separated, washed with 5% aqueous $NaHCO_3$ (200 mL), $H_2O$ (200 mL), dried over $Na_2SO_4$ and evaporated under reduced pressure (2 kPa). The residue was suspended in n-hexane (300 mL), the solid precipitate (triphenylphosphine oxide) was filtered off, washing with cool n-hexane (500 mL), and the filtrate concentrated under reduced pressure (2 kPa) to 300 mL. Carbonpuron® 4N was added and the solution, cooled at 5° C., filtered. The filtrate was evaporated under reduced pressure (2 kPa) to give the desired product (43.1 g).

Argentometric titer (0.1 N $AgNO_3$): 94.3%
TLC: Rf 0.50
Stationary phase: Silica gel plates 60 $F_{254}$
Eluent: 85:15 (v/v) n-hexane/EtOAc
Detection: 1% $KMnO_4$ in 1 N NaOH D) [αS-[αR*(α'R*),(1R*)]]-α,α'-[[1-[(1,1-Dimethylethoxy)carbonyl]-3-phenylpropyl]imino]bis[2,1-ethanediyl[1-(1,1-dimethylethoxy)-2-oxoethyl]imino]-bis[benzenebutanoic acid 1,1-dimethylethyl ester]

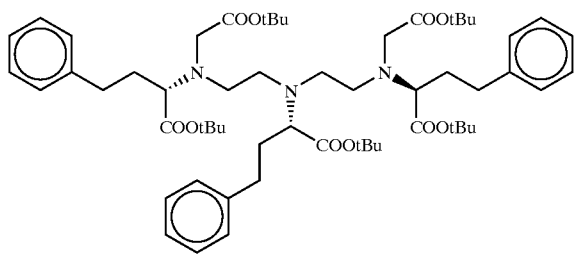

A two phase mixture of (S)-α-[(2-bromoethyl)[2-(1,1-dimethylethoxy)-2-oxoethyl]amino]benzene butanoic acid 1,1-dimethylethyl ester (43.1 g; 0.089 mol), (S)-α-aminobenzene butanoic acid 1,1-dimethylethyl ester (9.9 g; 0.042 mol) in MeCN (400 mL) and 2 M pH 8 phosphate buffer (250 mL) was stirred for 8 h. The aqueous layer was separated and replaced with fresh 2 M pH 8 phosphate buffer (200 mL). The same operation was repeated after 27 h and 52 h. The reaction mixture was stirred for additional 20 h (72 h total). The upper layer was separated and the solvent evaporated. The residue was dissolved in $Et_2O$ (500 mL) and the solution washed with $H_2O$ (2×250 mL). After drying ($Na_2SO_4$), the solvent was evaporated under reduced pressure (2 kPa). The residue was purified by flash chromatography:

Sample: 1:1.5 solid dispersion in silica gel 35–70 mesh
Stationary phase: 500 g silica gel 230–400 mesh
Stationary phase conditioning: n-hexane
Eluent: n-hexane/EtOAc gradient

| (v/v) | Volume (L) |
|---|---|
| 100/0 | 1 |
| 98/2 | 1 |
| 96/4 | 1 |
| 92/8 | 1 |
| 90/10 | 2.5 |
| 85/15 | 6.5 |

After further drying (10 Pa; 40° C.) the desired product was obtained (39.5 g; 0.04 mol). Yield 95%.

Acidic titer (0.1 N HCl): 95.3%; equivalent point pH 3.6
TLC: Rf 0.36
Stationary phase: Silica gel plates 60 $F_{254}$
Eluent: 85:15 (v/v) n-hexane/EtOAc
Detection: 1% $KMnO_4$ in 1 N NaOH
HPLC: 99% (area %) Chromatographic method of previous step B).
Weight loss (70° C., high vacuum): 0.61%
$^1$H-NMR, $^{13}$C-NMR, MS and IR spectra were consistent with the structure. $[\alpha]_\lambda^{20}$ (c 5.04; $CHCl_3$)

| $\lambda_{(nm)}$ | 589 | 578 | 546 | 436 | 405 | 365 |
|---|---|---|---|---|---|---|
| $[\alpha]_\lambda^{20}$ | −48.01° | −50.33° | −57.69° | −103.15° | −126.78° | −174.94° |

Elemental analysis (%):

|  | C | H | N |
|---|---|---|---|
| Calcd. | 70.63 | 8.89 | 4.26 |
| Found | 71.35 | 8.97 | 4.32 |

E) [αS-[αR*(α'R*),(1R*)]]-α,α'-[[(1-Carboxy-3-phenylpropyl)imino]bis[2,1-ethanediyl[(carboxymethyl)imino]]]bis(benzenebutanoic acid]

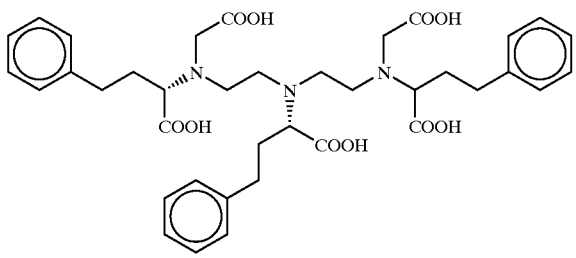

Trifluoroacetic acid (14.8 g; 0.13 mol) was dropped, over 15 min, into a solution of the pentaester from the previous preparation (39.1 g; 0.039 mol) in $CH_2Cl_2$ (50 mL) stirred at 0° C. The solution was evaporated under reduced pressure (2 kPa), the residue dissolved in trifluoroacetic acid (74 g; 0.65 mol) and the reaction mixture stirred at r.t. for 18 h. The solvent was removed by evaporation under reduced pressure (2 kPa) and the residue taken up -with fresh trifluoroacetic acid (74 g; 0.65 mol). After additional 72 h stirring, the solvent was evaporated affording an oil that was dissolved in $CH_2Cl_2$ (100 mL) and again evaporated in vacuo. This operation was repeated twice. Following the same procedure the residue was treated with $Et_2O$ (2×100 mL) and then with $CH_3CN$ (100 mL) to give an amorphous solid that was dissolved in 3/2 (v/v) $CH_3CN/H_2O$ (200 mL), acidified with 37% HCl (10 mL) and diluted to 400 mL with $H_2O$. The resulting solution was loaded onto a column of Amberlite® XAD 1600 (1 L) and the product eluted with a $H_2O/CH_3CN$ gradient:
Conditioning: 90/10 (v/v) $H_2O/CH_3CN$
Elution: $H_2O/CH_3CN$ gradient

| (v/v) | Volume (L) |
|---|---|
| 90/10 | 2.5 |
| 80/20 | 2 |
| 70/30 | 1 |
| 60/40 | 2 |
| 55/45 | 4 |
| 50/50 | 1 |
| 40/60 | 2 |

The product elutes with 60/40 (v/v) $H_2O/CH_3CN$.

The fractions containing the pure product were combined and evaporated under reduced pressure. On mixed fractions this procedure was repeated a second time in order to get a further amount of pure product. After further drying (2 kPa; $P_2O_5$; 40° C.) the desired compound (21.1 g; 0.029 mol) was obtained. Yield 74%.

mp: 115–120° C.

Acidic titer (0.1 N NaOH): 98%; equivalent point pH 7.0

Complexometric titer (0.1 N $ZnSO_4$) 96%

HPLC: 97% (area %) Chromatographic method of previous step B)

K.F.: 0.86%

$^1$H-NMR, $^{13}$C-NMR, MS and IR spectra were consistent with the structure.

$[\alpha]_\lambda^{20}$ (c 2.51; 0.4 N NaOH)

| $\lambda_{(nm)}$ | 589 | 578 | 546 | 436 | 405 | 365 |
|---|---|---|---|---|---|---|
| $[\alpha]_{80}^{20}$ | +6.80° | +7.00° | +11.18° | +14.28° | +23.07° | +6.64° |

Elemental analysis (%):

|  | C | H | N |  |
|---|---|---|---|---|
| Calcd. | 64.67 | 6.71 | 5.95 |  |
| Found | 64.01 | 6.79 | 6.13 | anhydrous |

F) [[[[[αS-[αR*(α'R*),(1R*)]]-α,α'-[[(1-Carboxy-3-phenylpropyl)imino]bis[2,1-ethanediyl[(carboxymethyl)imino]]]bis[benzenebutanoate]](5-)]gadolinate(2-)] dihydrogen compound with 1-deoxy-1-(methylamino)-D-glucitol (1:2)

To a solution obtained suspending the free ligand from the previous preparation (18.4 g; 0.025 mol) in $H_2O$ (50 mL) and neutralizing (pH 7.0) by addition of 1 N aq. meglumine (80 mL; 0.08 mol), was added dropwise a solution of $GdCl_3$. 6 $H_2O$ (8.92 g; 0.024 mol) in $H_2O$ (20 mL) maintaining the pH at 5 with 1 N aq. meglumine (40 mL; 0.04 mol) by means of a pH-stat apparatus. The reaction mixture was neutralized to pH 7 with 1 N aqueous meglumine, then nanofiltered:
Apparatus: Celfa Unit C-123-P
Membrane: Desal DK 4040
Pressure: 1 MPa
Time: 15 h Conditions:

|  | Volume | Starting conductivity | Final conductivity |
|---|---|---|---|
| Retentate | 0.3 L | 11.3 mS/cm | 2.7 mS/cm |
| Permeate | 5.8 L | 2.3 mS/cm | 0.03 mS/cm | and finally freeze-dried. After further drying (2 kPa; $P_2O_5$; 40° C.) the title compound (21.4 g; 0.017 mol) was obtained. Yield 68%.

mp: 133–138° C.

Free metal (0.001 M EDTA): >0.005%

HPLC: 99.2% (area %)—Chromatographic method:

Stationary phase: Spheri –10 RP-2 10 μm;250×4, 6 mm column packed by Applied Biosystem;

Temperature: 40° C.;

Mobile phase: isocratic elution with premixed mobile phase: 1 g of n-octylamine is added to 300 mL of acetonitrile mixed with 700 mL of water. The solution is buffered to pH 6 with conc. $H_3PO_4$;

Flow rate: 1.0 mL min$^{-1}$;

Detection (UV): 210 nm;

Injection: 10 μL;

Sample concentration: 1 mg mL$^{-1}$;

Instrumentation: Merck KGA—Hitachi L 6200 low pressure gradient pump, Merck KGaA—Hitachi AS 2000 autosampler, Merck KGaA T6300 column thermostat, Merck KGaA—Hitachi L 3000 diode array detector.

K.F.: 3.57%

MS and IR spectra were consistent with the structure.

Elemental analysis (%):

|  | C | H | Gd | N |  |
|---|---|---|---|---|---|
| Calcd. | 49.95 | 6.29 | 12.58 | 5.60 |  |
| Found | 50.27 | 6.23 | 12.17 | 5.81 | anhydrous |

What is claimed is:

1. A compound of formula (I), either in its racemic or enantiomeric form:

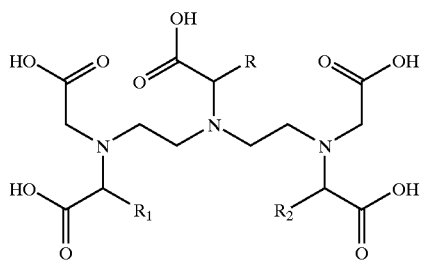

(I)

wherein:

R is a carboxy $C_1$–$C_{20}$ alkyl or (phenylmethoxy) lower alkyl and $R_1$ and $R_2$ are both (phenylmethoxy) lower alkyl, as well as the complexes of the compounds of formula (I) with metal ions having atomic number from 20 to 31, 39, from 42 to 44, 49 and from 57 to 83 and the salts thereof with physiologically acceptable organic bases selected from primary, secondary or tertiary amines, or basic amino acids, or with inorganic bases the cations of which are sodium, potassium, magnesium, calcium or mixtures thereof.

2. A compound of claim 1 wherein R, $R_1$ and $R_2$ are all

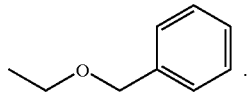

3. A compound as claimed in claim 1 wherein the complexed metal ion is selected from $Fe^{(2+)}$, $Fe^{(3+)}$, $Cu^{(2+)}$, $Cr^{(3+)}$, $Gd^{(3+)}$, $Eu^{(3+)}$, $Dy^{(3+)}$, $La^{(3+)}$, $Yb^{(3+)}$ and $Mn^{(2+)}$.

4. A compound selected from the following group:

[[[4S-[4R*,8(R*),12R*]]-4-Carboxy-8-[1-carboxy-2-(4-hydroxyphenyl)-ethyl]-5,11-bis(carboxymethyl)-1-phenyl-12-[(phenylmethoxy)methyl]-2-oxa-5,8,11-triazatridecan-13-oate(5-)]gadolinate(2-)]dihydrogen compound with 1-deoxy-1-methylamino-D-glucitol (1:2),

[[[4S-[4R*,8(1R*,2R*),12R*]]-4-Carboxy-5,11-bis-(carboxymethyl)-8-[(1-carbonxy-2-methyl)butyl]-1-phenyl-12-[(phenylmethoxy)methyl]-2-oxa-5,8,11-triazatridecan-13-oate(5-)]gadolinate(2-)]dihydrogen compound with 1-deoxy-1-(methylamino)-D-glucitol (1:2),

[[[4S-[4R*,8(1R*,2R*),12R*]]-4-Carboxy-5,11-bis(carboxymethyl)-8-[(1-carboxy-2-methyl)butyl]-1-phenyl-12-[(phenylmethoxy)methyl]-2-oxa-5,8,11-triazatridecan-13-oate(5-)]gadolinate(2-)]disodium salt (1:2)

[[[4S-[4R*,8(R*),12R*]]-4-Carboxy-5,11-bis(carboxymethyl)-8-(1-carboxy-pentyl)-1-phenyl-12-[(phenylmethoxy)methyl]-2-oxa-5,8,11-triazatridecan-13-oate(5-)]-gadolinate(2-)]disodium salt, and

[[[4S-[4R*,8(R*),12R*]]-4-Carboxy-5,11-bis(carboxymethyl)-8-[1,3-bis(carboxy)propyl]-1-phenyl-12-[(phenyl-methoxy)methyl]-2-oxa-5,8,11-triazatridecan-13-oate-(6-)]gadolinate(3-)]trihydrogen compound with 1-deoxy-1-(methylamino)-D-glucitol (1:3).

5. A paramagnetic chelate as claimed in clam 1 selected from the following group:

[[[4S-[4R*,8(R*),12R*]]-4-Carboxy-8-[1-carboxy-2-(4-hydroxyphenyl)-ethyl]-5,11-bis(carboxymethyl)-1-phenyl-12-[(phenylmethoxy)methyl]-2-oxa-5,8,11-triazatridecan-13-oate(5-)]gadolinate(2-)]dihydrogen compound with 1-deoxy-1-methylamino-D-glucitol (1:2),

[[[4S-[4R*,8(1R*,2R*),12R*]]-4-Carboxy-5,11-bis-(carboxymethyl)-8-[(1-carboxy-2-methyl)butyl]-1-phenyl-12-[(phenylmethoxy)methyl]-2-oxa-5,8,11-triazatridecan-13-oate(5-)]gadolinate(2-)]dihydrogen compound with 1-deoxy-1-(methylamino)-D-glucitol (1:2),

[[[4S-[4R*,8(1R*,2R*),12R*]]-4-Carboxy-5,11-bis(carboxymethyl)-8-[(1-carboxy-2-methyl)butyl]-1-phenyl-12-[(phenylmethoxy)methyl]-2-oxa-5,8,11-triazatridecan-13-oate(5-)]gadolinate(2-)]disodium salt (1:2)

[[[4S-[4R*,8(R*),12R*]]-4-Carboxy-5,11-bis(carboxymethyl)-8-(1-carboxypentyl)-1-phenyl-12-[(phenylmethoxy)methyl]-2-oxa-5,8,11-triazatridecan-13-oate(5-)]-gadolinate(2-)]disodium salt, and

[[[4S-[4R*,8(R*),12R*]]-4-Carboxy-5,11-bis(carboxymethyl)-8-[1,3-bis(carboxy)propyl]-1-phenyl-12-[(phenyl-methoxy)methyl]-2-oxa-5,8,11-triazatridecan-13-oate-(6-)]gadolinate(3-)]trihydrogen compound with 1-deoxy-1-(methylamino)-D-glucitol (1:3).

6. A contrast agent for magnetic resonance imaging comprising in a pharmaceutical composition at least one complex chelate compound of formula (I), either in its racemic or enantiomeric form:

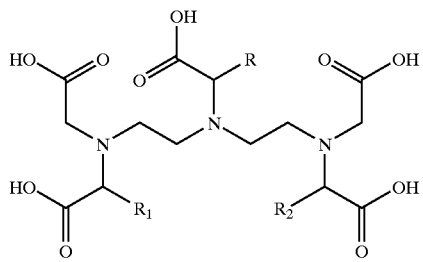

(I)

wherein:
R is a carboxy $C_1$–$C_{20}$ alkyl or (phenylmethoxy) lower alkyl and
$R_1$ and $R_2$ are both (phenylmethoxy) lower alkyl,
as well as the complexes of the compounds of formula (I) with metal ions having atomic number from 20 to 31, 39, from 42 to 44, 49 and from 57 to 83 and the salts thereof with physiologically acceptable organic bases selected from primary, secondary or tertiary amines, or basic amino acids, or with inorganic bases the cations of which are sodium, potassium, magnesium, calcium or mixtures thereof.

7. A method of imaging the blood pool of human or animal body by magnetic resonance comprising
(a) administering a complex chelate compound of formula (I), either in its racemic or enantiomeric form:

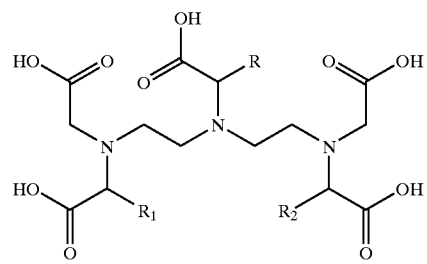

(I)

wherein:
R is a carboxy $C_1$–$C_{20}$ alkyl or (phenylmethoxy) lower alkyl and
$R_1$ and $R_2$ are both (phenylmethoxy) lower alkyl,
as well as the complexes of the compounds of formula (I) with metal ions having atomic number from 20 to 31, 39, from 42 to 44, 49 and from 57 to 83 and the salts thereof with physiologically acceptable organic bases selected from primary, secondary or tertiary amines, or basic amino acids, or with inorganic bases the cations of which are sodium, potassium, magnesium, calcium or mixtures thereof and then
(b) performing magnetic resonance imaging.

* * * * *